(12) United States Patent
Umemura et al.

(10) Patent No.: US 9,297,811 B2
(45) Date of Patent: Mar. 29, 2016

(54) PRODUCTION OF ENTERITIS EVOKING CAUSAL FACTOR BY HIGHLY PATHOGENIC ORAL BACTERIA AND HIGH SENSITIVITY DETECTION METHOD THEREFOR

(75) Inventors: Kazuo Umemura, Hamamatsu (JP); Kazuya Hokamura, Hamamatsu (JP); Kazuhiko Nakano, Suita (JP); Takashi Ooshima, Suita (JP); Ryota Nomura, Suita (JP); Koichiro Wada, Suita (JP)

(73) Assignees: National University Corporation Hamamatsu University School of Medicine, Shizuoka (JP); Osaka University, Osaka (JP)

( * ) Notice: Subject to any disclaimer, the term of this patent is extended or adjusted under 35 U.S.C. 154(b) by 73 days.

(21) Appl. No.: 13/583,723

(22) PCT Filed: Mar. 10, 2011

(86) PCT No.: PCT/JP2011/055688
§ 371 (c)(1),
(2), (4) Date: Nov. 27, 2012

(87) PCT Pub. No.: WO2011/111790
PCT Pub. Date: Sep. 15, 2011

(65) Prior Publication Data
US 2013/0059328 A1    Mar. 7, 2013

(30) Foreign Application Priority Data
Mar. 10, 2010  (JP) .................................. 2010-053079

(51) Int. Cl.
*C12Q 1/14* (2006.01)
*G01N 21/78* (2006.01)
(Continued)

(52) U.S. Cl.
CPC ...... *G01N 33/6893* (2013.01); *G01N 33/56944* (2013.01); *G01N 2333/315* (2013.01); *G01N 2800/06* (2013.01); *G01N 2800/065* (2013.01); *G01N 2800/56* (2013.01)

(58) Field of Classification Search
None
See application file for complete search history.

(56) References Cited

U.S. PATENT DOCUMENTS

2001/0026922 A1   10/2001   Holland
2009/0041782 A1    2/2009   Ooshima et al.
(Continued)

FOREIGN PATENT DOCUMENTS

JP    2010/233552 A    10/2010
WO   WO 97/43314 A2    11/1997
(Continued)

OTHER PUBLICATIONS

Umemura et al., WO 2010/113627, published Oct. 7, 2010, English translation.*
(Continued)

*Primary Examiner* — Karen Cochrane Carlson
*Assistant Examiner* — Jennifer M. H. Tichy
(74) *Attorney, Agent, or Firm* — Wolf, Greenfield & Sacks, P.C.

(57) ABSTRACT

Disclosed is the construction of a system capable of quickly and easily identifying patients having a risk for worsening inflammatory digestive tract disease by identifying a causal factor for the worsening of the inflammatory digestive tract disease. Specifically disclosed is a method for detecting oral bacteria that cause worsening of inflammatory digestive tract disease and/or a screening that targets high risk for worsening of inflammatory digestive tract disease and/or determining the risk for worsening of the inflammatory digestive tract disease by PA not being detected and/or CBP being detected, inclusive of the detection of PA, which is an oral bacteria protein antigen, and/or CBP, which is collagen binding protein, in samples. Also disclosed are a detection reagent and kit used for this method.

19 Claims, 16 Drawing Sheets

Flow-chart of analyses

Analysis 1: Culture of *S. mutans*
Analysis 2: Detection of *S. mutans*
Analysis 3: Detection of PA-deficient *S. mutans*
Analysis 4: Detection of CBP-carrying *S. mutans*

(51) Int. Cl.
G01N 33/68 (2006.01)
G01N 33/569 (2006.01)

(56) References Cited

U.S. PATENT DOCUMENTS

2010/0286027 A1 11/2010 Parkinson et al.
2012/0028879 A1 2/2012 Umemura et al.

FOREIGN PATENT DOCUMENTS

WO WO 2005/063992 A1 7/2005
WO WO 2009/090168 A1 7/2009
WO WO 2010/113627 A1 10/2010

OTHER PUBLICATIONS

Cornell, Making and Using Antibodies, Available online as early as Oct. 12, 1999, at: www-users.med.cornell.edu/~jawagne/Antibody_Approaches.html.*
Dictionary.com, Aggravation, Accessed Oct. 23, 2015, Online at: dictionary.reference.com/browse/aggravation.*
Nomura et al., Potential high virulence for infective endocarditis in Streptococcus mutans strains with collagen binding proteins but lacking PA expression, Archives of Oral Biology, 58 (2013) pp. 1627-1634.*
Berish et al., Nucleotide sequence of the Fbp gene from Neisseria meningitidis. Nucleic Acids Res. Aug. 11, 1990;18(15):4596.
Holland, Serologic response to Streptococcus mutans in Crohn's disease and ulcerative colitis. Gastroenterology. Apr. 1998;114(1):A997.
Hoshino et al., PCR detection and identification of oral Streptococci in saliva samples using gtf genes. Diagn Microbiol Infect Dis. Mar. 2004;48(3):195-9.
Hoshino et al., Evolution of cariogenic character in Streptococcus mutans: horizontal transmission of glycosyl hydrolase family 70 genes. Sci Rep. 2012;2:518. doi: 10.1038/srep00518. Epub Jul. 18, 2012.
Kawato et al., Effects of antibodies against a fusion protein consisting of parts of cell surface protein antigen and glucosyltransferase of Streptococcus sobrinus on cell adhesion of mutans Streptococci. Oral Microbiol Immunol. Feb. 2008;23(1):14-20. doi: 10.1111/j.1399-302X.2007.00382.x.
Kelly et al., Sequence analysis of the cloned streptococcal cell surface antigen I/II. FEBS Lett. Nov. 20, 1989;258(1):127-32.
Kojima et al., Analyis of mechanism of development of disease state by enteritis-inducing Streptococcus mutans. Japan. J. Ped. Dent. 2011;49(4):380.
Kojima et al., Examination of pathogenicity of Streptococcus mutans in mouse enteritis model. Japan. J. Ped. Dent. 2010:48(2);341.
Kojima et al., Infection of specific strains of Streptococcus mutans, oral bacteria, confers a risk of ulcerative colitis. Sci Rep. 2012;2:332. doi: 10.1038/srep00332. Epub Mar. 26, 2012.
Kojima et al., Analysis of mechanisms of aggravation of enteritis induced by Streptococcus mutans. Japan. J. Ped. Dent. 2012;50(1):106.
Kojima et al., Analysis of role of IFN-γ in aggravation of enteritis caused by Streptococcus mutans. Japan J. Ped.Dent. 2012;50(2):189.

Matsumoto-Nakano et al., Molecular interactions of alanine-rich and proline-rich regions of cell surface protein antigen c in Streptococcus mutans. Oral Microbiol Immunol. Aug. 2008;23(4):265-70. doi: 10.1111/j.1399-302X.2007.00421.x.
Meurman et al., Gingival and dental status, salivary acidogenic bacteria, and yeast counts of patients with active or inactive Crohn's disease. Oral Surg Oral Med Oral Pathol. May 1994;77(5):465-8.
Minami et al., Interaction of structural isomers of sucrose in the reaction between sucrose and glucosyltransferases from mutans Streptococci. Oral Microbiol Immunol. Aug. 1990;5(4):189-94.
Nakano et al., Contribution of cell surface protein antigen PAc of Streptococcus mutans to bacteremia. Microbes Infect. Jan. 2006;8(1):114-21.
Nakano et al., Demonstration of Streptococcus mutans with a cell wall polysaccharide specific to a new serotype, k, in the human oral cavity. J Clin Microbiol. Jan. 2004;42(1):198-202.
Nakano et al., Detection of novel serotype k Streptococcus mutans in infective endocarditis patients. J Med Microbiol. Oct. 2007;56(Pt 10):1413-5.
Nakano et al., Development of a PCR method for rapid identification of new Streptococcus mutans serotype k strains. J Clin Microbiol. Nov. 2004;42(11):4925-30.
Nakano et al., Protein antigen in serotype k Streptococcus mutans clinical isolates. J Dent Res. Oct. 2008;87(10):964-8.
Nakano et al., Streptococcus mutans and cardiovascular diseases. Japanese Dental Sci Rev. Jul. 2008;44(1): 29-37.
Nakano et al., Streptococcus mutans clonal variation revealed by multilocus sequence typing. J Clin Microbiol. Aug. 2007;45(8):2616-25. Epub Jun. 13, 2007.
Nakano, The analysis of virulence factors of cariogenic bacteria in cardiovascular diseases. Official Publication of the Japanese Society of Pediatric Dentistry. 2007;45(2):43.
Nishimura et al., The role of protein antigen c(Pac) in the bacteremia caused by Streptococcus mutans. Official Publication of the Japanese Society of Pediatric Dentistry. 2005;43(2):356.
Nomura et al., Molecular and clinical analyses of the gene encoding the collagen-binding adhesin of Streptococcus mutans. J Med Microbiol. Apr. 2009;58(Pt 4):469-75. doi: 10.1099/jmm.0.007559-0.
Nomura et al., Identification and characterization of a collagen-binding protein, Cbm, in Streptococcus mutans. Mol Oral Microbiol. Aug. 2012;27(4):308-23. doi: 10.1111/j.2041-1014.2012.00649.x. Epub May 2, 2012.
Okahashi et al., Cloning of a surface protein antigen gene from serotype c Streptococcus mutans. Mol Microbiol. Feb. 1989;3(2):221-8.
Sato et al., Streptococcus mutans strains harboring collagen-binding adhesin. J Dent Res. Jul. 2004;83(7):534-9.
Shibata et al., Analysis of loci required for determination of serotype antigenicity in Streptococcus mutans and its clinical utilization. J Clin Microbiol. Sep. 2003;41(9):4107-12.
Sundh et al., Salivary antimicrobial proteins in patients with Crohn's disease. Oral Surg Oral Med Oral Pathol. Nov. 1993;76(5):564-9.
Taniguchi et al., The presences of cmn gene-carrying S. mutants in saliva samples and associated clinical observations. Official Publication of the Japanese Society of Pediatric Dentistry. 2008;46(2):289.

* cited by examiner

Fig.1
Flow-chart of analyses
Analysis 1: Culture of *S. mutans*
Analysis 2: Detection of *S. mutans*
Analysis 3: Detection of PA-deficient *S. mutans*
Analysis 4: Detection of CBP-carrying *S. mutans*
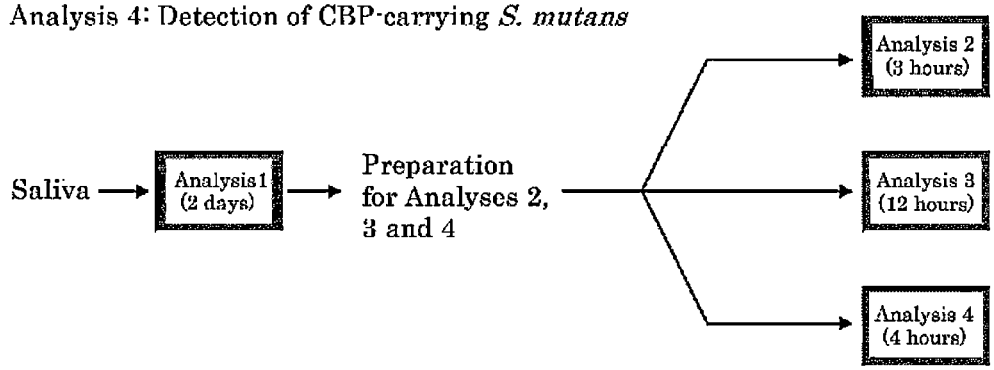
Fig.2  Analytical procedures
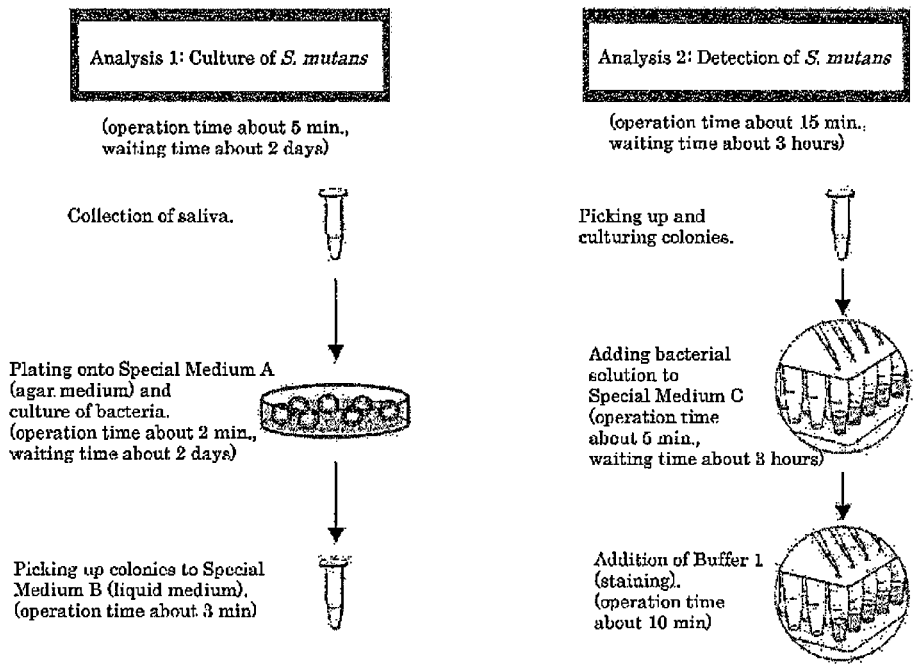

Fig.5
 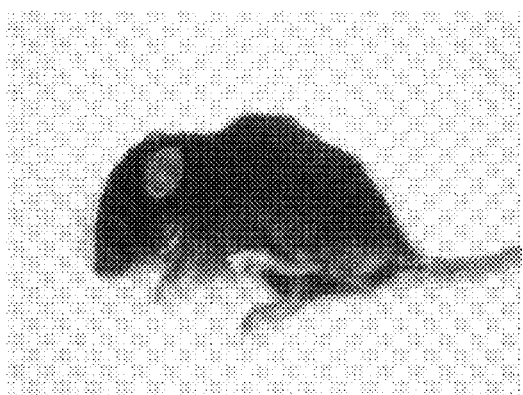
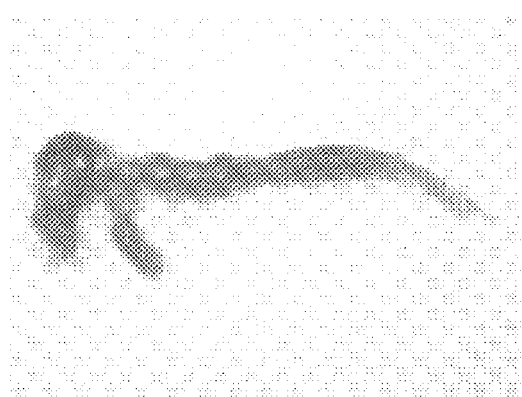 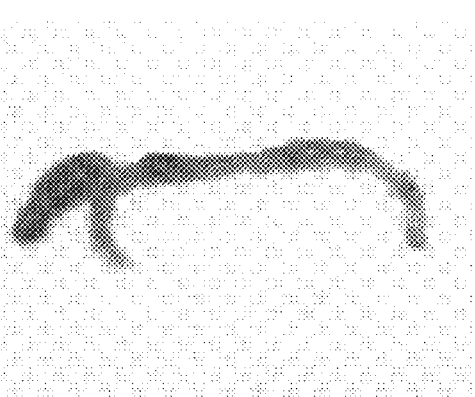
Control　　　　　TW295

Lung          Liver

Fig.11
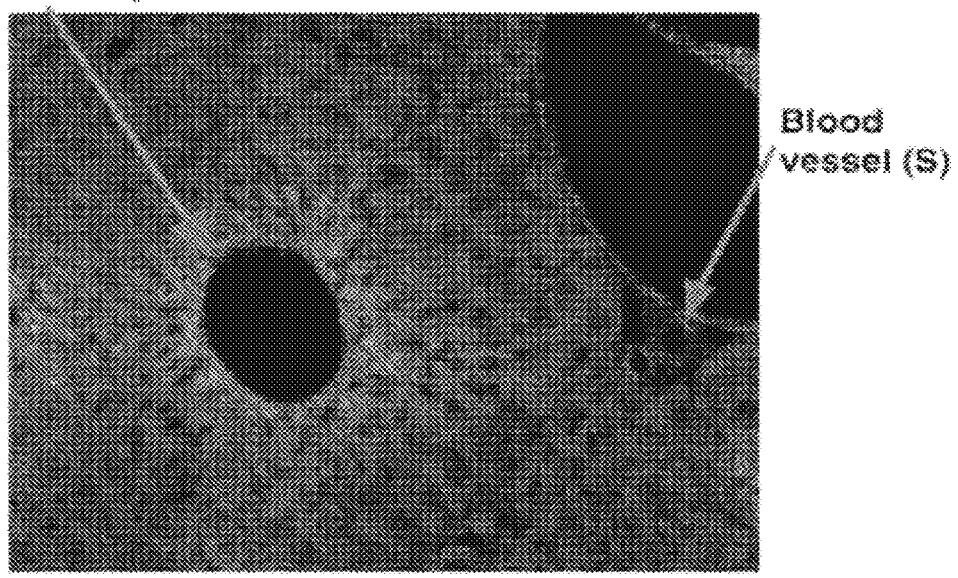
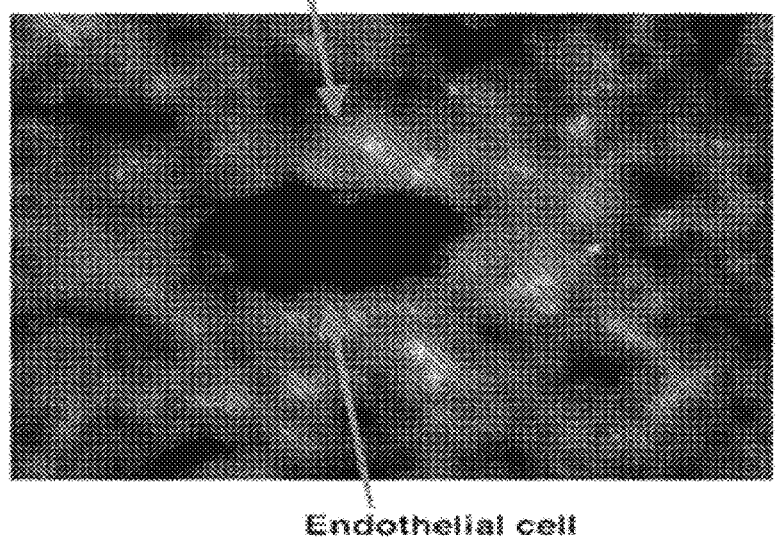

Fig. 14
Consideration of optimal conditions for culturing *S. mutans* in Analysis 1
(a) bacitracin x 1
(b) bacitracin x 5
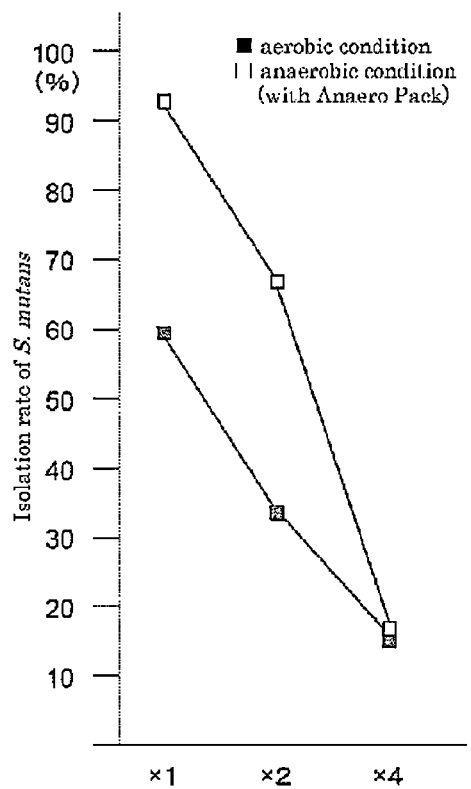
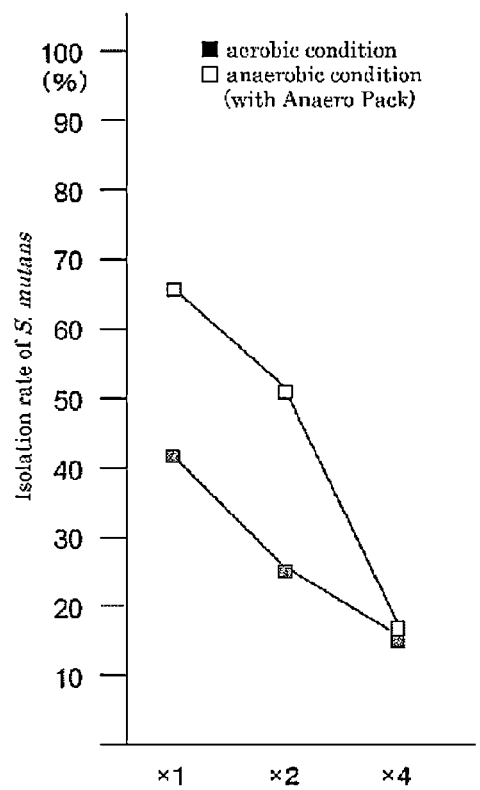
Sucrose (relative amount of sucrose to the sucrose content of a conventional MSB medium)
Sucrose (relative amount of sucrose to the sucrose content of a conventional MSB medium)

Fig. 15 Consideration of possible stock period of saliva sample

Odds ratio: 2.99

SEQUENCE LISTING

```
<160> NUMBER OF SEQ ID NOS: 24

<210> SEQ ID NO 1
<211> LENGTH: 1565
<212> TYPE: PRT
<213> ORGANISM: Streptococcus mutans

<400> SEQUENCE: 1

Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Ala Gln Gly Ser Ala Ser Lys Glu Ala Gln Ser Gln Thr Lys
65                  70                  75                  80

Leu Glu Arg Gln Met Val His Thr Ile Glu Val Pro Lys Thr Asp Leu
                85                  90                  95

Asp Gln Ala Ala Lys Asp Ala Lys Ser Ala Gly Val Asn Val Val Gln
            100                 105                 110

Asp Ala Asp Val Asn Lys Gly Thr Val Lys Thr Pro Glu Glu Ala Val
        115                 120                 125

Gln Lys Glu Thr Glu Ile Lys Glu Asp Tyr Thr Lys Gln Ala Glu Asp
    130                 135                 140

Ile Lys Lys Thr Thr Asp Gln Tyr Lys Ser Asp Val Ala Ala His Glu
145                 150                 155                 160

Ala Glu Val Ala Lys Ile Lys Ala Lys Asn Gln Ala Thr Lys Glu Gln
                165                 170                 175

Tyr Glu Lys Asp Met Ala Ala His Lys Ala Glu Val Glu Arg Ile Asn
            180                 185                 190

Ala Ala Asn Ala Ala Ser Lys Thr Ala Tyr Glu Ala Lys Leu Ala Gln
        195                 200                 205

Tyr Gln Ala Asp Leu Ala Ala Val Gln Lys Thr Asn Ala Ala Asn Gln
    210                 215                 220

Ala Ala Tyr Gln Lys Ala Leu Ala Ala Tyr Gln Ala Glu Leu Lys Arg
225                 230                 235                 240

Val Gln Glu Ala Asn Ala Ala Ala Lys Ala Ala Tyr Asp Thr Ala Val
                245                 250                 255

Ala Ala Asn Asn Ala Lys Asn Thr Glu Ile Ala Ala Ala Asn Glu Glu
            260                 265                 270
```

```
Ile Arg Lys Arg Asn Ala Thr Ala Lys Ala Glu Tyr Glu Thr Lys Leu
        275                 280                 285

Ala Gln Tyr Gln Ala Glu Leu Lys Arg Val Gln Glu Ala Asn Ala Ala
290                 295                 300

Asn Glu Ala Asp Tyr Gln Ala Lys Leu Thr Ala Tyr Gln Thr Glu Leu
305                 310                 315                 320

Ala Arg Val Gln Lys Ala Asn Ala Asp Ala Lys Ala Thr Tyr Glu Ala
                325                 330                 335

Ala Val Ala Ala Asn Asn Ala Lys Asn Ala Ala Leu Thr Ala Glu Asn
                340                 345                 350

Thr Ala Ile Lys Gln Arg Asn Glu Asn Ala Lys Ala Thr Tyr Glu Ala
            355                 360                 365

Ala Leu Lys Gln Tyr Glu Ala Asp Leu Ala Ala Val Lys Lys Ala Asn
            370                 375                 380

Ala Ala Asn Glu Ala Asp Tyr Gln Ala Lys Leu Thr Ala Tyr Gln Thr
385                 390                 395                 400

Glu Leu Ala Arg Val Gln Lys Ala Asn Ala Asp Ala Lys Ala Ala Tyr
                405                 410                 415

Glu Ala Ala Val Ala Ala Asn Asn Ala Ala Asn Ala Ala Leu Thr Ala
                420                 425                 430

Glu Asn Thr Ala Ile Lys Lys Arg Asn Ala Asp Ala Lys Ala Asp Tyr
            435                 440                 445

Glu Ala Lys Leu Ala Lys Tyr Gln Ala Asp Leu Ala Lys Tyr Gln Lys
            450                 455                 460

Asp Leu Ala Asp Tyr Pro Val Lys Leu Lys Tyr Glu Asp Glu Gln
465                 470                 475                 480

Thr Ser Ile Lys Ala Ala Leu Ala Glu Leu Glu Lys His Lys Asn Glu
                485                 490                 495

Asp Gly Asn Leu Thr Glu Pro Ser Ala Gln Asn Leu Val Tyr Asp Leu
                500                 505                 510

Glu Pro Asn Ala Asn Leu Ser Leu Thr Thr Asp Gly Lys Phe Leu Lys
            515                 520                 525

Ala Ser Ala Val Asp Asp Ala Phe Ser Lys Ser Thr Ser Lys Ala Lys
            530                 535                 540

Tyr Asp Gln Lys Ile Leu Gln Leu Asp Asp Leu Asp Ile Thr Asn Leu
545                 550                 555                 560

Glu Gln Ser Asn Asp Val Ala Ser Ser Met Glu Leu Tyr Gly Asn Phe
                565                 570                 575

Gly Asp Lys Ala Gly Trp Ser Thr Thr Val Ser Asn Ser Gln Val
                580                 585                 590

Lys Trp Gly Ser Val Leu Leu Glu Arg Gly Gln Ser Ala Thr Ala Thr
            595                 600                 605

Tyr Thr Asn Leu Gln Asn Ser Tyr Tyr Asn Gly Lys Lys Ile Ser Lys
            610                 615                 620

Ile Val Tyr Lys Tyr Thr Val Asp Pro Lys Ser Lys Phe Gln Gly Gln
625                 630                 635                 640

Lys Val Trp Leu Gly Ile Phe Thr Asp Pro Thr Leu Gly Val Phe Ala
                645                 650                 655

Ser Ala Tyr Thr Gly Gln Val Glu Lys Asn Thr Ser Ile Phe Ile Lys
                660                 665                 670

Asn Glu Phe Thr Phe Tyr His Glu Asp Glu Lys Pro Ile Asn Phe Asp
            675                 680                 685
```

-continued

Asn Ala Leu Leu Ser Val Thr Ser Leu Asn Arg Glu His Asn Ser Ile
690                 695                 700

Glu Met Ala Lys Asp Tyr Ser Gly Lys Phe Val Lys Ile Ser Gly Ser
705                 710                 715                 720

Ser Ile Gly Glu Lys Asn Gly Met Ile Tyr Ala Thr Asp Thr Leu Asn
            725                 730                 735

Phe Lys Gln Gly Glu Gly Gly Ser Arg Trp Thr Met Tyr Lys Asn Ser
            740                 745                 750

Gln Ala Gly Ser Gly Trp Asp Ser Asp Ala Pro Asn Ser Trp Tyr
            755                 760                 765

Gly Ala Gly Ala Ile Lys Met Ser Gly Pro Asn Asn His Val Thr Val
770                 775                 780

Gly Ala Thr Ser Ala Thr Asn Val Met Pro Val Ser Asp Met Pro Val
785                 790                 795                 800

Val Pro Gly Lys Asp Asn Thr Asp Gly Lys Lys Pro Asn Ile Trp Tyr
            805                 810                 815

Ser Leu Asn Gly Lys Ile Arg Ala Val Asn Val Pro Lys Val Thr Lys
            820                 825                 830

Glu Lys Pro Thr Pro Pro Val Lys Pro Thr Ala Pro Thr Lys Pro Thr
            835                 840                 845

Tyr Glu Thr Glu Lys Pro Leu Lys Pro Ala Pro Val Ala Pro Asn Tyr
850                 855                 860

Glu Lys Glu Pro Thr Pro Pro Thr Arg Thr Pro Asp Gln Ala Glu Pro
865                 870                 875                 880

Asn Lys Pro Thr Pro Pro Thr Tyr Glu Thr Glu Lys Pro Leu Glu Pro
            885                 890                 895

Ala Pro Val Glu Pro Ser Tyr Glu Ala Glu Pro Thr Pro Pro Thr Arg
            900                 905                 910

Thr Pro Asp Gln Ala Glu Pro Asn Lys Pro Thr Pro Pro Thr Tyr Glu
            915                 920                 925

Thr Glu Lys Pro Leu Glu Pro Ala Pro Val Glu Pro Ser Tyr Glu Ala
            930                 935                 940

Glu Pro Thr Pro Pro Thr Pro Thr Pro Asp Gln Pro Glu Pro Asn Lys
945                 950                 955                 960

Pro Val Glu Pro Thr Tyr Glu Val Ile Pro Thr Pro Pro Thr Asp Pro
            965                 970                 975

Val Tyr Gln Asp Leu Pro Thr Pro Pro Ser Asp Pro Thr Val His Phe
            980                 985                 990

His Tyr Phe Lys Leu Ala Val Gln Pro Gln Val Asn Lys Glu Ile Arg
            995                 1000                1005

Asn Asn Asp Ile Asn Ile Asp Arg Thr Leu Val Ala Lys Gln
    1010                1015                1020

Ser Val Val Lys Phe Gln Leu Lys Thr Ala Asp Leu Pro Ala Gly
    1025                1030                1035

Arg Asp Glu Thr Thr Ser Phe Val Leu Val Asp Pro Leu Pro Ser
    1040                1045                1050

Gly Tyr Gln Phe Asn Pro Glu Ala Thr Lys Ala Ala Ser Pro Gly
    1055                1060                1065

Phe Asp Val Thr Tyr Asp Asn Ala Thr Asn Thr Val Thr Phe Lys
    1070                1075                1080

Ala Thr Ala Ala Thr Leu Ala Thr Phe Asn Ala Asp Leu Thr Lys
    1085                1090                1095

Ser Val Ala Thr Ile Tyr Pro Thr Val Val Gly Gln Val Leu Asn

```
            1100                1105                1110

Asp Gly Ala Thr Tyr Lys Asn Asn Phe Thr Leu Thr Val Asn Asp
            1115                1120                1125

Ala Tyr Gly Ile Lys Ser Asn Val Val Arg Val Thr Thr Pro Gly
            1130                1135                1140

Lys Pro Asn Asp Pro Asp Asn Pro Asn Asn Tyr Ile Lys Pro
            1145                1150                1155

Thr Lys Val Asn Lys Asn Glu Asn Gly Val Val Ile Asp Gly Lys
            1160                1165                1170

Thr Val Leu Ala Gly Ser Thr Asn Tyr Tyr Glu Leu Thr Trp Asp
            1175                1180                1185

Leu Asp Gln Tyr Lys Asn Asp Arg Ser Ser Ala Asp Thr Ile Gln
            1190                1195                1200

Lys Gly Phe Tyr Tyr Val Asp Asp Tyr Pro Glu Glu Ala Leu Glu
            1205                1210                1215

Leu Arg Gln Asp Leu Val Lys Ile Thr Asp Ala Asn Gly Asn Glu
            1220                1225                1230

Val Thr Gly Val Ser Val Asp Asn Tyr Thr Asn Leu Glu Ala Ala
            1235                1240                1245

Pro Gln Glu Ile Arg Asp Val Leu Ser Lys Ala Gly Ile Arg Pro
            1250                1255                1260

Lys Gly Ala Phe Gln Ile Phe Arg Ala Asp Asn Pro Arg Glu Phe
            1265                1270                1275

Tyr Asp Thr Tyr Val Lys Thr Gly Ile Asp Leu Lys Ile Val Ser
            1280                1285                1290

Pro Met Val Val Lys Lys Gln Met Gly Gln Thr Gly Gly Ser Tyr
            1295                1300                1305

Glu Asn Gln Ala Tyr Gln Ile Asp Phe Gly Asn Gly Tyr Ala Ser
            1310                1315                1320

Asn Ile Val Ile Asn Asn Val Pro Lys Ile Asn Pro Lys Lys Asp
            1325                1330                1335

Val Thr Leu Thr Leu Asp Pro Ala Asp Thr Asn Asn Val Asp Gly
            1340                1345                1350

Gln Thr Ile Pro Leu Asn Thr Val Phe Asn Tyr Arg Leu Ile Gly
            1355                1360                1365

Gly Ile Ile Pro Ala Asn His Ser Glu Glu Leu Phe Glu Tyr Asn
            1370                1375                1380

Phe Tyr Asp Asp Tyr Asp Gln Thr Gly Asp His Tyr Thr Gly Gln
            1385                1390                1395

Tyr Lys Val Phe Ala Lys Val Asp Ile Thr Leu Lys Asn Gly Val
            1400                1405                1410

Ile Ile Lys Ser Gly Thr Glu Leu Thr Gln Tyr Thr Thr Ala Glu
            1415                1420                1425

Val Asp Thr Thr Lys Gly Ala Ile Thr Ile Lys Phe Lys Glu Ala
            1430                1435                1440

Phe Leu Arg Ser Val Ser Ile Asp Ser Ala Phe Gln Ala Glu Ser
            1445                1450                1455

Tyr Ile Gln Met Lys Arg Ile Ala Val Gly Thr Phe Glu Asn Thr
            1460                1465                1470

Tyr Ile Asn Thr Val Asn Gly Val Thr Tyr Ser Ser Asn Thr Val
            1475                1480                1485

Lys Thr Thr Thr Pro Glu Asp Pro Ala Asp Pro Thr Asp Pro Gln
            1490                1495                1500
```

Asp Pro Ser Ser Pro Arg Thr Ser Thr Val Ile Ile Tyr Lys Pro
1505                 1510                1515

Gln Ser Thr Ala Tyr Gln Pro Ser Ser Val Gln Glu Thr Leu Pro
1520                 1525                1530

Asn Thr Gly Val Thr Asn Asn Ala Tyr Met Pro Leu Leu Gly Ile
1535                 1540                1545

Ile Gly Leu Val Thr Ser Phe Ser Leu Leu Gly Leu Lys Ala Lys
1550                 1555                1560

Lys Asp
1565

<210> SEQ ID NO 2
<211> LENGTH: 4698
<212> TYPE: DNA
<213> ORGANISM: Streptococcus mutans

<400> SEQUENCE: 2

```
atgaaagtca aaaaaactta cggttttcgt aaaagtaaaa ttagtaaaac actgtgtggt      60
gctgttctag aacagtagc agcagtctct gtagcaggac aaaaggtttt tgccgatgaa     120
acgaccacta ctagtgatgt agatactaaa gtagttggaa cacaaactgg aaatccagcg     180
accaatttgc cagaggctca agggagtgcg agtaaggaag ctgaacaaag tcaaaccaag     240
ctggagagac aaatggttca taccattgaa gtacctaaaa ctgatcttga tcaagcagca     300
aaagatgcta agtctgctgg tgtcaatgtt gtccaagatg ccgatgttaa taaaggaact     360
gttaaaacac ctgaagaagc agtccaaaaa gaaactgaaa ttaaagaaga ttacacaaaa     420
caagctgagg atattaagaa gacaacagat caatataaat cggatgtagc tgctcatgag     480
gcagaagttg ctaaaatcaa agctaaaaat caggcaacta agaacagta tgaaaaagat     540
atggcagctc ataaagccga ggttgaacgc attaatgctg caaatgctgc cagtaaaaca     600
gcttatgaag ctaaattggc tcaatatcaa gcagatttag cagccgttca aaaaaccaat     660
gctgccaatc aagcagccta tcaaaaagcc cttgctgctt atcaggctga actgaaacgt     720
gttcaggaag ctaatgcagc cgccaaagcc gcttatgata ctgctgtagc agcaaataat     780
gccaaaaata cagaaattgc cgctgccaat gaagaaatta gaaaacgcaa tgcaacggcc     840
aaagctgaat atgagactaa gttagctcaa tatcaagctg aactaaagcg tgttcaggaa     900
gctaatgccg caaacgaagc agactatcaa gctaaattga ccgcctatca aacagagctt     960
gctcgtgttc aaaaagccaa tgcggatgct aaagcgacct atgaagcagc tgtagcagca    1020
aataatgcca aaaatgcggc actcacagct gaaaatactg caattaagca acgcaatgag    1080
aatgctaagg cgacttatga agctgcactc aagcaatatg aggccgattt ggcagcggtg    1140
aaaaaagcta atgccgcaaa cgaagcagac tatcaagcta aattgaccgc ctatcaaaca    1200
gagctcgctc gcgttcaaaa agccaatgcg gatgctaaag cggcctatga agcagctgta    1260
gcagcaaata tgccgcaaa tgcagcgctc acagctgaaa atactgcaat taagaagcgc    1320
aatgcggatg ctaaagctga ttacgaagca aaacttgcta gtatcaagc agatcttgcc    1380
aaatatcaaa aagatttagc agactatcca gttaagttaa aggcatacga agatgaacaa    1440
acttctatta aagctgcact ggcagaactt gaaaaacata aaaatgaaga cggaaactta    1500
acagaaccat ctgctcaaaa tttggtctat gatcttgagc caaatgcgaa cttatctttg    1560
acaacagatg ggaagttcct taaggcttct gctgtggatg atgcttttag caaaagcact    1620
tcaaaagcaa aatatgacca aaaaattctt caattagatg atctagatat cactaactta    1680
```

```
gaacaatcta atgatgttgc ttcttctatg gagctttatg ggaattttgg tgataaagct    1740
ggctggtcaa cgacagtaag caataactca caggttaaat ggggatcggt acttttagag    1800
cgcggtcaaa gcgcaacagc tacatacact aacctgcaga attcttatta caatggtaaa    1860
aagatttcta aaattgtcta caagtataca gtggaccctg agtccaagtt tcaaggtcaa    1920
aaggtttggt taggtatttt taccgatcca actttaggtg ttttttgcttc tgcttataca    1980 ggtcaagttg aaaaaaacac ttctattttt attaaaaatg aattcacttt ctatcacgaa    2040
gatgaaaaac caattaattt tgataatgcc cttctctcag tgacttctct taaccgtgaa    2100
cataactcta ttgagatggc taaagattat agtggtaaat ttgtcaaaat ctctggttca    2160
tctattggtg aaaagaatgg catgatttat gctacagata ctcttaactt aaacagggt    2220 gaaggtggct ctcgctggac tatgtataaa aatagtcaag ctggttcagg atgggatagt    2280
tcagatgcgc cgaattcttg gtatggagca ggggctatta aaatgtctgg tccgaataac    2340
catgttactg taggagcaac ttctgcaaca aatgtaatgc cagtttctga catgcctgtt    2400
gttcctggta aggacaatac tgatggcaaa aaaccaaata tttggtattc tttaaatggt    2460
aaaatccgtg cggttaatgt tcctaaagtt actaaggaaa aacccacacc tccggttaaa    2520
ccaacagctc caactaaacc aacttatgaa acagaaaagc cattaaaacc ggcaccagta    2580
gctccaaatt atgaaaagga gccaacaccg ccgacaagga caccggatca agcagagcca    2640
aacaaaccca caccgccgac ctatgaaaca gaaaagccgt tggagccagc acctgttgag    2700
ccaagctatg aagcagagcc aacaccgccg acaaggacac cggatcaggc agagccaaat    2760
aaacccacac cgccgaccta tgaaacagaa aagccgttgg agccagcacc tgttgagcca    2820
agctatgaag cagagccaac gccaccgaca ccaacaccag atcaaccaga accaaacaaa    2880
cctgttgagc caacttatga ggttattcca acaccgccga ctgatcctgt ttatcaagat    2940
cttccaacac ctccatctga tccaactgtt catttccatt actttaaact agctgttcag    3000
ccgcaggtta acaaagaaat tagaaacaat aacgatatta atattgacag aacttttggtg    3060 gctaaacaat ctgttgttaa gttccagctg aagacagcag atctccctgc tggacgtgat    3120
gaaaccactt cctttgtctt ggtagatccc ctgccatctg gttatcaatt taatcctgaa    3180
gctacaaaag ctgcaagccc tggctttgat gtcacttatg ataatgcaac taatacagtc    3240
accttcaagg caactgcagc aactttggct acgtttaatg ctgatttgac taagtcagtg    3300
gcaacgattt atccaacagt ggtcggacaa gttcttaatg atggcgcaac ttataagaat    3360
aatttcacgc tcacagtcaa tgatgcttat ggcattaaat ccaatgttgt tcgggtgaca    3420
actcctggta aaccaaatga tccagataat ccaaataata attatattaa accaactaag    3480
gttaataaaa acgaaaatgg cgttgttatt gatggtaaaa cagttcttgc cggttcaacg    3540
aattattatg agctaacttg ggatttggat caatataaaa acgaccgctc ttcagcagat    3600
accattcaaa aaggatttta ctatgtagat gattatccag aagaagcgct tgaattgcgt    3660
caggatttag tgaagattac agatgctaat ggtaatgaag ttactggtgt tagtgtggat    3720
aattatacta atcttgaagc agcccctcaa gaaattagag atgttctttc taaggcagga    3780
attagaccta aaggtgcttt ccaaattttc cgtgccgata atccaagaga attttatgat    3840
acttatgtca aaactggaat tgatttgaag attgtatcac caatggttgt taaaaaacaa    3900
atgggacaaa caggcggcag ttatgaaaat caagcttacc aaattgactt tggtaatggt    3960
tatgcatcaa atatcgttat caataatgtt cctaagatta accctaagaa agatgtgacc    4020
```

-continued

```
ttaacacttg atccggctga tacaaataat gttgatggtc agactattcc acttaataca    4080
gtctttaatt accgtttgat tggtggcatt atccctgcaa atcactcaga agaactcttt    4140
gaatacaatt tctatgatga ttatgatcaa acaggagatc actatactgg tcagtataaa    4200
gttttttgcca aggttgatat cactcttaaa acggtgtta ttatcaagtc aggtactgag    4260
ttaactcagt atacgacagc ggaagttgat accactaaag gtgctatcac aattaagttc    4320
aaggaagcct ttctgcgttc tgtttcaatt gattcagcct tccaagctga agttatatc    4380
caaatgaaac gtattgcggt tggtactttt gaaaatacct atattaatac tgtcaatggg    4440
gtaacttaca gttcaaatac agtgaaaaca actactcctg aggatcctgc agaccctact    4500
gatccgcaag atccatcatc accgcggact tcaactgtaa ttatctacaa acctcaatca    4560
actgcttatc agccaagctc tgttcaagaa acattaccaa atacgggagt aacaaacaat    4620
gcttatatgc ctttacttgg tattattggc ttagttacta gttttagttt gcttggttta    4680
aaggctaaga aagattga                                                  4698
```

<210> SEQ ID NO 3
<211> LENGTH: 555
<212> TYPE: PRT
<213> ORGANISM: Streptococcus mutans
<400> SEQUENCE: 3

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255
```

-continued

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
            325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Thr Glu Ala Pro Thr Thr Thr Glu
            355                 360                 365

Ala Pro Thr Thr Thr Glu Ala Pro Thr Thr Thr Glu Ala Pro Thr Thr
370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
            405                 410                 415

Ala Pro Thr Thr Thr Glu Ala Pro Thr Thr Thr Glu Ala Pro Thr Thr
            420                 425                 430

Thr Glu Ala Pro Thr Thr Thr Glu Ala Pro Thr Thr Thr Glu Ala Pro
            435                 440                 445

Thr Thr Thr Glu Ala Pro Thr Thr Thr Glu Ala Pro Thr Thr Thr Glu
            450                 455                 460

Ala Pro Thr Thr Thr Glu Ala Pro Thr Thr Thr Glu Val Ser Ser Glu
465                 470                 475                 480

Thr Thr Lys Ala Glu Glu Thr Thr Thr Lys Val Lys Glu Pro Glu Lys
            485                 490                 495

Thr Thr Thr Ser Val Pro Ala Gly Thr Thr Ser Asn Lys Pro Asn Lys
            500                 505                 510

Pro Ser Gly Lys Gln Gly Ala Gly Thr Lys Gly Leu Pro Ser Thr Gly
            515                 520                 525

Glu Glu Ser Gly Ile Val Leu Ser Leu Leu Gly Leu Ala Thr Val Ser
            530                 535                 540

Val Thr Gly Leu Val Tyr Arg Lys Tyr His Ser
545                 550                 555

<210> SEQ ID NO 4
<211> LENGTH: 1668
<212> TYPE: DNA
<213> ORGANISM: Streptococcus mutans

<400> SEQUENCE: 4
atgaaaagaa aaggtttacg aagactatta aagttttttg gaaccgttgc catcattttg      60
ccaatgtttt tcatagcttt aacgaaagct caggcaagtg atgtcagcag taacatttca     120
tcgctgacgg tatcaccgac tcagattaat gatggcggta agaccaccgt tcgctttgag     180
tttgatgagc atgctcaaaa tattaaagca ggcgacacca ttactgttaa ctggcagaat     240
tcaggaacag tcagaggaac aggttatacg aaaaccatta agctggaggt tcagggcaag     300
tatgttggtg atttggtagt tacgcaagac aaagcagttg ttactttcaa tgacagtatt     360
actggcttgc agaatatcac cggctgggt gaatttgaaa tcgaaggccg gaattttact     420

-continued

```
gacactacta ccggaaatac tggcagcttc caagttacca gcggcggcaa gacagctgag      480
gttactgtcg ttaaatctgc ttcagggact accggcgttt tctactataa gactggggat      540
atgcagacag atgacaccaa tcatgtgcgc tggttttgga atatcaacaa tgagaatgct      600
tatgtagaca gtgatattcg tattgaagat gacattcagt ctggtcaaac tttggatata      660
gacagttttg atattactgt aaatggcagt gagtcttatc gcggtcaaga aggtattaat      720
cagcttgccc aaagatatgg tgcaactatt tcagctgatc cggctagtgg ccatatcagt      780
gtttatattc ctcaaggcta tgcttctttg aatcgcttta gcatcatgta cttgactaaa      840
gttgacaatc ctgatcaaaa gacgtttgaa aataacagta aggcttggta taaggaaaac      900
ggtaaagatg ctgttgatgg taaggaattt aaccattctg tagctaatgt taatgccgcc      960
ggcggtgtgg acgaagaac aaccactact acagaaaagc caacaacgac acagagggct     1020
ccaacaacaa cggaaactcc aacgacaaca gaggctccaa caacggaagc tccaacgaca     1080
acagaggctc caacgacaac agaggctcca acaacaacgg aagctccaac gacaacagaa     1140
gctccaacaa caacggaagc tccaacgaca acagaggctc caacgacaac agaggctcca     1200
acaacaacgg aagctccaac gacaacagag gctccaacaa caacggaagc tccaacgaca     1260
acagaagctc caacaacaac ggaagctcca acgacaacag aggctccaac aacaacggaa     1320
gctccaacga acagaggc tccaacaaca acggaagctc caacgacaac agaggctcca     1380
acaacaacgg aagctccaac aacaacggaa gctccaacaa caacggaagt atcttcagaa     1440
acaactaaag ctgaagaaac aactactaaa gttaaggaac cagaaaaaac aacgacatca     1500
gttccagcag gtacaacttc aaacaaacct aataagccat caggcaaaca aggtgctggt     1560
accaagggac ttccaagcac aggcgaagaa agcggtattg ttttgtcact tctcggtctt     1620
gcaactgtct cagtgactgg tctagtttac cgtaaatatc atagctga                  1668
```

<210> SEQ ID NO 5
<211> LENGTH: 165
<212> TYPE: PRT
<213> ORGANISM: Streptococcus mutans

<400> SEQUENCE: 5

| Val | Thr | Ser | Gly | Gly | Lys | Thr | Ala | Glu | Val | Thr | Val | Lys | Ser | Ala |
|---|---|---|---|---|---|---|---|---|---|---|---|---|---|---|
| 1 | | | | 5 | | | | | 10 | | | | | 15 |

| Ser | Gly | Thr | Thr | Gly | Val | Phe | Tyr | Tyr | Lys | Thr | Gly | Asp | Met | Gln | Thr |
|---|---|---|---|---|---|---|---|---|---|---|---|---|---|---|---|
| | | | 20 | | | | | 25 | | | | | 30 | | |

Asp Asp Thr Asn His Val Arg Trp Phe Leu Asn Ile Asn Asn Glu Asn
            35                  40                  45

Ala Tyr Val Asp Ser Asp Ile Arg Ile Glu Asp Ile Gln Ser Gly
        50                  55                  60

Gln Thr Leu Asp Ile Asp Ser Phe Asp Ile Thr Val Asn Gly Ser Glu
65                  70                  75                  80

Ser Tyr Arg Gly Gln Glu Gly Ile Asn Gln Leu Ala Gln Arg Tyr Gly
                85                  90                  95

Ala Thr Ile Ser Ala Asp Pro Ala Ser Gly His Ile Ser Val Tyr Ile
            100                 105                 110

Pro Gln Gly Tyr Ala Ser Leu Asn Arg Phe Ser Ile Met Tyr Leu Thr
        115                 120                 125

Lys Val Asp Asn Pro Asp Gln Lys Thr Phe Glu Asn Asn Ser Lys Ala
    130                 135                 140

Trp Tyr Lys Glu Asn Gly Lys Asp Ala Val Asp Gly Lys Glu Phe Asn

His Ser Val Ala Asn
                165

<210> SEQ ID NO 6
<211> LENGTH: 495
<212> TYPE: DNA
<213> ORGANISM: Streptococcus mutans

<400> SEQUENCE: 6
gttaccagcg gcggcaagac agctgaggtt actgtcgtta atctgcttc agggactacc      60
ggcgttttct actataagac tggggatatg cagacagatg acaccaatca tgtgcgctgg    120
tttttgaata tcaacaatga gaatgcttat gtagacagtg atattcgtat tgaagatgac    180
attcagtctg gtcaaacttt ggatatagac agttttgata ttactgtaaa tggcagtgag    240
tcttatcacg gtcaagaagg tattaatcag cttgcccaaa gatatggtgc aactatttca    300
gctgatccgg ctagtggcca tatcagtgtt tatattcctc aaggctatgc ttctttgaat    360
cgctttagca tcatgtactt gactaaagtt gacaatcctg atcaaaagac gtttgaaaat    420
aacagtaagg cttggtataa ggaaaacggt aaagatgctg ttgatggtaa ggaatttaac    480
cattctgtag ctaat                                                    495

<210> SEQ ID NO 7
<211> LENGTH: 549
<212> TYPE: PRT
<213> ORGANISM: Streptococcus mutans

<400> SEQUENCE: 7

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Ser Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp

```
              210                 215                 220
Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Asn Ser Val Tyr Ile Pro Gln Gly Tyr Ala Ser Leu Asn Arg
                260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
                340                 345                 350

Pro Thr Thr Glu Ala Pro Thr Thr Thr Glu Ala Pro Thr Thr Thr Glu
            355                 360                 365

Ala Pro Thr Thr Thr Glu Ala Pro Thr Thr Thr Glu Ala Pro Thr Thr
        370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
                405                 410                 415

Ala Pro Thr Thr Thr Glu Ala Pro Thr Thr Thr Glu Ala Pro Thr Thr
                420                 425                 430

Thr Glu Ala Pro Thr Thr Thr Glu Ala Pro Thr Thr Thr Glu Ala Pro
            435                 440                 445

Thr Thr Thr Glu Ala Pro Thr Thr Glu Ala Pro Thr Thr Thr Glu
        450                 455                 460

Ala Pro Thr Thr Thr Glu Val Ser Ser Glu Thr Thr Lys Ala Glu Glu
465                 470                 475                 480

Thr Thr Thr Lys Val Lys Glu Pro Glu Lys Thr Thr Ser Val Pro
                485                 490                 495

Ala Gly Thr Thr Ser Asn Lys Pro Asn Lys Pro Ser Gly Lys Gln Gly
                500                 505                 510

Ala Gly Thr Lys Gly Leu Pro Ser Thr Gly Glu Glu Ser Gly Ile Val
            515                 520                 525

Leu Ser Leu Leu Gly Leu Ala Thr Val Ser Val Thr Gly Leu Val Tyr
        530                 535                 540

Arg Lys Tyr His Ser
545

<210> SEQ ID NO 8
<211> LENGTH: 1650
<212> TYPE: DNA
<213> ORGANISM: Streptococcus mutans

<400> SEQUENCE: 8
atgaaaagaa aaggtttacg aagactatta aagttttttg gaaccgttgc catcattttg      60
ccaatgtttt tcatagcttt aacgaaagct caggcaagtg atgtcagcag taacatttca     120
tcgctgacgg tatcaccgac tcagattaat gatggcggta agaccaccgt tcgctttgag     180
```

```
tttgatgagc atgctcaaaa tattaaagca ggcgacacca ttactgttaa ctggcagaat    240
tcaggaacag tcagaggaac aggttatacg aaaaccatta agctggaggt tcagggcaag    300
tatgttggtg atttggtagt tacgcaagac aaagcagttg ttactttcaa tgacagtatt    360
actggcttgc agaatatcac cggctggggt gaatttgaaa tcgaaggccg gaattttact    420
gacactacta ccggaagtac tggcagcttc aagttacca gcggcggcaa gacagctgag    480
gttactgtcg ttaaatctgc ttcagggact accggcgttt tctactataa gactggggat    540
atgcagacag atgacaccaa tcatgtgcgc tggttttga atatcaacaa tgagaatgct    600
tatgtagaca gtgatattcg tattgaagat gacattcagt ctggtcaaac tttggatata    660
gacagttttg atattactgt aaatggcagt gagtcttatc acggtcaaga aggtattaat    720
cagcttgccc aaagatatgg tgcaactatt tcagctgatc cggctagtgg ccataacagt    780
gtttatattc ctcaaggcta tgcttctttg aatcgcttta gcatcatgta cttgactaaa    840
gttgacaatc ctgatcaaaa gacgtttgaa ataacagta aggcttggta taaggaaaac    900
ggtaaagatg ctgttgatgg taaggaattt aaccattctg tagctaatgt taatgccgcc    960
ggcggtgtgg acggaagaac aaccactact acagaaaagc aacaacgac gacagaggct   1020 ccaacaacaa cggaaactcc aacgacaaca gaggctccaa caacggaagc tccaacgaca   1080
acagaggctc caacaacaac ggaagctcca acgacaacag aagctccaac aacaacggaa   1140
gctccaacga caacagaggc tccaacaaca acggaagctc caacgacaac agaagctcca   1200
acaacaacgg aagctccaac gacaacagag ctccaacaa caacggaagc tccaacgaca   1260
acagaagctc caacgacaac agaggctcca acgacaacag aagctccaac aacaacggaa   1320
gctccaacga acagaggc tccaacaaca acggaagctc caacgacaac agaggctcca   1380
acaacaacgg aagctccaac aacaacggaa gtatcttcag aaacaactaa agctgaagaa   1440
acaactacta agttaaggaa accagaaaaa acaacgacat cagttccagc aggtacaact   1500
tcaaacaaac ctaataagcc atcaggcaaa caaggtgctg gtaccaaggg acttccaagc   1560
acaggcgaag aaagcggtat tgttttgtca cttctcggtc ttgcaactgt ctcagtgact   1620
ggtctagttt accgtaaata tcatagctga                                   1650
```

<210> SEQ ID NO 9
<211> LENGTH: 165
<212> TYPE: PRT
<213> ORGANISM: Streptococcus mutans

<400> SEQUENCE: 9

Val Thr Ser Gly Gly Lys Thr Ala Glu Val Thr Val Lys Ser Ala
1               5                   10                  15

Ser Gly Thr Thr Gly Val Phe Tyr Tyr Lys Thr Gly Asp Met Gln Thr
            20                  25                  30

Asp Asp Thr Asn His Val Arg Trp Phe Leu Asn Ile Asn Asn Glu Asn
        35                  40                  45

Ala Tyr Val Asp Ser Asp Ile Arg Ile Glu Asp Asp Ile Gln Ser Gly
    50                  55                  60

Gln Thr Leu Asp Ile Asp Ser Phe Asp Ile Thr Val Asn Gly Ser Glu
65                  70                  75                  80

Ser Tyr Arg Gly Gln Glu Gly Ile Asn Gln Leu Ala Gln Arg Tyr Gly
                85                  90                  95

Ala Thr Ile Ser Ala Asp Pro Ala Ser Gly His Asn Ser Val Tyr Ile
            100                 105                 110

```
Pro Gln Gly Tyr Ala Ser Leu Asn Arg Phe Ser Ile Met Tyr Leu Thr
            115                 120                 125

Lys Val Asp Asn Pro Asp Gln Lys Thr Phe Glu Asn Asn Ser Lys Ala
130                 135                 140

Trp Tyr Lys Glu Asn Gly Lys Asp Ala Val Asp Gly Lys Glu Phe Asn
145                 150                 155                 160

His Ser Val Ala Asn
            165

<210> SEQ ID NO 10
<211> LENGTH: 495
<212> TYPE: DNA
<213> ORGANISM: Streptococcus mutans

<400> SEQUENCE: 10
gttaccagcg gcggcaagac agctgaggtt actgtcgtta atctgcttc agggactacc       60 ggcgttttct actataagac tggggatatg cagacagatg acaccaatca tgtgcgctgg     120
tttttgaata tcaacaatga gaatgcttat gtagacagtt atattcgtat tgaagatgac     180
attcagtctg gtcaaacttt ggatatagac agttttgata ttactgtaaa tggcagtgag     240
tcttatcacg gtcaagaagg tattaatcag cttgcccaaa gatatggtgc aactatttca     300
gctgatccgg ctagtggcca taacagtgtt tatattcctc aaggctatgc ttctttgaat     360
cgctttagca tcatgtactt gactaaagtt gacaatcctg atcaaaagac gtttgaaaat     420
aacagtaagg cttggtataa ggaaaacggt aaagatgctg ttgatggtaa ggaatttaac     480
cattctgtag ctaat                                                      495

<210> SEQ ID NO 11
<211> LENGTH: 27
<212> TYPE: DNA
<213> ORGANISM: Artificial
<220> FEATURE:
<223> OTHER INFORMATION: S.mutans specific primer F

<400> SEQUENCE: 11
ggcaccacaa cattgggaag ctcagtt                                          27

<210> SEQ ID NO 12
<211> LENGTH: 25
<212> TYPE: DNA
<213> ORGANISM: Artificial
<220> FEATURE:
<223> OTHER INFORMATION: S.mutans specific primer R

<400> SEQUENCE: 12
ggaatggccg ctaagtcaac aggat                                            25

<210> SEQ ID NO 13
<211> LENGTH: 20
<212> TYPE: DNA
<213> ORGANISM: Artificial
<220> FEATURE:
<223> OTHER INFORMATION: S.mutans CBP primer (cnm1F)

<400> SEQUENCE: 13
gacaaagaaa tgaaagatgt                                                  20

<210> SEQ ID NO 14
<211> LENGTH: 20
<212> TYPE: DNA
<213> ORGANISM: Artificial
```

```
<220> FEATURE:
<223> OTHER INFORMATION: S.mutans CBP primer (cnm1R)

<400> SEQUENCE: 14
gcaaagactc ttgtccctgc                                           20

<210> SEQ ID NO 15
<211> LENGTH: 30
<212> TYPE: DNA
<213> ORGANISM: Artificial
<220> FEATURE:
<223> OTHER INFORMATION: S.mutans PAC primer (pac-F)

<400> SEQUENCE: 15
gcgcgcatgc tttattcaga tttggaggat                                30

<210> SEQ ID NO 16
<211> LENGTH: 30
<212> TYPE: DNA
<213> ORGANISM: Artificial
<220> FEATURE:
<223> OTHER INFORMATION: S.mutans PAC primer (pac-R)

<400> SEQUENCE: 16
gcgaaagcgc atgctgtgat ttatcgcttc                                30

<210> SEQ ID NO 17
<211> LENGTH: 1566
<212> TYPE: PRT
<213> ORGANISM: Streptococcus mutans

<400> SEQUENCE: 17
```

| | | | | | | | | | | | | | | | |
|---|---|---|---|---|---|---|---|---|---|---|---|---|---|---|---|
| Met | Lys | Val | Lys | Lys | Thr | Tyr | Gly | Phe | Arg | Lys | Ser | Lys | Ile | Ser | Lys |
| 1 | | | | 5 | | | | | 10 | | | | | 15 | |
| Thr | Leu | Cys | Gly | Ala | Val | Leu | Gly | Thr | Val | Ala | Ala | Val | Ser | Val | Ala |
| | | | 20 | | | | | 25 | | | | | 30 | | |
| Gly | Gln | Lys | Val | Phe | Ala | Asp | Glu | Thr | Thr | Thr | Ser | Asp | Val | Asp | |
| | | 35 | | | | | 40 | | | | | 45 | | | |
| Thr | Lys | Val | Val | Gly | Thr | Gln | Thr | Gly | Asn | Pro | Ala | Thr | Asn | Leu | Pro |
| 50 | | | | | 55 | | | | | 60 | | | | | |
| Glu | Ala | Gln | Gly | Ser | Ala | Ser | Lys | Glu | Ala | Glu | Gln | Ser | Gln | Asn | Gln |
| 65 | | | | | 70 | | | | | 75 | | | | | 80 |
| Ala | Gly | Glu | Thr | Asn | Gly | Ser | Ile | Pro | Val | Glu | Val | Pro | Lys | Thr | Asp |
| | | | | 85 | | | | | 90 | | | | | 95 | |
| Leu | Asp | Gln | Ala | Ala | Lys | Asp | Ala | Lys | Ser | Ala | Gly | Val | Asn | Val | Val |
| | | | 100 | | | | | 105 | | | | | 110 | | |
| Gln | Asp | Ala | Asp | Val | Asn | Lys | Gly | Thr | Val | Lys | Thr | Ala | Glu | Glu | Ala |
| | | 115 | | | | | 120 | | | | | 125 | | | |
| Val | Gln | Lys | Glu | Thr | Glu | Ile | Lys | Glu | Asp | Tyr | Thr | Lys | Gln | Ala | Glu |
| | 130 | | | | | 135 | | | | | 140 | | | | |
| Asp | Ile | Lys | Lys | Thr | Thr | Asp | Gln | Tyr | Lys | Ser | Asp | Val | Ala | Ala | His |
| 145 | | | | | 150 | | | | | 155 | | | | | 160 |
| Glu | Ala | Glu | Val | Ala | Lys | Ile | Lys | Ala | Lys | Asn | Gln | Ala | Thr | Lys | Glu |
| | | | | 165 | | | | | 170 | | | | | 175 | |
| Gln | Tyr | Glu | Lys | Asp | Met | Ala | Ala | His | Lys | Ala | Glu | Val | Glu | Arg | Ile |
| | | | 180 | | | | | 185 | | | | | 190 | | |
| Asn | Ala | Ala | Asn | Ala | Ala | Ser | Lys | Thr | Ala | Tyr | Glu | Ala | Lys | Leu | Ala |
| | | 195 | | | | | 200 | | | | | 205 | | | |
| Gln | Tyr | Gln | Ala | Asp | Leu | Ala | Ala | Val | Gln | Lys | Thr | Asn | Ala | Ala | Asn |

```
            210                 215                 220
Gln Ala Ala Tyr Gln Lys Ala Leu Ala Ala Tyr Gln Ala Glu Leu Lys
225                 230                 235                 240

Arg Val Gln Glu Ala Asn Ala Ala Lys Ala Ala Tyr Asp Thr Ala
                245                 250                 255

Val Ala Ala Asn Asn Ala Lys Asn Thr Glu Ile Ala Ala Asn Glu
                260                 265                 270

Glu Ile Arg Lys Arg Asn Ala Thr Ala Lys Ala Glu Tyr Glu Thr Lys
                275                 280                 285

Leu Ala Gln Tyr Gln Ala Glu Leu Lys Arg Val Gln Glu Ala Asn Ala
    290                 295                 300

Ala Asn Glu Ala Asp Tyr Gln Ala Lys Leu Thr Ala Tyr Gln Thr Glu
305                 310                 315                 320

Leu Ala Arg Val Gln Lys Ala Asn Ala Asp Ala Lys Ala Ala Tyr Glu
                325                 330                 335

Ala Ala Val Ala Ala Asn Asn Ala Lys Asn Ala Ala Leu Thr Ala Glu
                340                 345                 350

Asn Thr Ala Ile Lys Gln Arg Asn Glu Asn Ala Lys Ala Thr Tyr Glu
                355                 360                 365

Ala Ala Leu Lys Gln Tyr Glu Ala Asp Leu Ala Ala Val Lys Lys Ala
    370                 375                 380

Asn Ala Ala Asn Glu Ala Asp Tyr Gln Ala Lys Leu Thr Ala Tyr Gln
385                 390                 395                 400

Thr Glu Leu Ala Arg Val Gln Lys Ala Asn Ala Asp Ala Lys Ala Ala
                405                 410                 415

Tyr Glu Ala Ala Val Ala Ala Asn Asn Ala Asn Ala Ala Leu Thr
                420                 425                 430

Ala Glu Asn Thr Ala Ile Lys Lys Arg Asn Ala Asp Ala Lys Ala Asp
                435                 440                 445

Tyr Glu Ala Lys Leu Ala Lys Tyr Gln Ala Asp Leu Ala Lys Tyr Gln
    450                 455                 460

Lys Asp Leu Ala Asp Tyr Pro Val Lys Leu Lys Ala Tyr Glu Asp Glu
465                 470                 475                 480

Gln Ala Ser Ile Lys Ala Ala Leu Ala Glu Leu Lys His Lys Asn
                485                 490                 495

Glu Asp Gly Asn Leu Thr Glu Pro Ser Ala Gln Asn Leu Val Tyr Asp
                500                 505                 510

Leu Glu Pro Asn Ala Asn Leu Ser Leu Thr Thr Asp Gly Lys Phe Leu
    515                 520                 525

Lys Ala Ser Ala Val Asp Asp Ala Phe Ser Lys Ser Thr Ser Lys Ala
    530                 535                 540

Lys Tyr Asp Gln Lys Ile Leu Gln Leu Asp Leu Asp Ile Thr Asn
545                 550                 555                 560

Leu Glu Gln Ser Asn Asp Val Ala Ser Ser Met Glu Leu Tyr Gly Asn
                565                 570                 575

Phe Gly Asp Lys Ala Gly Trp Ser Thr Thr Val Ser Asn Asn Ser Gln
                580                 585                 590

Val Lys Trp Gly Ser Val Leu Leu Glu Arg Gly Gln Ser Ala Thr Ala
    595                 600                 605

Thr Tyr Thr Asn Leu Gln Asn Ser Tyr Tyr Asn Gly Lys Lys Ile Ser
    610                 615                 620

Lys Ile Val Tyr Lys Tyr Thr Val Asp Pro Lys Ser Lys Phe Gln Gly
625                 630                 635                 640
```

```
Gln Lys Val Trp Leu Gly Ile Phe Thr Asp Pro Thr Leu Gly Val Phe
                645                 650                 655

Ala Ser Ala Tyr Thr Gly Gln Val Glu Lys Asn Thr Ser Ile Phe Ile
                660                 665                 670

Lys Asn Glu Phe Thr Phe Tyr Asp Glu Asp Gly Lys Pro Ile Asp Phe
            675                 680                 685

Asp Asn Ala Leu Leu Ser Val Ala Ser Leu Asn Arg Glu His Asn Ser
            690                 695                 700

Ile Glu Met Ala Lys Asp Tyr Ser Gly Lys Phe Val Lys Ile Ser Gly
705                 710                 715                 720

Ser Ser Ile Gly Glu Lys Asn Gly Met Ile Tyr Ala Thr Asp Thr Leu
                725                 730                 735

Asn Phe Lys Gln Gly Glu Gly Gly Ser Arg Trp Thr Met Tyr Lys Asn
                740                 745                 750

Ser Gln Ala Gly Ser Gly Trp Asp Ser Ser Asp Ala Pro Asn Ser Trp
            755                 760                 765

Tyr Gly Ala Gly Ala Ile Lys Met Ser Gly Pro Asn Asn His Val Thr
            770                 775                 780

Val Gly Ala Thr Ser Ala Thr Asn Val Met Pro Val Ser Asp Met Pro
785                 790                 795                 800

Val Val Pro Gly Lys Asp Asn Thr Asp Gly Lys Pro Asn Ile Trp
                805                 810                 815

Tyr Ser Leu Asn Gly Lys Ile Arg Ala Val Asn Val Pro Lys Val Thr
                820                 825                 830

Lys Glu Lys Pro Thr Pro Pro Val Lys Pro Thr Ala Pro Thr Lys Pro
                835                 840                 845

Thr Tyr Glu Thr Glu Lys Pro Leu Lys Pro Ala Pro Val Ala Pro Asn
            850                 855                 860

Tyr Glu Lys Glu Pro Thr Pro Thr Arg Thr Pro Asp Gln Ala Glu
865                 870                 875                 880

Pro Asn Lys Pro Thr Pro Pro Thr Tyr Glu Thr Glu Lys Pro Leu Glu
                885                 890                 895

Pro Ala Pro Val Glu Pro Ser Tyr Glu Ala Glu Pro Thr Pro Pro Thr
            900                 905                 910

Arg Thr Pro Asp Gln Ala Glu Pro Asn Lys Pro Thr Pro Pro Thr Tyr
            915                 920                 925

Glu Thr Glu Lys Pro Leu Glu Pro Ala Pro Val Glu Pro Ser Tyr Glu
            930                 935                 940

Ala Glu Pro Thr Pro Pro Thr Pro Thr Pro Asp Gln Pro Glu Pro Asn
945                 950                 955                 960

Lys Pro Val Glu Pro Thr Tyr Glu Val Ile Pro Thr Pro Pro Thr Asp
                965                 970                 975

Pro Val Tyr Gln Asp Leu Pro Thr Pro Pro Ser Val Pro Thr Val His
            980                 985                 990

Phe His Tyr Phe Lys Leu Ala Val Gln Pro Gln Val Asn Lys Glu Ile
            995                 1000                1005

Arg Asn Asn Asn Asp Val Asn Ile Asp Arg Thr Leu Val Ala Lys
            1010                1015                1020

Gln Ser Val Val Lys Phe Gln Leu Lys Thr Ala Asp Leu Pro Ala
            1025                1030                1035

Gly Arg Asp Glu Thr Thr Ser Phe Val Leu Val Asp Pro Leu Pro
            1040                1045                1050
```

-continued

Ser Gly Tyr Gln Phe Asn Pro Glu Ala Thr Lys Ala Ala Ser Pro
    1055                1060                1065

Gly Phe Asp Val Ala Tyr Asp Asn Ala Thr Asn Thr Val Thr Phe
    1070                1075                1080

Lys Ala Thr Ala Ala Thr Leu Ala Thr Phe Asn Ala Asp Leu Thr
    1085                1090                1095

Lys Ser Val Ala Thr Ile Tyr Pro Thr Val Val Gly Gln Val Leu
    1100                1105                1110

Asn Asp Gly Ala Thr Tyr Lys Asn Asn Phe Thr Leu Thr Val Asn
    1115                1120                1125

Asp Ala Tyr Gly Ile Lys Ser Asn Val Val Arg Val Thr Thr Pro
    1130                1135                1140

Gly Lys Pro Asn Asp Pro Asp Asn Pro Asn Asn Asn Tyr Ile Lys
    1145                1150                1155

Pro Thr Lys Val Asn Lys Asn Glu Asn Gly Val Val Ile Asp Gly
    1160                1165                1170

Lys Thr Val Leu Ala Gly Ser Thr Asn Tyr Tyr Glu Leu Thr Trp
    1175                1180                1185

Asp Leu Asp Gln Tyr Lys Asn Asp Arg Ser Ser Ala Asp Thr Ile
    1190                1195                1200

Gln Gln Gly Phe Tyr Tyr Val Asp Asp Tyr Pro Glu Glu Ala Leu
    1205                1210                1215

Glu Leu Arg Gln Asp Leu Val Lys Ile Thr Asp Ala Asn Gly Asn
    1220                1225                1230

Glu Val Thr Gly Val Ser Val Asp Asn Tyr Thr Ser Leu Glu Ala
    1235                1240                1245

Ala Pro Gln Glu Ile Arg Asp Val Leu Ser Lys Ala Gly Ile Arg
    1250                1255                1260

Pro Lys Gly Ala Phe Gln Ile Phe Arg Ala Asn Asn Pro Arg Glu
    1265                1270                1275

Phe Tyr Asp Thr Tyr Val Lys Thr Gly Ile Asp Leu Lys Ile Val
    1280                1285                1290

Ser Pro Met Val Val Lys Lys Gln Met Gly Gln Thr Gly Gly Ser
    1295                1300                1305

Tyr Glu Asn Gln Ala Tyr Gln Ile Asp Phe Gly Asn Gly Tyr Ala
    1310                1315                1320

Ser Asn Ile Val Ile Asn Asn Val Pro Lys Ile Asn Pro Lys Lys
    1325                1330                1335

Asp Val Thr Leu Thr Leu Asp Pro Ala Asp Thr Asn Asn Val Asp
    1340                1345                1350

Gly Gln Thr Ile Pro Leu Asn Thr Val Phe Asn Tyr Arg Leu Ile
    1355                1360                1365

Gly Gly Ile Ile Pro Ala Asn His Ser Glu Glu Leu Phe Glu Tyr
    1370                1375                1380

Asn Phe Tyr Asp Asp Tyr Asp Gln Thr Gly Asp His Tyr Thr Gly
    1385                1390                1395

Gln Tyr Lys Val Phe Ala Lys Val Asp Ile Thr Leu Lys Asn Gly
    1400                1405                1410

Val Ile Ile Lys Ser Gly Thr Glu Leu Thr Gln His Thr Thr Ala
    1415                1420                1425

Glu Val Asp Thr Thr Lys Gly Ala Ile Thr Ile Lys Phe Lys Glu
    1430                1435                1440

Ala Phe Leu Arg Ser Val Ser Ile Asp Ser Ala Phe Gln Ala Glu

-continued

```
    1445                1450                1455
Ser Tyr Ile Gln Met Lys Arg Ile Ala Val Gly Thr Phe Glu Asn
    1460                1465                1470

Thr Tyr Ile Asn Thr Val Asn Gly Val Thr Tyr Ser Ser Asn Thr
    1475                1480                1485

Val Lys Thr Thr Thr Pro Glu Asp Pro Thr Asp Pro Thr Asp Pro
    1490                1495                1500

Gln Asp Pro Ser Ser Pro Arg Thr Ser Thr Val Ile Asn Tyr Lys
    1505                1510                1515

Pro Gln Ser Thr Ala Tyr Gln Pro Ser Ser Val Gln Lys Thr Leu
    1520                1525                1530

Pro Asn Thr Gly Val Thr Asn Asn Ala Tyr Met Pro Leu Leu Gly
    1535                1540                1545

Ile Ile Gly Leu Val Thr Ser Phe Ser Leu Leu Gly Leu Lys Ala
    1550                1555                1560

Lys Lys Asp
    1565

<210> SEQ ID NO 18
<211> LENGTH: 4701
<212> TYPE: DNA
<213> ORGANISM: Streptococcus mutans

<400> SEQUENCE: 18
atgaaagtca aaaaaactta cggttttcgt aaaagtaaaa ttagtaaaac actgtgtggt    60
gctgttctag aacagtagc agcagtctct gtagcgggac aaaaggtttt tgccgatgaa   120
acgaccacta ctagtgatgt agatactaaa gtagttggaa cacaaactgg aaatccagcg   180
accaatttgc cagaggctca agggagtgcg agtaaggaag ctgaacaaag tcaaaaccaa   240
gctggagaga caaatggttc aataccagtt gaagtaccta aaactgatct tgatcaagca   300
gcaaaagatg ctagtctgc tggtgtcaat gttgtccaag atgccgatgt taataaagga   360
actgttaaaa cagctgaaga agcagtccaa aagaaactg aaattaaaga agattacaca   420
aaacaagctg aggatattaa gaagacaaca gatcaatata atcggatgt agctgctcat   480 gaggcagaag ttgctaaaat caaagctaaa atcaggcga ctaaagaaca gtatgaaaaa   540
gatatggcag ctcataaagc cgaggttgaa cgcattaatg ctgcaaatgc tgccagtaaa   600
acagcttatg aagctaaatt ggctcaatat caagcagatt tagcagccgt tcaaaaaacc   660
aatgctgcca atcaagcagc ctatcaaaaa gcccttgctg cctatcaggc tgaactgaaa   720
cgtgttcagg aagctaatgc agccgccaaa gctgcttatg atactgctgt agcagcaaat   780
aatgccaaaa atacagaaat tgccgctgcc aatgaagaaa ttagaaacg caatgcaacg   840 gccaaagctg aatatgagac taagttagct caatatcaag ctgaactaaa gcgtgttcag   900
gaagctaatg ccgcaaacga agcagactat caagctaaat tgaccgccta tcaaacagag   960
ctcgctcgcg ttcaaaaggc taatgcggat gctaaagcgg cctatgaagc agctgtagca   1020
gcaaataatg ccaaaaatgc ggcactcaca gctgaaaata ctgcaattaa gcaacgcaat   1080
gagaatgcta aggcgactta tgaagctgca ctcaagcaat atgaggccga tttggcagcg   1140
gtgaaaaaag ctaatgccgc aaacgaagca gactatcaag ctaaattgac cgcctatcaa   1200
acagagctcg ctcgcgttca aaaagccaat gcggatgcta agcggccta tgaagcagct   1260 gtagcagcaa ataatgccgc aaatgcagcg ctcacagctg aaaatactgc aattaagaag   1320
cgcaatgcgg atgctaaagc tgattacgaa gcaaaacttg ctaagtatca agcagatctt   1380
```

```
gccaaatatc agaaagattt agcagactat ccagttaagt taaaggcata cgaagatgaa    1440
caagcttcta ttaaagctgc actggcagaa cttgaaaaac ataaaaatga agacggaaac    1500
ttaacagaac catctgctca aaatttggtc tatgatcttg agccaaatgc gaacttatct    1560
ttgacaacag atgggaagtt ccttaaggct tctgctgtgg atgatgcttt tagcaaaagc    1620
acttcaaaag caaaatatga ccaaaaaatt cttcaattag atgacctaga tataactaac    1680
ttagaacaat ctaatgatgt tgcttcttct atggagcttt atgggaattt tggtgataaa    1740
gctggctggt caacaacagt aagcaataac tcacaggtta atggggatc ggtacttta     1800 gagcgcggtc aaagcgcaac agctacatac actaacctgc agaattctta ttacaatggt    1860
aaaaagattt ctaaaattgt ctacaagtat acagtggacc ctaagtccaa gtttcaaggt    1920
caaaaggttt ggttaggtat ttttaccgat ccaactttag gtgttttgc ttccgcttat     1980 acaggtcaag ttgaaaaaaa cacttctatt tttattaaaa atgaattcac tttctatgac    2040
gaagatggaa aaccaattga ttttgataat gcccttctct cagtagcttc tcttaaccgt    2100
gaacataact ctattgagat ggctaaagat tatagtggta aatttgtcaa aatctctggt    2160
tcatctattg gtgaaaagaa tggcatgatt tatgctacag atactcttaa ctttaaacag    2220
ggtgaaggcg gctctcgctg gactatgtat aaaaatagtc aagctggttc aggatgggat    2280
agttcagatg cgccgaattc ttggtatgga gcagggcta ttaaaatgtc tggtccgaat     2340
aaccatgtta ctgtaggagc aacttctgca acaaatgtga tgccagtttc tgacatgcct    2400
gttgttcctg gtaaggacaa tactgatggc aaaaaaccaa atatttggta ttctttaaat    2460
ggtaaaatcc gtgcggttaa tgttcctaaa gttactaagg aaaaacccac acctccggtt    2520
aaaccaacag ctccaactaa accaacttat gaaacagaaa agccattaaa accggcacca    2580
gtagctccaa attatgaaaa ggagccaaca ccgccgacaa ggacaccgga tcaagcagag    2640
ccaaataaac ccacaccgcc gacctatgaa acagaaaagc cgttggagcc agcacctgtt    2700
gagccaagct atgaagcaga gccaacaccg ccgacaagga caccggatca ggcagagcca    2760
aataaaccca caccgccgac ctatgaaaca gaaaagccgt tggagccagc acctgttgag    2820
ccaagctatg aagcagagcc aacgccaccg acaccaacac cagatcaacc agaaccaaac    2880
aaacctgttg agccaactta tgaggttatt ccaacaccgc cgactgatcc tgtttatcaa    2940
gatcttccaa cacctccatc tgtaccaact gttcatttcc attactttaa actagctgtt    3000
cagccgcagg ttaacaaaga aattagaaac aataacgatg ttaatattga cagaactttg    3060
gtggctaaac aatctgttgt taagttccag ctgaagacag cagatctccc tgctggacgt    3120
gatgaaacaa cttcctttgt cttggtagat cccctgccat ctggttatca atttaatcct    3180
gaagctacaa aagctgccag ccctggcttt gatgtcgctt atgataatgc aactaataca    3240
gtcaccttca aggcaactgc agcaactttg gctacgtta atgctgattt gactaagtca      3300
gtggcaacga tttatccaac agtggtcgga caagttctta cgatggcgc aacttataag     3360 aataatttca cactcacagt caatgatgct tatggcatta atccaatgt tgttcgggtg     3420 acaactcctg gtaaaccaaa tgatccagat aacccaaata taattatat taaaccaact    3480 aaggttaata aaaacgaaaa tggcgttgtt attgatggta aaacagttct tgccggttca    3540
acgaattatt atgagctaac ttgggatttg gatcaatata gaacgaccg ctcttcagca     3600 gataccattc aacaaggatt ttactatgta gatgattatc cagaagaagc gcttgaattg    3660
cgtcaggatt tagtgaagat tacagatgct aatggtaatg aagttactgg tgttagtgtg    3720
```

```
gataattata ctagtcttga agcagcccct caagaaatta gagatgttct ttctaaggca    3780
ggaattagac ctaaaggtgc tttccaaatt ttccgtgcca ataatccaag agaattttat    3840
gatacttatg tcaaaactgg aattgatttg aagattgtat caccaatggt tgttaaaaaa    3900
caaatgggac aaacaggtgg cagttatgaa aatcaagctt accaaattga ctttggtaat    3960
ggttatgcat caaatatcgt tatcaataat gttcctaaga ttaaccctaa gaaagatgtg    4020
accttaacac ttgatccggc tgatacaaat aatgttgatg gtcagactat tccacttaat    4080
acagtcttta attaccgttt gattggtggc attatccctg caaatcactc agaagaactc    4140
tttgaataca atttctatga tgattatgat caaacaggag atcactatac tggtcagtat    4200
aaagttttg ccaaggttga tatcactctt aaaaacggtg ttattattaa gtcaggtact    4260
gaattgactc agcatacgac agcggaagtt gataccacta aaggtgctat cacaattaag    4320
ttcaaggaag cctttctgcg ttctgtttca attgattcag ccttccaagc tgaaagttat    4380
atccaaatga aacgtattgc ggttggtact tttgaaaata cttatattaa tactgtcaat    4440
ggggtaactt acagttcaaa tacagtgaaa acaactactc ctgaggatcc tacagaccct    4500
actgatccgc aagatccatc atcaccgcgg acttcaactg taattaacta caaacctcaa    4560
tcaactgctt atcaaccaag ctctgtccaa aaaacgttac caaatacggg agtaacaaac    4620
aatgcttata tgcctttact tggtattatt ggcttagtta ctagttttag tttgcttggc    4680
ttaaaggcta agaaagattg a                                              4701
```

<210> SEQ ID NO 19
<211> LENGTH: 1564
<212> TYPE: PRT
<213> ORGANISM: Streptococcus mutans

<400> SEQUENCE: 19

Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Val Ser Val Ala
            20                  25                  30

Gly Gln Lys Val Phe Ala Asp Glu Thr Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Ala Gln Gly Ser Ala Ser Lys Glu Ala Glu Gln Ser Gln Asn Gln
65                  70                  75                  80

Ala Gly Glu Thr Asn Gly Ser Ile Pro Ile Glu Val Pro Lys Thr Asp
                85                  90                  95

Leu Asp Gln Thr Ala Lys Asp Ala Lys Ser Ala Gly Val Asn Val Val
            100                 105                 110

Gln Asp Ala Asp Val Asn Lys Gly Thr Val Lys Thr Ala Glu Ala Ala
        115                 120                 125

Val Gln Lys Glu Thr Glu Ile Lys Glu Asp Tyr Thr Gln Ala Glu
    130                 135                 140

Asp Ile Lys Lys Thr Thr Asp Gln Tyr Lys Ser Asp Val Ala Ala His
145                 150                 155                 160

Glu Ala Glu Val Ala Lys Ile Lys Ala Lys Asn Gln Ala Thr Lys Glu
                165                 170                 175

Gln Tyr Glu Lys Asp Met Ala Ala His Lys Ala Glu Val Glu Arg Ile
            180                 185                 190

Asn Ala Ala Asn Ala Ala Ser Lys Thr Ala Tyr Glu Ala Lys Leu Ala

```
                195                 200                 205
Gln Tyr Gln Ala Asp Leu Ala Ala Val Gln Lys Thr Asn Ala Ala Asn
210                 215                 220

Gln Ala Ala Tyr Gln Lys Ala Leu Ala Ala Tyr Gln Ala Glu Leu Lys
225                 230                 235                 240

Arg Val Gln Glu Ala Asn Ala Ala Ala Lys Ala Ala Tyr Asp Thr Ala
                245                 250                 255

Val Ala Ala Asn Asn Ala Lys Asn Thr Glu Ile Thr Ala Ala Asn Glu
                260                 265                 270

Glu Ile Arg Lys Arg Asn Ala Thr Ala Lys Ala Glu Tyr Glu Thr Lys
                275                 280                 285

Leu Ala Gln Tyr Gln Ala Glu Leu Lys Arg Val Gln Glu Ala Asn Ala
290                 295                 300

Ala Asn Glu Ala Asp Tyr Gln Ala Lys Leu Thr Ala Tyr Gln Thr Glu
305                 310                 315                 320

Leu Ala Arg Val Gln Lys Ala Asn Ala Asp Ala Lys Ala Ala Tyr Glu
                325                 330                 335

Ala Ala Val Ala Ala Asn Asn Ala Lys Asn Ala Ala Leu Thr Ala Glu
                340                 345                 350

Asn Thr Ala Ile Lys Gln Arg Asn Glu Asn Ala Lys Ala Thr Tyr Glu
                355                 360                 365

Ala Ala Leu Lys Gln Tyr Glu Ala Asp Leu Ala Ala Lys Lys Ala
                370                 375                 380

Asn Ala Ala Asn Glu Ala Asp Tyr Gln Ala Lys Leu Thr Ala Tyr Gln
385                 390                 395                 400

Thr Glu Leu Ala Arg Val Gln Lys Thr Asn Ala Asp Ala Lys Ala Ala
                405                 410                 415

Tyr Glu Ala Ala Val Ala Ala Asn Asn Ala Ala Asn Ala Ala Leu Thr
                420                 425                 430

Ala Glu Asn Thr Ala Ile Lys Lys Arg Asn Ala Asp Ala Lys Ala Asp
                435                 440                 445

Tyr Glu Ala Lys Leu Ala Lys Tyr Gln Ala Asp Leu Ala Lys Tyr Gln
                450                 455                 460

Lys Asp Leu Ala Asp Tyr Pro Val Lys Leu Lys Ala Tyr Glu Asp Glu
465                 470                 475                 480

Gln Ala Ser Ile Lys Ala Ala Leu Ala Glu Leu Glu Lys His Lys Asn
                485                 490                 495

Glu Asp Gly Asn Leu Thr Glu Pro Ser Ala Gln Asn Leu Val Tyr Asp
                500                 505                 510

Leu Glu Pro Asn Ala Asn Leu Ser Leu Thr Thr Asp Gly Lys Phe Leu
                515                 520                 525

Lys Ala Ser Ala Val Asp Asn Ala Phe Lys Gln Asp Thr Asn Gln Tyr
                530                 535                 540

Ser Lys Lys Asn Leu Gln Leu Asp Asn Leu Asn Val Lys Tyr Leu Glu
545                 550                 555                 560

Asn Ala Gly Ala Thr Ala Ser Ser Met Glu Leu Tyr Gly Asn Ile Gly
                565                 570                 575

Asp Lys Ser Ser Trp Thr Thr Asn Val Gly Asn Lys Thr Glu Val Lys
                580                 585                 590

Trp Gly Ser Val Leu Leu Glu Arg Gly Gln Ser Ala Thr Ala Thr Tyr
                595                 600                 605

Thr Asn Leu Gln Asn Ser Tyr Tyr Asn Gly Lys Lys Ile Ser Lys Ile
                610                 615                 620
```

```
Val Tyr Lys Tyr Thr Val Asp Pro Lys Ser Lys Phe Gln Gly Gln Lys
625                 630                 635                 640

Val Trp Leu Gly Ile Phe Thr Asp Pro Thr Leu Gly Val Phe Ala Ser
            645                 650                 655

Ala Tyr Thr Gly Gln Val Glu Lys Asn Thr Ser Ile Phe Ile Lys Asn
        660                 665                 670

Glu Phe Thr Phe Tyr Asp Glu Asp Gly Lys Pro Ile Asp Phe Asp Asn
    675                 680                 685

Ala Leu Leu Ser Val Ala Ser Leu Asn Arg Glu His Asn Ser Ile Glu
690                 695                 700

Met Ala Lys Asp Tyr Ser Gly Lys Phe Val Lys Ile Ser Gly Ser Ser
705                 710                 715                 720

Ile Gly Glu Lys Asn Gly Met Ile Tyr Ala Thr Asp Thr Leu Asn Phe
            725                 730                 735

Lys Gln Gly Glu Gly Gly Ser Arg Trp Thr Met Tyr Lys Asn Ser Gln
        740                 745                 750

Ala Gly Ser Gly Trp Asp Ser Asp Ala Pro Asn Ser Trp Tyr Gly
        755                 760                 765

Ala Gly Ala Ile Lys Met Ser Gly Pro Asn Asn His Val Thr Val Gly
770                 775                 780

Ala Thr Ser Ala Thr Asn Val Met Pro Val Ser Asp Met Pro Val Val
785                 790                 795                 800

Pro Gly Lys Asp Asn Thr Asp Gly Lys Lys Pro Asn Ile Trp Tyr Ser
            805                 810                 815

Leu Asn Gly Lys Ile Arg Ala Val Asn Val Pro Lys Val Thr Lys Glu
        820                 825                 830

Lys Pro Thr Pro Pro Val Lys Pro Thr Ala Pro Thr Lys Pro Thr Tyr
        835                 840                 845

Glu Thr Glu Lys Pro Leu Lys Pro Ala Pro Val Ala Pro Asn Tyr Glu
850                 855                 860

Lys Glu Pro Thr Pro Thr Arg Thr Pro Asp Gln Ala Glu Pro Asn
865                 870                 875                 880

Lys Pro Thr Pro Thr Tyr Glu Thr Glu Lys Pro Leu Glu Pro Ala
        885                 890                 895

Pro Val Glu Pro Ser Tyr Glu Ala Glu Pro Thr Pro Thr Arg Thr
            900                 905                 910

Pro Asp Gln Ala Glu Pro Asn Lys Pro Thr Pro Thr Tyr Glu Thr
    915                 920                 925

Glu Lys Pro Leu Glu Pro Ala Pro Val Glu Pro Ser Tyr Glu Ala Glu
930                 935                 940

Pro Thr Pro Pro Thr Pro Thr Pro Asp Gln Pro Glu Pro Asn Lys Pro
945                 950                 955                 960

Val Glu Pro Thr Tyr Glu Val Ile Pro Thr Pro Thr Asp Pro Val
            965                 970                 975

Tyr Gln Asp Leu Pro Thr Pro Ser Val Pro Thr Val His Phe His
            980                 985                 990

Tyr Phe Lys Leu Ala Val Gln Pro Gln Val Asn Lys Glu Ile Arg Asn
        995                 1000                1005

Asn Asn  Asp Val Asn Ile Asp  Arg Thr Leu Val Ala  Lys Gln Ser
    1010            1015                 1020

Val Val  Lys Phe Gln Leu Lys  Thr Ala Asp Leu Pro  Ala Gly Arg
    1025            1030                 1035
```

```
Asp Glu Thr Thr Ser Phe Val Leu Val Asp Pro Leu Pro Ser Gly
    1040                1045                1050

Tyr Gln Phe Asn Pro Glu Ala Thr Lys Ala Ala Ser Pro Gly Phe
    1055                1060                1065

Asp Val Thr Tyr Asp Asn Ala Thr Asn Thr Val Thr Phe Lys Ala
    1070                1075                1080

Thr Ala Ala Thr Leu Ala Thr Phe Asn Ala Asp Leu Thr Lys Ser
    1085                1090                1095

Val Ala Thr Ile Tyr Pro Thr Val Val Gly Gln Val Leu Asn Asp
    1100                1105                1110

Gly Ala Thr Tyr Lys Asn Asn Phe Thr Leu Thr Val Asn Asp Ala
    1115                1120                1125

Tyr Gly Ile Lys Ser Asn Val Val Arg Val Thr Thr Pro Gly Lys
    1130                1135                1140

Pro Asn Asp Pro Asp Asn Pro Asn Asn Tyr Ile Lys Pro Thr
    1145                1150                1155

Lys Val Asn Lys Asn Glu Asn Gly Val Val Ile Asp Gly Lys Thr
    1160                1165                1170

Val Leu Ala Gly Ser Thr Asn Tyr Tyr Glu Leu Thr Trp Asp Leu
    1175                1180                1185

Asp Gln Tyr Lys Asn Asp Arg Ser Ser Ala Asp Thr Ile Gln Lys
    1190                1195                1200

Gly Phe Tyr Tyr Val Asp Asp Tyr Pro Glu Glu Ala Leu Glu Leu
    1205                1210                1215

Arg Gln Asp Leu Val Lys Ile Thr Asp Ala Asn Gly Asn Glu Val
    1220                1225                1230

Thr Gly Val Ser Val Asp Asn Tyr Thr Ser Leu Glu Ala Ala Pro
    1235                1240                1245

Gln Glu Ile Arg Asp Val Leu Ser Lys Ala Gly Ile Arg Pro Lys
    1250                1255                1260

Gly Ala Phe Gln Ile Phe Arg Ala Asp Asn Pro Arg Glu Phe Tyr
    1265                1270                1275

Asp Thr Tyr Val Lys Thr Gly Ile Asp Leu Lys Ile Val Ser Pro
    1280                1285                1290

Met Val Val Lys Lys Gln Met Gly Gln Thr Gly Gly Ser Tyr Glu
    1295                1300                1305

Asn Gln Ala Tyr Gln Ile Asp Phe Gly Asn Gly Tyr Ala Ser Asn
    1310                1315                1320

Ile Val Ile Asn Asn Val Pro Lys Ile Asn Pro Lys Lys Asp Val
    1325                1330                1335

Thr Leu Thr Leu Asp Pro Ala Asp Thr Asn Asn Val Asp Gly Gln
    1340                1345                1350

Thr Ile Pro Leu Asn Thr Val Phe Asn Tyr Arg Leu Ile Gly Gly
    1355                1360                1365

Ile Ile Pro Ala Asn His Ser Glu Glu Leu Phe Glu Tyr Asn Phe
    1370                1375                1380

Tyr Asp Asp Tyr Asp Gln Thr Gly Asp His Tyr Thr Gly Gln Tyr
    1385                1390                1395

Lys Val Phe Ala Lys Val Asp Ile Thr Phe Lys Asp Gly Ser Ile
    1400                1405                1410

Ile Lys Ser Gly Ala Glu Leu Thr Gln Tyr Thr Thr Ala Glu Val
    1415                1420                1425

Asp Thr Thr Lys Gly Ala Ile  Thr Ile Lys Phe Lys  Glu Ala Phe
```

```
                1430                1435                1440
Leu Arg Ser Val Ser Ile Asp Ser Val Phe Gln Ala Glu Ser Tyr
    1445                1450                1455
Ile Gln Met Lys Arg Ile Ala Val Gly Thr Phe Glu Asn Thr Tyr
    1460                1465                1470
Ile Asn Thr Val Asn Gly Val Thr Tyr Ser Ser Asn Thr Val Lys
    1475                1480                1485
Thr Thr Thr Pro Glu Asp Pro Thr Asp Pro Thr Asp Pro Gln Asp
    1490                1495                1500
Pro Ala Ser Pro Arg Thr Ser Thr Val Ile Asn Tyr Lys Pro Gln
    1505                1510                1515
Ser Thr Ala Tyr Gln Pro Ser Ser Val Gln Lys Thr Leu Pro Asn
    1520                1525                1530
Thr Gly Val Thr Asn Asn Ala Tyr Met Pro Leu Leu Gly Ile Ile
    1535                1540                1545
Gly Leu Val Thr Ser Phe Ser Leu Leu Gly Leu Lys Ala Lys Lys
    1550                1555                1560
Asp
```

<210> SEQ ID NO 20
<211> LENGTH: 4695
<212> TYPE: DNA
<213> ORGANISM: Streptococcus mutans

<400> SEQUENCE: 20

```
atgaaagtca aaaaactta cggttttcgt aaaagtaaaa ttagtaaaac actgtgtggt    60
gctgttctag aacagtagc agcagtctct gtagcaggac aaaaggtttt tgccgatgaa   120
acgaccacta ctagtgatgt agatactaaa gtagttggaa cacaaactgg aaatccagcg   180
accaatttgc cagaggctca agggagtgcg agtaaggaag ctgaacaaag tcaaaaccaa   240
gctggagaga caaatggttc aataccaatt gaagtaccta aaactgatct tgatcaaaca   300
gcaaaagatg ctaagtctgc tggtgtcaat gttgtccaag atgccgatgt aataaaggca   360
actgttaaaa cagctgaagc agcagtccaa aaagaaactg aaattaaaga agattacaca   420
aaacaagctg aggatattaa aagacaaca gatcaatata atcggatgt agctgctcat   480
gaggcagaag ttgctaaaat caagctaaa atcaggcaa ctaaagaaca gtatgaaaaa   540
gatatggcag ctcataaagc cgaggttgaa cgcattaatg ctgcaaatgc tgccagtaaa   600
acagcttatg aagctaaatt ggctcaatat caagcagatt tagcagccgt tcaaaaaacc   660
aatgctgcca atcaagcagc ctatcaaaaa gcccttgctg cttatcaggc tgaactgaag   720
cgtgttcagg aagctaatgc agccgccaaa gccgcttatg atactgctgt agcagcaaat   780
aatgccaaaa atacagaaat taccgctgcc aatgaagaaa ttagaaaacg caatgcaacg   840
gccaaagctg aatatgagac taagttagct caatatcaag ctgaactaaa gcgtgttcag   900
gaagctaatg cagcaaacga agcagactat caagctaaat tgactgctta tcaaacagag   960
ctcgctcgcg ttcaaaaggc caatgcggat gctaaagcgg cctatgaagc agctgtagca  1020
gcaaataatg ccaaaaatgc ggcactcaca gctgaaaata ctgcaattaa gcaacgcaat  1080
gagaatgcta aggcgactta tgaagctgca ctcaagcaat atgaggccga tttggcagca  1140
gcgaaaaaag ctaatgcagc aaacgaagca gactatcaag ctaaattgac cgcttatcaa  1200
acagagctcg ctcgcgttca aaagaccaat gcggatgcta agcggccta tgaagcagct  1260
gtagcagcaa ataatgccgc aaatgcagcg ctcacagctg aaaatactgc aattaagaag  1320
```

```
cgcaatgcgg atgctaaagc tgattacgaa gcaaaacttg ctaagtatca agcagatctt    1380
gccaaatatc aaaaagattt agcagactat ccagttaagt taaaggcata cgaagatgaa    1440
caagcttcta ttaaagctgc actggcagaa cttgaaaaac ataaaaatga agacggaaac    1500
ttaacagaac catctgctca aaatttggtc tatgatcttg agccaaatgc gaacttatct    1560
ttgacaacag atgggaagtt ccttaaggct tctgctgtgg ataacgcatt taagcaagat    1620
acaaatcaat atagtaaaaa gaaccttcaa ttagataacc ttaatgttaa atatctagaa    1680
aacgcaggag ccactgcctc atctatggaa ttatacggaa atataggtga taaatcgagt    1740
tggacaacaa atgtaggcaa caaaacagaa gttaaatggg gatcggtact tttagagcgc    1800
ggtcaaagcg caacagctac atacactaac ctgcagaatt cttattacaa tggtaaaaag    1860
atttctaaaa ttgtctacaa gtatacagtg daccctaagt ccaagtttca aggtcaaaag    1920
gtttggttag gtattttac cgatccaact ttaggtgttt ttgcttccgc ttatacaggt    1980
caagttgaaa aaacacttc tattttatt aaaaatgaat tcactttcta tgacgaagat    2040
ggaaaaccaa ttgattttga taatgccctt ctctcagtag cttctcttaa ccgtgaacat    2100
aactctattg agatggctaa agattatagt ggtaaatttg tcaaaatctc tggttcatct    2160
attggtgaaa agaatggcat gatttatgct acagatactc ttaactttaa acagggtgaa    2220
ggcggctctc gctggactat gtataaaaat agtcaagctg gttcaggatg ggatagttca    2280
gatgcgccga attcttggta tggagcaggg gctattaaaa tgtctggtcc gaataaccat    2340
gttactgtag gagcaacttc tgcaacaaat gtgatgccag tttctgacat gcctgttgtt    2400
cctggtaagg acaatactga tggcaaaaaa ccaaatattt ggtattcttt aaatggtaaa    2460
atccgtgcgg ttaatgttcc taaagttact aaggaaaaac ccacacctcc ggttaaacca    2520
acagctccaa ctaaaccaac ttatgaaaca gaaaagccat taaaaccggc accagtagct    2580
ccaaattatg aaaaggagcc aacaccgccg acaaggacac cggatcaagc agagccaaat    2640
aaacccacac cgccgaccta tgaaacagaa aagccgttgg agccagcacc tgttgagcca    2700
agctatgaag cagagccaac accgccgaca aggacaccgg atcaggcaga gccaaataaa    2760
cccacaccgc cgacctatga aacagaaaag ccgttggagc cagcacctgt tgagccaagc    2820
tatgaagcag agccaacgcc accgacacca caccagatc aaccagaacc aaacaaacct    2880
gttgagccaa cttatgaggt tattccaaca ccgccgactg atcctgttta tcaagatctt    2940
ccaacacctc catctgtacc aactgttcat ttccattact ttaaactagc tgttcagccg    3000
caggttaaca agaaattag aaacaataac gatgttaata ttgacagaac tttggtggct    3060
aaacaatctg ttgttaagtt ccagctgaag acagcagatc tccctgctgg acgtgatgaa    3120
acaacttcct ttgtcttggt agatccctg ccatctggtt atcaatttaa tcctgaagct    3180
acaaaagctg caagccctgg ctttgatgtc acttatgata atgcaactaa tacagtcacc    3240
ttcaaggcaa ctgcagcaac tttggctacg tttaatgctg atttgactaa gtcagtggca    3300
acgatttatc caacagtggt cggacaagtt cttaatgatg gcgcaactta agaataat    3360 ttcacgctca cagtcaatga tgcttatggc attaaatcca atgttgttcg ggtgacaact    3420
cctggtaaac caaatgatcc agataatcca ataataatt atattaaacc aactaaggtt    3480
aataaaaacg aaaatggcgt tgttattgat ggtaaaacag ttcttgccgg ttcaacgaat    3540
tattatgagc taacttggga tttggatcaa tataaaaacg accgctcttc agcagatacc    3600
attcaaaaag gatttactta tgtagatgat tatccagaag aagcgcttga attgcgtcag    3660
```

```
gatttagtga agattacaga tgctaatggt aatgaagtta ctggtgttag tgtggataat    3720
tatactagtc ttgaagcagc ccctcaagaa attagagatg ttctttctaa ggcaggaatt    3780
agacctaaag gtgctttcca aattttccgt gccgataatc aagagaatt ttatgatact     3840 tatgtcaaaa ctggaattga tttgaagatt gtatcaccaa tggttgttaa aaaacaaatg    3900
ggacaaacag gcggcagtta tgaaaatcaa gcttaccaaa ttgactttgg taatggttat    3960
gcatcaaata tcgttatcaa taatgttcct aagattaacc ctaagaaaga tgtgacctta    4020
acacttgatc cggctgatac aaataatgtt gatggtcaga ctattccact aatacagtc     4080 tttaattacc gtttgattgg tggcattatc cctgcaaatc actcagaaga actctttgaa    4140
tacaatttct atgatgatta tgatcaaaca ggagatcact atactggtca gtataaagtt    4200
tttgccaagg ttgatatcac tttaaagac ggttctatta tcaagtcagg tgctgagtta     4260
actcagtata cgacagcgga agttgatacc actaaaggtg ctatcacaat taagttcaag    4320
gaagcctttc tgcgttctgt ttcaattgat tcagtcttcc aagctgaaag ttatatccaa    4380
atgaaacgta ttgcggttgg tactttgaa aatacttata ttaatactgt caatggggta     4440
acttacagtt caaatacagt gaaaacaact actcctgagg atcctacaga ccctactgat    4500
ccgcaagatc cagcatcacc gcggacttca actgtaatta actacaaacc tcaatcaact    4560
gcttatcaac caagctctgt ccaaaaaacg ttaccaaata cgggagtaac aaacaatgct    4620
tatatgcctt tacttggtat tattggctta gttactagtt ttagtttgct tggcttaaag    4680
gctaagaaag attga                                                     4695
```

<210> SEQ ID NO 21
<211> LENGTH: 1561
<212> TYPE: PRT
<213> ORGANISM: Streptococcus mutans

<400> SEQUENCE: 21

```
Met Lys Val Lys Lys Thr Tyr Gly Phe Arg Lys Ser Lys Ile Ser Lys
1               5                   10                  15

Thr Leu Cys Gly Ala Val Leu Gly Thr Val Ala Ala Ser Val Ala
            20                  25                  30

Gly Gln Lys Val Phe Ala Asp Glu Thr Thr Thr Ser Asp Val Asp
        35                  40                  45

Thr Lys Val Val Gly Thr Gln Thr Gly Asn Pro Ala Thr Asn Leu Pro
    50                  55                  60

Glu Ala Gln Gly Ser Ala Ser Lys Gln Ala Glu Gln Ser Gln Thr Lys
65                  70                  75                  80

Leu Glu Arg Gln Met Val His Thr Ile Glu Val Pro Lys Thr Asp Leu
                85                  90                  95

Asp Gln Ala Ala Lys Asp Ala Lys Ser Ala Gly Val Asn Val Gln
            100                 105                 110

Asp Ala Asp Val Asn Lys Gly Thr Val Lys Thr Ala Glu Glu Ala Val
        115                 120                 125

Gln Lys Glu Thr Glu Ile Lys Glu Asp Tyr Thr Lys Gln Ala Glu Asp
    130                 135                 140

Ile Lys Lys Thr Thr Asp Gln Tyr Lys Ser Asp Val Ala Ala His Glu
145                 150                 155                 160

Ala Glu Val Ala Lys Ile Lys Ala Lys Asn Gln Ala Thr Lys Glu Gln
                165                 170                 175

Tyr Gly Lys Asp Met Val Ala His Lys Ala Glu Val Glu Arg Ile Asn
            180                 185                 190
```

```
Ala Ala Asn Ala Ala Ser Lys Thr Ala Tyr Glu Ala Lys Leu Ala Gln
            195                 200                 205
Tyr Gln Ala Asp Leu Ala Ala Val Gln Lys Thr Asn Ala Ala Asn Gln
    210                 215                 220
Ala Ser Tyr Gln Lys Ala Leu Ala Ala Tyr Gln Ala Glu Leu Lys Arg
225                 230                 235                 240
Val Gln Glu Ala Asn Ala Ala Lys Ala Ala Tyr Asp Thr Ala Val
                245                 250                 255
Ala Ala Asn Asn Ala Lys Asn Thr Glu Ile Ala Ala Ala Asn Glu Glu
                260                 265                 270
Ile Arg Lys Arg Asn Ala Thr Ala Lys Ala Glu Tyr Glu Thr Lys Leu
                275                 280                 285
Ala Gln Tyr Gln Ala Glu Leu Lys Arg Val Gln Glu Ala Asn Ala Ala
    290                 295                 300
Asn Glu Ala Asp Tyr Gln Ala Lys Leu Thr Ala Tyr Gln Thr Glu Leu
305                 310                 315                 320
Ala Arg Val Gln Lys Ala Asn Ala Asp Ala Lys Ala Ala Tyr Glu Ala
                325                 330                 335
Ala Val Ala Ala Asn Asn Ala Lys Asn Ala Ala Leu Thr Ala Glu Asn
                340                 345                 350
Thr Ala Ile Lys Gln Arg Asn Glu Asn Ala Lys Ala Thr Tyr Glu Ala
                355                 360                 365
Ala Leu Lys Gln Tyr Glu Ala Asp Leu Ala Ala Val Lys Lys Ala Asn
    370                 375                 380
Ala Ala Asn Glu Ala Asp Tyr Gln Ala Lys Leu Thr Ala Tyr Gln Thr
385                 390                 395                 400
Glu Leu Ala Arg Val Gln Lys Ala Asn Ala Asp Ala Lys Ala Ala Tyr
                405                 410                 415
Glu Ala Ala Val Ala Ala Asn Asn Ala Ala Asn Ala Ala Leu Thr Ala
                420                 425                 430
Glu Asn Thr Ala Ile Lys Lys Arg Asn Ala Asp Ala Lys Ala Asp Tyr
                435                 440                 445
Glu Ala Lys Leu Ala Lys Tyr Gln Ala Asp Leu Ala Lys Tyr Gln Lys
    450                 455                 460
Asp Leu Ala Asp Tyr Pro Val Lys Leu Lys Ala Tyr Glu Asp Glu Gln
465                 470                 475                 480
Ala Ser Ile Lys Ala Ala Leu Ala Glu Leu Glu Lys His Lys Asn Glu
                485                 490                 495
Asp Gly Asn Leu Thr Glu Pro Ser Ala Gln Asn Leu Val Tyr Asp Leu
                500                 505                 510
Glu Pro Asn Ala Asn Leu Ser Leu Thr Thr Asp Gly Lys Phe Leu Lys
                515                 520                 525
Ala Ser Ala Val Asp Asp Ala Phe Ser Lys Ser Thr Ser Lys Ala Lys
    530                 535                 540
Tyr Asp Gln Lys Ile Leu Gln Leu Asp Asp Leu Asp Ile Thr Asn Leu
545                 550                 555                 560
Glu Gln Ser Asn Asp Val Ala Ser Ser Met Glu Leu Tyr Gly Asn Phe
                565                 570                 575
Gly Asp Lys Ala Gly Trp Ser Thr Thr Val Ser Asn Asn Ser Gln Val
                580                 585                 590
Lys Trp Gly Ser Val Leu Leu Glu Arg Gly Gln Ser Ala Thr Ala Thr
                595                 600                 605
```

```
Tyr Thr Asn Leu Gln Asn Ser Tyr Asn Gly Lys Lys Ile Ser Lys
610                 615                 620

Ile Val Tyr Lys Tyr Thr Val Asp Pro Lys Ser Lys Phe Gln Gly Gln
625                 630                 635                 640

Lys Val Trp Leu Gly Ile Phe Thr Asp Pro Thr Leu Gly Val Phe Ala
                645                 650                 655

Ser Ala Tyr Thr Gly Gln Val Glu Lys Asn Thr Ser Ile Phe Ile Lys
                660                 665                 670

Asn Glu Phe Thr Phe Tyr Asp Glu Asp Gly Lys Pro Ile Asn Phe Asp
                675                 680                 685

Asn Ala Leu Leu Ser Val Ala Ser Leu Asn Arg Glu Asn Asn Ser Ile
690                 695                 700

Glu Met Ala Lys Asp Tyr Thr Gly Lys Phe Val Lys Ile Ser Gly Ser
705                 710                 715                 720

Ser Ile Gly Glu Lys Asn Gly Met Ile Tyr Ala Thr Asp Thr Leu Asn
                725                 730                 735

Phe Arg Gln Gly Gln Gly Gly Ala Arg Trp Thr Met Tyr Thr Arg Ala
                740                 745                 750

Ser Glu Pro Gly Ser Gly Trp Asp Ser Ser Asp Ala Pro Asn Ser Trp
                755                 760                 765

Tyr Gly Ala Gly Ala Ile Arg Met Ser Gly Pro Asn Asn Ser Val Thr
770                 775                 780

Leu Gly Ala Ile Ser Ser Thr Leu Val Val Pro Ala Asp Pro Thr Met
785                 790                 795                 800

Ala Ile Glu Thr Gly Lys Lys Pro Asn Ile Trp Tyr Ser Leu Asn Gly
                805                 810                 815

Lys Ile Arg Ala Val Asn Leu Pro Lys Val Thr Lys Glu Lys Pro Thr
                820                 825                 830

Pro Pro Val Lys Pro Thr Ala Pro Thr Lys Pro Thr Tyr Glu Thr Glu
                835                 840                 845

Lys Pro Leu Lys Pro Ala Pro Val Ala Pro Asn Tyr Glu Lys Glu Pro
850                 855                 860

Thr Pro Pro Thr Arg Thr Pro Asp Gln Ala Glu Pro Lys Lys Pro Thr
865                 870                 875                 880

Pro Pro Thr Tyr Glu Thr Glu Lys Pro Leu Glu Pro Ala Pro Val Glu
                885                 890                 895

Pro Ser Tyr Glu Ala Glu Pro Thr Pro Thr Arg Thr Pro Asp Gln
                900                 905                 910

Ala Glu Pro Asn Lys Pro Thr Pro Pro Thr Tyr Glu Thr Glu Lys Pro
                915                 920                 925

Leu Glu Pro Ala Pro Val Glu Pro Ser Tyr Glu Ala Glu Pro Thr Pro
930                 935                 940

Pro Thr Pro Thr Pro Asp Gln Pro Glu Pro Asn Lys Pro Val Glu Pro
945                 950                 955                 960

Thr Tyr Glu Val Ile Pro Thr Pro Thr Asp Pro Val Tyr Gln Asp
                965                 970                 975

Leu Pro Thr Pro Pro Ser Ile Pro Thr Val His Phe His Tyr Phe Lys
                980                 985                 990

Leu Ala Val Gln Pro Gln Val Asn Lys Glu Ile Arg Asn Asn Asn Asp
                995                 1000                1005

Val Asn Ile Asp Arg Thr Leu Val Ala Lys Gln Ser Val Val Lys
        1010                1015                1020

Phe Gln Leu Lys Thr Ala Asp Leu Pro Ala Gly Arg Asp Glu Thr
```

-continued

```
                1025                1030                1035
Thr Ser Phe Val Leu Val Asp Pro Leu Pro Ser Gly Tyr Gln Phe
        1040                1045                1050
Asn Pro Glu Ala Thr Lys Ala Ala Ser Pro Gly Phe Asp Val Ala
        1055                1060                1065
Tyr Asp Asn Ala Thr Asn Thr Val Thr Phe Lys Ala Thr Ala Ala
        1070                1075                1080
Thr Leu Ala Thr Phe Asn Ala Asp Leu Thr Lys Ser Val Ala Thr
        1085                1090                1095
Ile Tyr Pro Thr Val Val Gly Gln Val Leu Asn Asp Gly Ala Thr
        1100                1105                1110
Tyr Lys Asn Asn Phe Ser Leu Thr Val Asn Asp Ala Tyr Gly Ile
        1115                1120                1125
Lys Ser Asn Val Val Arg Val Thr Thr Pro Gly Lys Pro Asn Asp
        1130                1135                1140
Pro Asp Asn Pro Asn Asn Tyr Ile Lys Pro Thr Lys Val Asn
        1145                1150                1155
Lys Asn Glu Asn Gly Val Val Ile Asp Gly Lys Thr Val Leu Ala
        1160                1165                1170
Gly Ser Thr Asn Tyr Tyr Glu Leu Thr Trp Asp Leu Asp Gln Tyr
        1175                1180                1185
Lys Asn Asp Arg Ser Ser Ala Asp Thr Ile Gln Gln Gly Phe Tyr
        1190                1195                1200
Tyr Val Asp Asp Tyr Pro Glu Glu Ala Leu Glu Leu Arg Gln Asp
        1205                1210                1215
Leu Val Lys Ile Thr Asp Ala Asn Gly Asn Glu Val Thr Gly Val
        1220                1225                1230
Ser Val Asp Asn Tyr Thr Ser Leu Glu Ala Ala Pro Gln Glu Ile
        1235                1240                1245
Arg Asp Val Leu Ser Lys Ala Gly Ile Arg Pro Lys Gly Ala Phe
        1250                1255                1260
Gln Ile Phe Arg Ala Asp Asn Pro Arg Glu Phe Tyr Asp Thr Tyr
        1265                1270                1275
Val Lys Thr Gly Ile Asp Leu Lys Ile Val Ser Pro Met Val Val
        1280                1285                1290
Lys Lys Gln Met Gly Gln Thr Gly Gly Ser Tyr Glu Asp Gln Ala
        1295                1300                1305
Tyr Gln Ile Asp Phe Gly Asn Gly Tyr Ala Ser Asn Ile Val Ile
        1310                1315                1320
Asn Asn Val Pro Lys Ile Asn Pro Lys Lys Asp Val Thr Leu Thr
        1325                1330                1335
Leu Asp Pro Ala Asp Thr Asn Asn Val Asp Gly Gln Thr Ile Pro
        1340                1345                1350
Leu Asn Thr Val Phe Asn Tyr Arg Leu Ile Gly Gly Ile Ile Pro
        1355                1360                1365
Ala Asn His Ser Glu Glu Leu Phe Glu Tyr Asn Phe Tyr Asp Asp
        1370                1375                1380
Tyr Asp Gln Thr Gly Asp His Tyr Thr Gly Gln Tyr Lys Val Phe
        1385                1390                1395
Ala Lys Val Asp Ile Thr Leu Lys Asn Gly Val Ile Ile Lys Ser
        1400                1405                1410
Gly Thr Glu Leu Thr Gln Tyr Thr Thr Ala Glu Val Asp Thr Thr
        1415                1420                1425
```

| | | | | | | | | | | |
|---|---|---|---|---|---|---|---|---|---|---|
|Lys|Gly|Ala|Ile|Thr|Ile|Lys|Phe|Lys|Glu|Ala|Phe|Leu|Arg|Ser|
| |1430| | | |1435| | | |1440| | | | | |

Val Ser Ile Asp Ser Ala Phe Gln Ala Glu Ser Tyr Ile Gln Met
    1445            1450            1455

Lys Arg Ile Ala Val Gly Thr Phe Glu Asn Thr Tyr Ile Asn Thr
    1460            1465            1470

Val Asn Gly Val Thr Tyr Ser Ser Asn Thr Val Lys Thr Thr Thr
    1475            1480            1485

Pro Glu Asp Pro Ala Asp Pro Thr Asp Pro Gln Asp Pro Ser Ser
    1490            1495            1500

Pro Arg Thr Ser Thr Val Ile Ile Tyr Lys Pro Gln Ser Thr Ala
    1505            1510            1515

Tyr Gln Pro Ser Ser Val Gln Lys Thr Leu Pro Asn Thr Gly Val
    1520            1525            1530

Thr Asn Asn Ala Tyr Met Pro Leu Leu Gly Ile Ile Gly Leu Val
    1535            1540            1545

Thr Ser Phe Ser Leu Leu Gly Leu Lys Ala Lys Lys Asp
    1550            1555            1560

<210> SEQ ID NO 22
<211> LENGTH: 4865
<212> TYPE: DNA
<213> ORGANISM: Streptococcus mutans

<400> SEQUENCE: 22

```
atttcagcaa aaattgacaa atcaaatcaa ttatattaca attttttaac gtatattaca      60
aaaatatatt tggaagattt attcagattt ggaggattta tgaaagtcaa aaaaacttac     120
ggttttcgta aaagtaaaat tagtaaaaca ctgtgtggtg ctgttctagg aacagtagca     180
gcagtctctg tagcaggaca aaaggttttt gccgatgaaa cgaccactac tagtgatgta     240
gatactaaag tagttggaac acaaactgga atccagcga ccaatttgcc agaggctcaa      300
ggaagtgcga gtaagcaagc tgaacaaagt caaaccaagc tggagagaca atggttcat      360
accattgaag tacctaaaac tgatcttgat caagcagcaa agatgctaa gtctgctggt      420
gtcaatgttg tccaagatgc cgatgttaat aaaggaactg ttaaaacagc tgaagaagca     480
gtccaaaaag aaactgaaat taagaagat tacacaaaac aagctgagga tattaagaag     540
acaacagatc aatataaatc ggatgtagct gctcatgagg cagaagttgc taaaatcaaa     600
gctaaaaatc aggcaactaa agaacagtat ggaaaagata tggtagctca taaagccgag     660
gttgaacgca ttaatgctgc aaatgctgcc agtaaaacag cttatgaagc taaattggct     720
caatatcaag cagatttagc agccgttcaa aaaaccaatg ctgccaatca agcatcctat     780
caaaaagccc ttgctgctta tcaggctgaa ctgaacgtg ttcaggaagc taatgcagcc      840
gccaaagccg cttatgatac tgctgtagca gcaataatg ccaaaaatac agaaattgcc      900
gctgccaatg aagaaattag aaaacgcaat gcaacggcca agctgaata tgagactaag     960
ttagctcaat atcaagctga actaaagcgt gttcaggaag ctaatgccgc aaacgaagca    1020
gactatcaag ctaaattgac cgcctatcaa acagagcttg ctcgcgttca gaaagccaat    1080
gcagatgcta aagcggccta tgaagcagct gtagcagcaa ataatgccaa aatgcggca     1140
cttacagctg aaaatactgc aattaagcaa cgcaatgaga atgctaaggc gacttatgaa    1200
gctgcactca gcaatatga ggctgatttg cagcggtga aaaagctaa tgccgcaaac      1260
gaagcagact atcaagctaa attgaccgcc tatcaaacag agctcgctcg cgttcaaaag    1320
```

```
gccaatgcgg atgctaaagc ggcctatgaa gcagctgtag cagcaaataa tgccgcaaat    1380
gcagcgctca cagctgaaaa tactgcaatt aagaagcgca atgcggatgc taaagctgat    1440
tacgaagcaa aacttgctaa gtatcaagca gatcttgcca aatatcaaaa agatttagca    1500
gactatccag ttaagttaaa ggcatacgaa gatgaacaag cttctattaa agctgcactg    1560
gcagaacttg aaaaacataa aaatgaagac ggaaacttaa cagaaccatc tgctcaaaat    1620
ttggtctatg atcttgagcc aaatgcgaac ttatctttga caacagatgg gaagttcctt    1680
aaggcttctg ctgtggatga tgcttttagc aaaagcactt caaaagcaaa atatgaccaa    1740
aaaattcttc aattagatga tctagatatc actaacttag aacaatctaa tgatgttgct    1800
tcttctatgg agctttatgg caattttggt gataaagctg gctggtcaac gacagtaagc    1860
aataactcac aggttaaatg gggatcggta cttttagagc gcggtcaaag cgcaacagct    1920
acatacacta acctgcagaa ttcttattac aatggtaaaa agatttctaa aattgtctac    1980
aagtatacag tggaccctaa gtccaagttt caaggtcaaa aggtttggtt aggtattttt    2040
accgatccaa ctttaggtgt ttttgcttcc gcttatacag gtcaagttga aaaaaacact    2100 tctatttttta ttaaaaatga attcactttc tatgacgaag atggaaaacc aattaatttt    2160
gataatgccc ttctatcagt agcttctctt aaccgagaaa ataattctat tgagatggcc    2220
aaagattata cgggtaaatt tgtcaaaatc tctggatcat ctatcggtga aaagaatggc    2280
atgatttatg ctacagatac tctcaacttt aggcagggtc aaggtggtgc tcgttggacc    2340
atgtatacca gagctagcga accgggatct ggctgggata gttcagatgc gcctaactct    2400
tggtatggtg ctggtgctat ccgcatgtct ggtcctaata acagtgtgac tttgggtgct    2460
atctcatcaa cacttgttgt gcctgctgat cctacaatgg caattgaaac cggcaaaaaa    2520
ccaaatattt ggtattcatt aaatggtaaa atccgtgcgg ttaatcttcc taaagttact    2580
aaggaaaaac ccacacctcc ggttaaacca acagctccaa ctaaaccaac ttatgaaaca    2640
gaaaagccat taaaaccggc accagtagct ccaaattatg aaaaggagcc aacaccaccg    2700
acaagaacac cggatcaagc agagccaaag aaacccactc cgccgaccta tgaaacagaa    2760
aagccgttgg agccagcacc tgttgagcca agctatgaag cagagccaac accgccgaca    2820
aggacaccgg atcaggcaga gccaaataaa cccacaccgc cgacctatga acagaaaag    2880 ccgttggagc cagcacctgt tgagccaagc tatgaagcag agccaacgcc accgacacca    2940
acaccagatc aaccagaacc aaacaaacct gttgagccaa cttatgaggt tattccaaca    3000
ccgccgactg atcctgttta tcaagatctt ccaacacctc catctatacc aactgttcat    3060
ttccattact ttaaactagc tgttcagccg caggttaaca agaaattag aaacaataac    3120 gatgttaata ttgacagaac tttggtggct aaacaatctg ttgttaagtt ccagctgaag    3180
acagcagatc tccctgctgg acgtgatgaa acaacttcct ttgtcttggt agatcccctg    3240
ccatctggtt atcaatttaa tcctgaagct acaaaagctg ccagccctgg ctttgatgtc    3300
gcttatgata atgcaactaa tacagtcacc ttcaaggcaa ctgcagcaac tttggctacg    3360
tttaatgctg atttgactaa gtcagtggca acgatttatc caacagtggt cggacaagtt    3420
cttaatgatg gcgcaactta taagaataat ttctcgctca cagtcaatga tgcttatggc    3480
attaaatcca atgttgttcg ggtgacaact cctggtaaac caaatgatcc agataaccca    3540
aataataatt acattaagcc aactaaggtt aataaaaatg aaaatggcgt tgttattgat    3600
ggtaaaacag ttcttgccgg ttcaacgaat tattatgagc taacttggga tttggatcaa    3660
```

```
tataaaaacg accgctcttc agcagatacc attcaacaag gattttacta tgtagatgat    3720
tatccagaag aagcgcttga attgcgtcag gatttagtga agattacaga tgctaatggc    3780
aatgaagtta ctggtgttag tgtggataat tatactagtc ttgaagcagc ccctcaagaa    3840
attagagatg ttcttttctaa ggcaggaatt agacctaaag gtgctttcca aattttccgt    3900
gccgataatc caagagaatt ttatgatact tatgtcaaaa ctggaattga tttgaagatt    3960
gtatcaccaa tggttgttaa aaaacaaatg ggacaaacag gcgggagtta tgaagatcaa    4020
gcttaccaaa ttgactttgg taatggttat gcatcaaata tcgttatcaa taatgttcct    4080
aagattaacc ctaagaaaga tgtgacctta acacttgatc cggctgatac aaataatgtt    4140
gatggtcaga ctattccact taatacagtc tttaattacc gtttgattgg tggcattatc    4200
cctgcaaatc actcagaaga actctttgaa tacaatttct atgatgatta tgatcaaaca    4260
ggagatcact atactggtca gtataaagtt tttgccaagg ttgatatcac tcttaaaaac    4320
ggtgttatta tcaagtcagg tactgagtta actcagtata cgacagcgga agttgatacc    4380
actaaaggtg ctatcacaat taagttcaag gaagcctttc tgcgttctgt ttcaattgat    4440
tcagccttcc aagctgaaag ttatatccaa atgaaacgta ttgcggttgg tacttttgaa    4500
aatacctata ttaatactgt caatggggta acttacagtt caaatacagt gaaaacaact    4560
actcctgagg atcctgcaga ccctactgat ccgcaagatc catcatcacc gcggacttca    4620
actgtaatta tctacaaacc tcaatcaact gcttatcaac caagctctgt ccaaaaaacg    4680
ttaccaaata cgggagtaac aaacaatgct tatatgcctt tacttggtat tattggctta    4740
gttactagtt ttagtttgct tggcttaaag gctaagaaag attgacagca tagatattac    4800
attagaatta aaaagtgaga tgaagcgata aatcacagat tgagctttta tctcattttt    4860
tgatt                                                                4865

<210> SEQ ID NO 23
<211> LENGTH: 330
<212> TYPE: PRT
<213> ORGANISM: Neisseria meningitidis

<400> SEQUENCE: 23

Met Lys Thr Ser Ile Arg Tyr Ala Leu Leu Ala Ala Ala Leu Thr Ala
1               5                   10                  15

Ala Thr Pro Ala Leu Ala Asp Ile Thr Val Tyr Asn Gly Gln His Lys
            20                  25                  30

Glu Ala Ala Gln Ala Val Ala Asp Ala Phe Thr Arg Ala Thr Gly Ile
        35                  40                  45

Lys Val Lys Leu Asn Ser Ala Lys Gly Asp Gln Leu Ala Gly Gln Ile
    50                  55                  60

Lys Glu Glu Gly Ser Arg Ser Pro Ala Asp Val Phe Tyr Ser Glu Gln
65                  70                  75                  80

Ile Pro Ala Leu Ala Thr Leu Ser Ala Ala Asn Leu Leu Glu Pro Leu
                85                  90                  95

Pro Ala Ser Thr Ile Asn Glu Thr Arg Gly Lys Gly Val Pro Val Ala
            100                 105                 110

Ala Lys Lys Asp Trp Val Ala Leu Ser Gly Arg Ser Arg Val Val Val
        115                 120                 125

Tyr Asp Thr Arg Lys Leu Ser Glu Lys Asp Leu Glu Lys Ser Val Leu
    130                 135                 140

Asn Tyr Ala Thr Pro Lys Trp Lys Asn Arg Ile Gly Tyr Ala Pro Thr
145                 150                 155                 160
```

Ser Gly Ala Phe Leu Glu Gln Val Val Ala Ile Val Lys Leu Lys Gly
            165                 170                 175

Glu Ala Ala Ala Leu Lys Trp Leu Lys Ala Leu Lys Glu Tyr Gly Lys
        180                 185                 190

Pro Tyr Ala Lys Asn Ser Val Ala Leu Gln Ala Val Glu Asn Gly Glu
    195                 200                 205

Ile Asp Ala Ala Leu Ile Asn Asn Tyr Tyr Trp His Ala Phe Ala Arg
210                 215                 220

Glu Lys Gly Val Gln Asn Val His Thr Arg Leu Asn Phe Val Arg His
225                 230                 235                 240

Arg Asp Pro Gly Ala Leu Val Thr Tyr Ser Gly Ala Val Leu Lys Ser
                245                 250                 255

Ser Gln Asn Lys Asp Glu Ala Lys Lys Phe Val Ala Phe Leu Ala Gly
            260                 265                 270

Lys Glu Gly Gln Arg Ala Leu Thr Ala Val Arg Ala Glu Tyr Pro Leu
        275                 280                 285

Asn Pro His Val Val Ser Thr Phe Asn Leu Glu Pro Ile Ala Lys Leu
    290                 295                 300

Glu Ala Pro Gln Val Ser Ala Thr Thr Val Ser Glu Lys Glu His Ala
305                 310                 315                 320

Thr Arg Leu Leu Glu Gln Ala Gly Met Lys
                325                 330

<210> SEQ ID NO 24
<211> LENGTH: 1072
<212> TYPE: DNA
<213> ORGANISM: Neisseria meningitidis

<400> SEQUENCE: 24
atgaaaacat ctatccgata cgcactgctt gccgcagccc tgaccgccgc aaccccgcg      60 ctggcagaca ttaccgtgta caacggccaa cacaaagaag cagcacaagc cgttgcagat    120
gcctttaccc gggctaccgg catcaaagtc aaactcaaca gtgccaaagg cgaccagctt    180
gccggtcaaa tcaaagaaga aggcagccga agccccgccg acgtattcta ttccgaacaa    240
atcccggcac tcgccaccct ttccgcagcc aacctcctag agccctgcc cgcctccacc     300 atcaacgaaa cacgcggcaa aggcgtgccg gttgccgcca aaaagactg gtggcactg      360 agcggacgtt cgcgcgtcgt cgtttacgac acccgcaaac tgtctgaaaa agatttggaa    420
aaatccgtcc tgaattacgc cacgccgaaa tggaaaaacc gcatcggtta cgcccccact    480
tccggcgcgt tcttggaaca ggttgtcgcc atcgtcaaac tgaaaggcga agcggccgca    540
ttgaaatggc tcaaagcact gaaagaatac ggcaagcctt acgctaaaaa ctccgtcgcc    600
cttcaagcgg ttgaaaacgg cgaaatcgat gccgccctca tcaacaacta ctactggcac    660
gctttcgcgc gtgaaaaagg cgtacaaaat gtccacaccc gcctgaattt cgtccgccac    720
agagatcccg gcgcactcgt tacctattcc ggcgcagtgt taaaatcctc ccaaaacaag    780
gatgaggcga aaaaattcgt cgccttcctc gccggcaagg aaggacagcg cgccctgacc    840
gccgtccgtg ccgaatatcc tttgaatccg cacgtggtat ccactttcaa tttggaaccc    900
atcgccaagt tggaagcacc ccaagtgtcc gccaccactg tttccgaaaa agaacacgcc    960
acccggctgc ttgagcaagc cggtatgaaa taagccgttt cggattgtc aaacgggtgg    1020 acatttatac tgtccgcccg ttttgccgat gaaaaacact atgtctccta aa            1072

PRODUCTION OF ENTERITIS EVOKING CAUSAL FACTOR BY HIGHLY PATHOGENIC ORAL BACTERIA AND HIGH SENSITIVITY DETECTION METHOD THEREFOR

RELATED APPLICATION

This application is a national stage filing under 35 U.S.C. §371 of international application PCT/JP2011/055688, filed Mar. 10, 2011, the disclosure of which is incorporated by reference herein in its entirety.

TECHNICAL FIELD

The present invention relates to a method of detecting an oral bacterium that aggravates inflammatory digestive tract disorders, in particular inflammatory bowel disease (IBD).

BACKGROUND ART

Inflammatory bower disease (IBD) is a chronic and intractable inflammatory disease of the intestine, and is principally classified into ulcerative colitis and Crohn's disease. In Japan, the number of patients with IBD in 2003 (the number of certified patients, because IBD is designated to be an intractable disease) is approximately 80 thousands patients with ulcerative colitis and approximately 20 thousands patients with Crohn's disease. However, the number of patients is steadily increasing due to Westernized dietary habit; the number of patients in 2003 is 20 times that in 1980 (the number of patients was approximately 5 thousands). In the future, it is expected that the number of young patients increases as well due to further Westernized dietary habit, and there is no doubt about a further increase in the number of patients.

It is indicated that IBD is caused by genetic predisposition, high fat and high protein diet, abnormality in the immune system, and intestinal bacteria, etc., but risk factors of the onset of IBD have not yet been clarified. However, abnormality in the immune system is considered to play an important role in the disease onset.

There is no established therapeutic method for IBD, and diet and rest are applied as general therapy, and steroids and immunosuppressive agents are administered as drug therapy; in addition, antibacterial agents such as Sarazopirin and mesalazine as well as antibiotics may have effects in some cases. Based on these, involvement of intestinal bacteria is indicated, but to date there has been no convincing evidence that a specific intestinal bacterium leads to the onset of disease symptoms.

In recent years, an oral bacterium as a major pathogenic bacterium of caries, i.e., *Streptococcus mutans* (*S. mutans*) as a kind of Mutans streptococci, is known to be a causative organism of bacteremia and infective endocarditis. In addition, since bacterial DNA of *S. mutans* was detected from specimens of heart valve and aortic aneurysm, its association with circulatory diseases has been reported (Non-patent Literature 1). However, there has been no report on the involvement of oral bacteria in inflammation of the digestive tract such as inflammatory bowel disease.

CITATION LIST

Non-Patent Literature

Non-patent Literature 1: Nakano et al., 2008, Japanese Dental Science Review, 44: 29-37.

SUMMARY OF INVENTION

Problems to be Solved by the Invention

An object of the present invention is to provide a system to identify responsible factors that aggravate inflammatory digestive tract disorders, and to rapidly and readily specify a patient having a risk of aggravation of inflammatory digestive tract disorders.

Means for Solving the Problems

The inventors have already found that hemorrhage is aggravated in a subject who has been infected with a particular strain of *Streptococcus mutans* (*S. mutans*), and that the most severe virulence of hemorrhage aggravation is exerted by bacterial strains that do not carry a protein antigen (PA, also known as PAC, SpaP, antigen I/II, antigen B, SR, IF, P1, MSL-1), i.e., a major bacterial surface protein having a molecular weight of about 190 kDa, and that carry a collagen binding protein (CBP, also known as Cnm) having a molecular weight of about 120 kDa; the inventors have filed a patent application of an invention on the basis of these findings (JP A 2009-88239).

*Streptococcus mutans* is known to have four serotypes (c, e, f and k). The inventors revealed that intravenous administration of some of different *S. mutans* strains inhibits spontaneous hemostatic action and induces aggravation of hemorrhage, when mild cerebral hemorrhage has been induced by damaging the middle cerebral artery. Of the *S. mutans* strains, generally c-serotype strains are isolated from the oral cavity, and their standard strain MT8148 (serotype c) (Minami et al., 1990, Oral Microbiol. Immunol., 5: 189-194) does not cause such effects; however, there are strains among k-serotype strains that evoke aggravation of inflammatory digestive tract disorders. In particular, TW295 strain and TW871 strain (Nakano et al., 2004, Journal of Clinical Microbiology, 42(1): 198-202), and SA53 strain (Nakano et al., 2007, J. Clin. Microbiol., 45: 2614-2625) cause a significant hemorrhage aggravation.

The inventors have found that these highly virulent *S. mutans* strains lack PA, a major bacterial surface protein, and that among PA-deleted strains, the virulence of the strains carrying CBP, another bacterial surface protein, is particularly high. Moreover, the inventors have confirmed that when CBP-encoding gene of TW295 strain has been deleted by genetic engineering, hemorrhage aggravation similar to that caused by TW295 strain is not observed, and that when PA-encoding gene of MT8148 strain has been deleted, hemorrhage aggravation is observed; thus the inventors have confirmed that CBP and PA are involved in hemorrhage aggravation of *S. mutans*.

Recently, the inventors have additionally recognized that abnormal reddening occurs in the intestinal tract of a mouse administered with said bacterial strain that causes hemorrhage aggravation, and found a significant association between oral bacteria and inflammatory bowel disease (IBD); after further promotion of the research, the inventors accomplished the present invention.

Namely, the present invention relates to a method of detecting an oral bacterium that aggravates inflammatory digestive tract disorder, comprising detecting PA and/or CBP of oral bacteria in a sample, wherein the presence of the oral bacterium that aggravates inflammatory digestive tract disorder is determined when PA is not detected and/or CBP is detected.

Furthermore, the present invention relates to a method of screening a subject at a high risk of aggravation of inflammatory digestive tract disorder, comprising detecting PA and/or CBP of oral bacteria in a biological sample obtained from a subject, wherein a high risk of aggravation of inflammatory digestive tract disorder is determined when PA is not detected and/or CBP is detected.

In addition, the present invention relates to a method of judging the risk of aggravation of inflammatory digestive tract disorder in a subject, comprising detecting PA and/or CBP of oral bacteria in a biological sample obtained from a subject, wherein a high risk of aggravation of inflammatory digestive tract disorder in the subject is determined when PA is not detected and/or CBP is detected.

Furthermore, the present invention relates to the method wherein the inflammatory digestive tract disorder is inflammatory bowel disease.

In addition, the present invention relates to the method wherein the oral bacterium is *Streptococcus mutans*.

Furthermore, the present invention relates to the method wherein the genotype of *Streptococcus mutans* is cnm(+).

In addition, the present invention relates to the method wherein the serotype of *Streptococcus mutans* is f-type or k-type.

Furthermore, the present invention relates to the method wherein the PA is selected from the group consisting of: (1) a polypeptide comprising the amino acid sequence of SEQ ID NO: 1, 17, 19, 21 or 23; (2) a polypeptide comprising one or more mutations in the polypeptide of (1), but having an equal function to the polypeptide of (1); (3) a polypeptide comprising an amino acid sequence encoded by a nucleic acid sequence that hybridizes with the nucleic acid sequence of SEQ ID NO: 2, 18, 20, 22 or 24 or its complementary sequence or its fragment under stringent conditions, and having an equal function to the polypeptide of (1); (4) a polypeptide comprising an amino acid sequence having 70% or more homology with the amino acid sequence of SEQ ID NO: 1, 17, 19, 21 or 23, and having an equal function to the polypeptide of (1).

In addition, the present invention relates to the method wherein the PA comprises a polypeptide consisting of the amino acid sequence of SEQ ID NO: 1, 17, 19, 21 or 23.

Furthermore, the present invention relates to the method wherein the CBP is selected from the group consisting of: (1) a polypeptide comprising the amino acid sequence of SEQ ID NO: 5 or 9; (2) a polypeptide comprising one or more mutations in the polypeptide of (1), but having an equal function to the polypeptide of (1); (3) a polypeptide comprising an amino acid sequence encoded by a nucleic acid sequence that hybridizes with the nucleic acid sequence of SEQ ID NO: 6 or 10 or its complementary sequence or its fragment under stringent conditions, and having an equal function to the polypeptide of (1); (4) a polypeptide comprising an amino acid sequence having 70% or more homology with the amino acid sequence of SEQ ID NO: 5 or 9, and having an equal function to the polypeptide of (1).

In addition, the present invention relates to the method wherein the CBP comprises a polypeptide consisting of the amino acid sequence of SEQ ID NO: 5 or 9.

Furthermore, the present invention relates to a reagent for detection of an oral bacterium that aggravates inflammatory digestive tract disorder, comprising an oral bacterial PA-detecting agent and/or CBP-detecting agent.

In addition, the present invention relates to an oral bacterial PA-specific antibody for detection of an oral bacterium that aggravates inflammatory digestive tract disorder.

Furthermore, the present invention relates to a kit for detecting an oral bacterium that aggravates inflammatory digestive tract disorder and/or for screening a subject at a high risk of aggravation of inflammatory digestive tract disorder and/or for determining the risk of aggravation of inflammatory digestive tract disorder in a subject, comprising at least a PA-detecting reagent, and a CBP-detecting reagent.

Advantageous Effects of Invention

The present invention enables rapid and simple diagnosis of the risk of causing aggravation of inflammatory digestive tract disorder in an individual. Also, the method of the present invention enables detection of responsible factors of aggravation of inflammatory digestive tract disorder using readily-available biological samples such as saliva and plaque, without employing any special analyzers. As such, the present invention allows to specify a high-risk population of aggravation of inflammatory digestive tract disorder, and to treat the individuals belonging to this population with a regimen such as removing virulent bacteria and advising dental hygiene, thereby effectively preventing aggravation of inflammatory digestive tract disorder.

BRIEF DESCRIPTION OF DRAWINGS

FIG. 1 is a flow-chart of a system to detect a *S. mutans* strain which may cause aggravation of inflammatory digestive tract disorders.

FIG. 2 is a scheme of methods of culturing and detecting *S. mutans*.

FIG. 5 shows photographs of typical examples of individual mouse (top) and the large intestine (bottom) in the control group and TW295 administration group on day 11-15 following administration.

FIG. 11 shows photographs of observation of localization in the tissue of a *Streptococcus mutans* TW295-GFP strain that expresses GFP proteins.

FIG. 14 is a graph showing results of investigation of optimum conditions for culturing *S. mutans* (culturing in an aerobic/anaerobic condition, concentration of antibiotics, nutrient concentrations).

DESCRIPTION OF EMBODIMENTS

Figure 3:
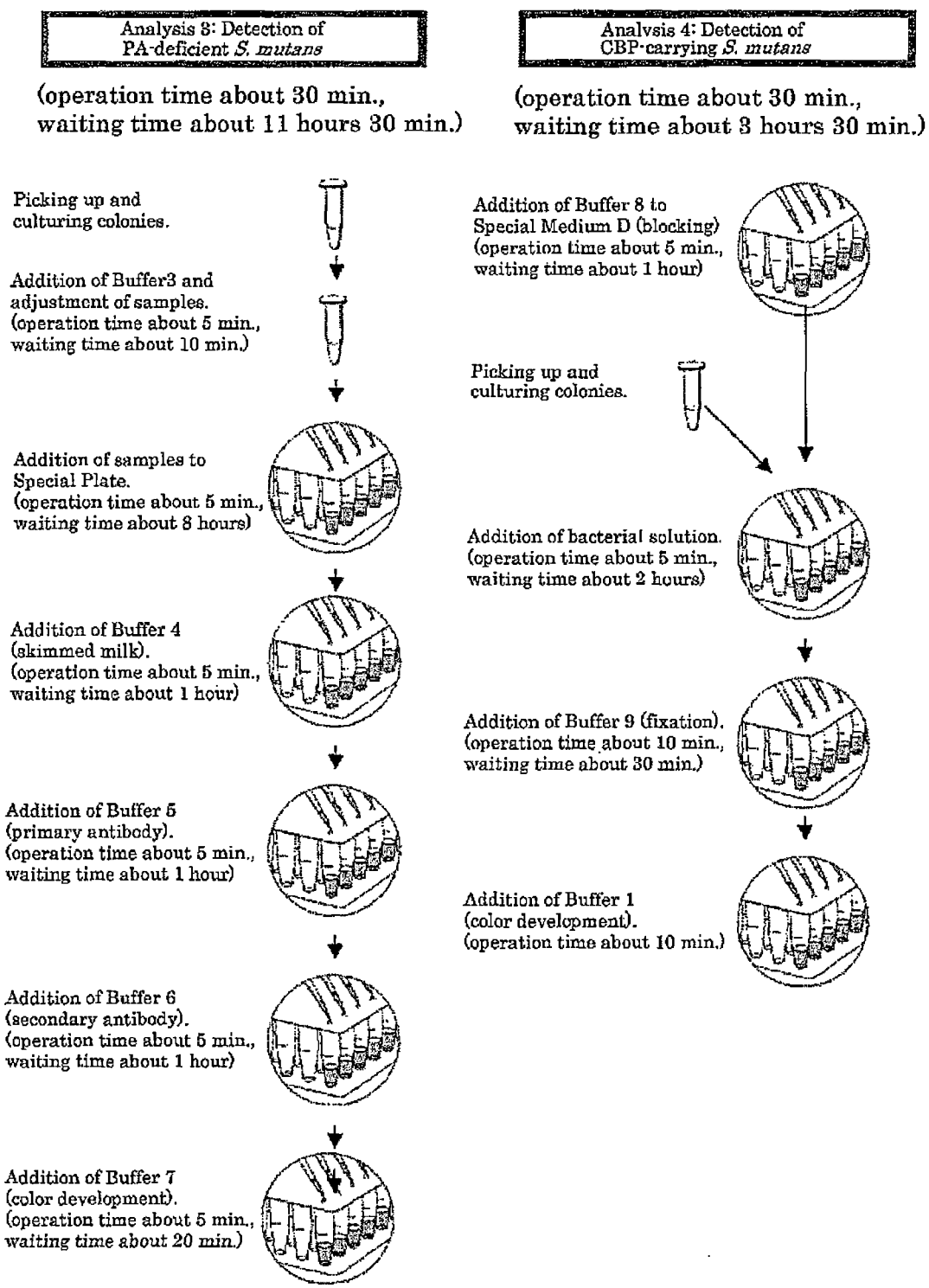
FIG. 3 is a scheme of methods of detecting PA-deleted *S. mutans* and CBP-carrying *S. mutans*.

The present invention provides a method of detecting an oral bacterium that causes aggravation of inflammatory digestive tract disorder, the method comprising detecting PA and/or CBP of oral bacteria in a sample, wherein the presence of the oral bacterium that causes aggravation of inflammatory digestive tract disorder is determined by nondetection of PA and/or detection of CBP.

The present invention provides, in another embodiment, a method of screening a subject at a high risk of aggravation of inflammatory digestive tract disorder, the method comprising detecting PA and/or CBP of oral bacteria in a biological sample obtained from a subject, wherein a high risk of aggravation of inflammatory digestive tract disorder is determined by nondetection of PA and/or detection of CBP.

The present invention further provides, in another embodiment, a method of determining the risk of aggravation of inflammatory digestive tract disorder in a subject, the method comprising detecting PA and/or CBP of oral bacteria in a biological sample obtained from a subject, wherein a high risk of aggravation of inflammatory digestive tract disorder is determined in the subject by nondetection of PA and/or detection of CBP.

Inflammatory digestive tract disorders referred to in this specification intend to include inflammatory diseases in any digestive tract and digestive gland and their associated organs. More specifically, they include inflammatory disease of the digestive tract such as oral cavity, pharynx, esophagus, stomach, small intestine (duodenum, jejunum, ileum), large intestine (cecum, appendix, colon (ascending colon, transverse colon, descending colon, sigmoid colon), rectum) and anus, as well as salivary glands that secrete saliva, pancreas that secretes pancreatic juice, and liver and gallbladder that secrete bile. Their typical example includes inflammatory bowel disease (IBD).

PA (protein antigen) is a surface protein of approximately 190 kDa found in MT8148 strain, a *S. mutans* wild-type strain, and also known in various other names such as PAc (protein antigen c), SpaP, antigen I/II and antigen B, P1 and MSL-1. PA polypeptide comprises 3 alanine-rich repeat domains (A-region) at N-terminal side and 3 proline-rich repeat domains (P-region) at central part, and has cell wall/membrane-spanning domain at C-terminal. It has been reported that A-regions are involved in the attachment of bacterial cells to the teeth (Matsumoto-Nakano et al., 2008, Oral Microbiology and Immunology, 23:265-270). Also, there have been reports that PA is involved in infective endocarditis by *S. mutans* (Nakano et al., 2008, Japanese Dental Science Review, 44: 29-37); that an antibody against PA inhibits the attachment of bacterial cells to a hydroxyapatite substrate (Kawato et al., 2008, Oral Microbiology and Immunology, 23:14-20); and that an antiserum against PA is useful as a vaccine for dental caries (Okahashi et al., 1989, Molecular Microbiology, 3(2): 221-228). Although there is a region between A-region and P-region of PA, in which amino acid sequences are highly variable among strains (for example, in MT8148 strain, residues from 679 to 827), the repeat domain and membrane-spanning domain are highly conserved among strains.

Also, it is reported that a high percentage of strains of serotype k, which are often detected in patients with infective endocarditis, lack PA, and that both the hydrophobicity of the bacterial cell and sensitivity to phagocytosis are low in this serotype (Nakano et al., 2008, Journal of Dental Research, 87(10): 964-968).

Known PA includes, for example, PA of serotype c MT8148 (DDBJ Accession No.: X14490, amino acids: SEQ ID NO: 1, nucleic acids: SEQ ID NO: 2), PA of LJ23 strain (DDBJ Accession No.: AB364261, amino acids: SEQ ID NO: 17, nucleic acids: SEQ ID NO: 18), PA of SA98 strain (DDBJ Accession No.: AB364285, amino acids: SEQ ID NO: 19, nucleic acids: SEQ ID NO: 20), as well as spaP gene of antigen I/II (DDBJ Accession No.: X17390, Kelly et al., 1989, FEBS Lett. 258(1), 127-132, amino acids: SEQ ID NO: 21, nucleic acids: SEQ ID NO: 22) and a meningococcus *Neisseria meningitidis* iron binding protein fbp gene (X53469, Berish et al., 1990, Nucleic Acid Research, 18(15): 4596-4596, amino acids: SEQ ID NO: 23, nucleic acids: SEQ ID NO: 24).

CBP, i.e., another anchor protein of *S. mutans* (also denoted as Cnm), is a Type I collagen binding protein of approximately 120 kDa molecular weight, and has a collagen binding domain (CBD, residues from 152 to 316), B repeat domain (residues from 328 to 455) and LPXTG motif (residues from 507 to 511) (Sato et al., 2004, Journal of Dental Research, 83(7): 534-539). CBP gene-carrying frequency of *S. mutans* present in the oral cavity is about 10 to 20%, and CBP-positive strain is predominantly detected in serotypes f and k (Nakano et al., 2007, J. Clin. Microbiol., 45: 2616-2625).

A study by the inventors revealed that, for CBP of serotype k TW295 strain (DDBJ Accession No.: AB102689, amino acids: SEQ ID NO: 3, nucleic acids: SEQ ID NO: 4), CBD (amino acids: SEQ ID NO: 5, nucleic acids: SEQ ID NO: 6) and LPXTG motif are highly conserved among strains, whereas the number of repeats in the B repeat domain varies among strains.

In one embodiment of the present invention, PA is defined as:
(1) a polypeptide comprising the amino acid sequence of SEQ ID NO: 1, 17, 19, 21 or 23;
(2) a polypeptide comprising one or more, preferably 1 to 20, 1 to 15, 1 to 10, or one or several mutations in the polypeptide of (1), but having an equal function to the polypeptide of (1);
(3) a polypeptide comprising an amino acid sequence encoded by a nucleic acid sequence that hybridizes under stringent conditions with the nucleic acid sequence of SEQ ID NO: 2, 18, 20, 22 or 24 or its complementary sequence or its fragment, and having an equal function to the polypeptide of (1); or
(4) a polypeptide comprising an amino acid sequence having 70% or more, preferably 80% or more, more preferably 90% or more, still more preferably 95% or more homology to the amino acid sequence of SEQ ID NO: 1, 17, 19, 21 or 23, and having an equal function to the polypeptide of (1).

Preferably, PA comprises a polypeptide consisting of the amino acid sequence of SEQ ID NO: 1, 17, 19, 21 or 23. More preferably, PA comprises a polypeptide consisting of the amino acid sequence of SEQ ID NO: 1.

PA that can be used in the method of the present invention may be a polypeptide comprising one or more amino acid mutations (deletion, substitution, addition), as long as it comprises an amino acid sequence encoded by a nucleic acid sequence that hybridizes under stringent conditions with the nucleic acid sequence of SEQ ID NO: 2, 18, 20, 22 or 24 (nucleic acid sequence that encodes PA protein) or its complementary sequence or its fragment, and has an equal function to a polypeptide comprising the amino acid sequence of SEQ ID NO: 1, 17, 19, 21 or 23 (amino acid sequence of PA protein). Mutations may be naturally occurring mutations or mutations generated by any known procedures, e.g., cleavage or insertion of a nucleic acid by restriction enzyme, site-specific mutagenesis, or radiation or ultraviolet irradiation. Moreover, the number of mutated amino acids may be 1 to 20, 1 to 15, 1 to 10, or 1 to several, for example.

Furthermore, in one embodiment of the present invention, CBP is defined as:
(1) a polypeptide comprising the amino acid sequence of SEQ ID NO: 5 or 9;
(2) a polypeptide comprising one or more, preferably 1 to 20, 1 to 15, 1 to 10, or one or several mutations in the polypeptide of (1), but having an equal function to the polypeptide of (1);
(3) a polypeptide comprising an amino acid sequence encoded by a nucleic acid sequence that hybridizes under stringent conditions with the nucleic acid sequence of SEQ ID NO: 6 or 10 or its complementary sequence or its fragment, and having an equal function to the polypeptide of (1); or
(4) a polypeptide comprising an amino acid sequence having 70% or more, preferably 80% or more, more preferably 90% or more, still more preferably 95% or more homology with the amino acid sequence of SEQ ID NO: 5 or 9, and having an equal function to the polypeptide of (1).

CBP polypeptide that can be used in the method of the present invention may be a polypeptide comprising one or more, e.g., 1 to 20, 1 to 15, 1 to 10, or one or several amino acid mutations (deletion, substitution, addition), as long as it comprises an amino acid sequence encoded by a nucleic acid sequence that hybridizes under stringent conditions with the nucleic acid sequence of SEQ ID NO: 6 or 10 (nucleic acid sequence encoding CBD of S. mutans TW295 strain or TW871 strain) or its complementary sequence or its fragment, and has an equal function to a polypeptide comprising the amino acid sequence of SEQ ID NO: 5 or 9 (CBD amino acid sequence of S. mutans TW295 strain or TW871 strain).

For instance, CBP polypeptide may be a polypeptide comprising an amino acid sequence encoded by a nucleic acid sequence that hybridizes under stringent conditions with the nucleic acid sequence of SEQ ID NO: 4 or 8 (a nucleic acid sequence encoding CBP of S. mutans TW295 strain or TW871 strain) or its complementary sequence or its fragment, and has an equal function to a polypeptide comprising the amino acid sequence of SEQ ID NO: 3 or 7 (an amino acid sequence of CBP protein of S. mutans TW295 strain or TW871 strain).

Preferably, CBP comprises a polypeptide consisting of the amino acid sequence of SEQ ID NO: 5 or 9.

Whether or not a PA mutant or CBP mutant has a function equal to that of PA or CBP may be confirmed using any known means. For instance, the ability of PA mutant making the bacterial cell adhere to a hydroxyapatite substrate may be determined by raising a specific antibody against the mutant peptide by a known method, and assaying the inhibition of adhesion of bacteria to the hydroxyapatite by said antibody in accordance with a method described in Kawato et al., 2008, Oral Microbiology and Immunology, 23:14-20. Alternatively, the binding ability of a CBP mutant to Type I collagen may be determined by collagen binding assay described in Nomura et al., 2009, J. Med. Microbiol., 58(4): 469-475. By such means, the ability of a mutant can be assessed in comparison with an appropriate negative control, or with PA or CBP as a positive control. For instance, a certain mutant is considered as a functional mutant when at least one function described above is better, e.g., 10% or more, 25% or more, 50% or more, 75% or more, or even 100% or more, than that of the negative control, and/or when said function is 1/100 or less, 1/50 or less, 1/25 or less, 1/10 or less, 1/5 or less, or even 1/2 or less, than that of the positive control.

Major bacterial species identified as oral bacteria that cause aggravation of inflammatory digestive tract disorders include mutans streptococci such as *Streptococcus mutans, Streptococcus sobrinus, Streptococcus cricetus, Streptococcus rattus, Streptococcus downei*; as well as *Streptococcus sanguinis, Streptococcus oralis, Streptococcus gordonii*, and *Streptococcus salivarius*. Particularly, *S. mutans* TW295 strain and TW871 strain would cause severe aggravation of inflammatory digestive tract disorders.

Screening of other bacteria that could induce aggravation of inflammatory digestive tract disorders can be carried out utilizing databases such as NCBI GenBank®, DDBJ (DNA Data Bank of Japan, http://www.ddbj.nig.ac.jp/) and EMBL, and publicly available search tools such as BLAST.

The present invention provides, in one embodiment, a reagent for detection of an oral bacterium that causes aggravation of inflammatory digestive tract disorder, comprising an oral bacterial PA-detecting agent and/or an oral bacterial CBP-detecting agent.

In one embodiment, the PA-detecting agent comprises an oral bacterial PA-specific antibody. Using the PA-specific antibody developed by the inventors, presence or absence of highly virulent *S. mutans* can be rapidly and easily detected. The PA-specific antibody is preferably an antibody or its fragment induced from a polypeptide comprising the amino acid sequence of SEQ ID NO: 1 or its immunogenic fragment. Alternatively, the PA-specific antibody may be an antibody or its fragment induced from a polypeptide having at least 80% homology with the amino acid sequence of SEQ ID NO: 1, 17, 19, 21 or 23, and having an immunogenicity to induce antibody production against a polypeptide comprising the amino acid sequence of SEQ ID NO: 1, 17, 19, 21 or 23. For example, a recombinant PA comprising the above polypeptide (see, e.g., Nakano et al., 2006, Microbes and Infection, 8:114-121) may be used as an antigen to produce a monoclonal or polyclonal antibody.

In one embodiment, the CBP detecting agent comprises a substrate (such as a microplate, test tube or slide glass) coated with Type I collagen. The binding ability of CBP to Type I collagen (Nomura et al., 2009, J. Med. Microbiol., 58 (4): 469-475) can be utilized to allow CBP-expressing bacterial cell to attach the substrate coated with Type I collagen, which can easily be detected.

In another embodiment, the CBP-detecting agent comprises a specific antibody against an oral bacterial CBP. The CBP-specific antibody may be a specific antibody against the collagen binding domain of CBP, preferably, an antibody or its fragment induced from a polypeptide comprising the amino acid sequence of SEQ ID NO: 5 or 9, or its immunogenic fragment. Alternatively, the CBP-specific antibody may be an antibody or its fragment induced from a polypeptide having at least 80% homology with the amino acid sequence of SEQ ID NO: 5 or 9, and having an immunogenicity to induce an antibody production against a polypeptide comprising the amino acid sequence of SEQ ID NO: 5 or 9.

In the present invention, the antibody fragment comprises, for example, without limitation, various functional fragments such as Fab, Fab', F(ab')2, scFv, dsFv (disulfide-stabilized V region fragment), and CDR-containing fragment.

The present invention provides, in one embodiment, a kit for detecting an oral bacterium that causes aggravation of inflammatory digestive tract disorder, and/or for screening a subject at a high risk of aggravation of inflammatory digestive tract disorder, and/or for the determination of the risk of aggravation of inflammatory digestive tract disorder in a subject. The kit comprises at least a PA-detecting reagent and a CBP-detecting reagent.

In one embodiment, the kit comprises as a PA-detecting reagent an oral bacterial PA-specific antibody.

In one embodiment, the kit comprises as a CBP-detecting reagent a substrate coated with Type I collagen (such as a microplate, test tube or slide glass).

In another embodiment, the kit comprises as a CBP-detecting reagent a CBP-specific antibody.

The kit of the present invention may further comprise one or more of the followings for culturing S. mutans:

An instrument for collecting saliva such as a spitz for collecting saliva (the material and shape is not particularly limited as long as it is sterilized and suitable for collecting and seeding).

A collecting instrument such as a dropper capable of collecting saliva of approximately 10 µl.

S. mutans selection medium (Special Medium A). For example, sterile substrate coated with MSB agar medium (Mitis-salivariusagar medium (e.g., Difco Laboratories) supplemented with an antibiotic (e.g., bacitracin (e.g., SIGMA-ALDRICH)) and sucrose (e.g., Wako Pure Chemical Industries, Ltd.)). The substrate is not particularly limited as long as it is such as a dish or well plate, though typically roughly a 24-well plate (e.g., 24 well with Lid MICROPLATE (IWAKI)) is used. Bacitracin is preferably used at about 100 unit/ml. Sucrose is preferably used at about 15%.

A sealing and/or deoxygenating instrument for culturing under an anaerobic condition, such as Anaero Pack® or a $CO_2$ chamber.

A sterile stick for picking up bacterial colonies (such as a toothpick or tip).

A liquid medium for culturing the picked-up colonies (Special Medium B). For example, sterilized Brain Heart Infusion (BHI) liquid medium (Difco Laboratories) contained in a disposable test tube.

The kit of the present invention may further comprise one or more of the followings for detecting S. mutans:

A collecting instrument suitable for collecting bacterial solution of approximately 10 µl such as a dropper.

A special medium for detecting S. mutans (Special Medium C). For example, a medium in which 100 µl of a sucrose (Wako Pure Chemical Industries, Ltd.)-containing BHI solution is added to a substrate. The substrate is not particularly limited as long as it is such as a well plate or test tube, though typically a 96-well plate (e.g., MULTI WELL PLATE for ELISA (SUMIRON)) is used. Sucrose is used at about 1%.

A wash buffer (Wash Buffer A: PBS solution or sterile water may be used, though preferably PBS solution is used.)

A Gram-positive bacteria detecting reagent (Buffer 1: for example, a solution in which about 0.5% crystal violet (e.g., Wako Pure Chemical Industries, Ltd.) as a Gram-positive bacteria detecting reagent is added to sterile distilled water.)

A mordanting reagent (Buffer 2: a suitable mordanting reagent may be selected depending on the bacteria detecting reagent. For example, 7% acetate (e.g., Wako Pure Chemical Industries, Ltd.) solution or sterile water may be used for the crystal violet, though preferably acetate solution is used.)

The kit of the present invention may further comprise one or more of the followings for detecting PA-deleted S. mutans:

A plate for detecting PA-deleted S. mutans. It is not particularly limited as long as it is a sterile well plate, though typically a 96-well plate (e.g., MICROTEST U-Bottom (BECTON DICKINSON)) is used.

A wash buffer (Wash Buffer B: a solution in which about 0.05% of a surfactant such as Triton X-100 (e.g., Wako Pure Chemical Industries, Ltd.) is added to PBS solution or sterile water. Preferably PBS solution is used.)

A buffer (Buffer 3: a mixture of Tris buffered saline (pH 6.8), 100 mM dithiothreitol (e.g., Wako Pure Chemical Industries, Ltd.) and 20% glycerin (e.g., Wako Pure Chemical Industries, Ltd.).)

A blocking solution (Buffer 4: a PBST solution containing approximately 5% of skimmed milk (e.g., BECTON DICKINSON).)

A primary antibody (Buffer 5: a PBST solution containing approximately 0.1% of anti-PA antiserum.)

A secondary antibody (Buffer 6: a PBST solution containing approximately 0.1% of an antibody against immunoglobulin of the primary antibody of the host (e.g., Dakopatts).)

A color-developing reagent (Buffer 7: AP (100 mM 2-amino-2-hydroxymethyl-1,3-propanediol, 5 mM magnesium chloride, 100 mM sodium chloride) buffer supplemented with NBT solution (Wako Pure Chemical Industries, Ltd.) at final concentration of 0.6% and BCIP solution (Wako Pure Chemical Industries, Ltd.) at final concentration of 0.33%.)

The kit of the present invention may further comprise one or more of the followings for detecting CBP-carrying S. mutans:

A special medium for detecting CBP-carrying S. mutans (Special Medium D: a mixed solution of 0.6% acetate-containing sterile distilled water and Type I collagen (Sigma) in 9:1 ratio contained in the Special Plate used in Analysis 3.)

A wash buffer (Wash Buffer A: PBS solution or sterile water may be used, though preferably PBS solution is used.)

A buffer (Buffer 8: Wash Buffer A containing approximately 5% bovine albumin (Sigma).)

A wash buffer (Wash Buffer C: PBS solution or sterile water containing a surfactant such as approximately 0.01% Tween 20 (Wako Pure Chemical Industries, Ltd.). Preferably, PBS solution is used.)

A fixative solution (Buffer 9: for example, sterile distilled water containing approximately 25% formaldehyde (Wako Pure Chemical Industries, Ltd.).)

A Gram-positive bacteria detecting reagent (e.g., above Buffer 1: a solution in which approximately 0.5% crystal violet (Wako Pure Chemical Industries, Ltd.) as a Gram-positive bacteria detecting reagent is added to sterile distilled water.)

A mordanting reagent (e.g., above Buffer 2: 7% acetate (e.g., Wako Pure Chemical Industries, Ltd.) solution or sterile water may be used, though preferably acetate solution is used.)

A skilled person in the art may appropriately adjust the concentration of the above-mentioned components, e.g., antiserum, secondary antibody, formaldehyde or crystal violet, to be optimum depending on experimental conditions.

The method of the present invention for detecting an oral bacterium that causes aggravation of inflammatory digestive tract disorder is carried out, specifically, in a scheme comprising the following four steps, for example as shown in FIGS. 1 to 3:

Analysis 1. Culturing of *S. mutans*

Analysis 2. Detection of *S. mutans*

Analysis 3. Detection of PA-deleted *S. mutans*

Analysis 4. Detection of CBP-carrying *S. mutans*

In Analysis 1, culturing of bacteria is carried out by the following procedures using for example instruments and reagents in the aforementioned kit for culturing mutans streptococci.

The saliva of a subject is collected in a small amount using a spitz for collecting saliva. 10 µl of the saliva is taken from the spitz using a dropper, plated on a *S. mutans* selection agar medium (e.g., the above-mentioned Special Medium A), and cultured at 37° C. for 48 hours, preferably under an anaerobic condition. After culturing, the presence of bacterial colonies is grossly confirmed, the colonies are picked up and added to a liquid medium (e.g., the above-mentioned Special Medium B) and cultured at 37° C. for 18 hours, then used for the following Analyses 2, 3 and 4. Preferably, rough colonies are picked up, since *S. mutans* forms rough colonies, whereas *S. sobrinus* forms smooth colonies.

In Analysis 2, detection of *S. mutans* is carried out by the following procedures using for example instruments and reagents in the aforementioned kit for detecting *S. mutans*.

10 µl of the bacterial solution cultured from the method of Analysis 1 is added to a medium (e.g., the above-mentioned Special Medium C), and incubated at 37° C. for 3 hours. The medium is washed with a wash buffer (e.g., the above Wash Buffer A) for three times, then left still about 15 minutes with the last wash buffer. The wash buffer is removed, and again the medium is washed with Wash Buffer A for once, then a buffer containing a Gram-positive bacteria staining reagent (e.g., above Buffer 1) is added and left still for 1 minute. It is washed with the wash buffer for three times, and a buffer containing a mordanting agent (e.g., above Buffer 2) is added. If the color of the medium changes, it is determined to be *S. mutans*-positive, if the color of the medium does not change, it is determined to be *S. mutans*-negative. A reagent in which a staining reagent and a mordanting agent are already combined may also be used.

In Analysis 3, detection of PA-deleted *S. mutans* is carried out by the following procedures using for example instruments and reagents in the aforementioned kit for detecting PA-deleted *S. mutans*.

(1) Sample Preparation

To the bacterial solution cultured by the method of Analysis 1 above a suitable buffer (e.g., the above-mentioned Buffer 3) is added, which is then immersed in boiling water for 10 minutes, and frozen if it is to be stored.

(2) Detection of PA-Deleted *S. mutans*

1) The sample produced from (1) above is added to a plate, left still overnight at 4° C.
2) The plate is washed three times with a wash buffer (e.g., above Wash Buffer B), then skimmed milk (e.g., above Buffer 4) is added thereto, and left still at room temperature for 1 hour.
3) The plate is washed three times with the wash buffer, then a primary antibody (e.g., above Buffer 5) is added, and reacted at room temperature for 1 hour.
4) The plate is washed three times with the wash buffer, then a labeled secondary antibody (e.g., above Buffer 6) is added, and reacted at room temperature for 1 hour.
5) The plate is washed three times with the wash buffer, then a color-developing reagent (e.g., above Buffer 7) is added, and after appropriate time period, changes in the color of the solution are observed. When the color of the solution changes, it is determined to be PA-positive, and when the color of the solution does not change, it is determined to be PA-negative.

In Analysis 4, detection of CBP-carrying *S. mutans* is carried out by the following procedures using for example instruments and reagents in the aforementioned kit for detecting CBP-carrying *S. mutans*.

(1) The medium (e.g., above Special Medium D) is washed three times with a wash buffer (e.g., above Wash Buffer A), then albumin-containing buffer (e.g., above Buffer 8) is added, and left still at 37° C. for 1 hour.
(2) After washing three times with a wash buffer containing a surfactant (e.g., above Wash Buffer C), bacterial solution cultured by the method of Analysis 1 above is added, and incubated at 37° C. for 2 hours.
(3) After washing three times with the wash buffer (e.g., above Wash Buffer A), a fixative solution (e.g., above Buffer 9) is added and left still at room temperature for 30 minutes.
(4) After washing three times with the wash buffer, a Gram-positive bacteria staining reagent (e.g., above Buffer 1) is added and left still for 1 minute.
(5) After washing three times with Wash Buffer A, a mordanting agent (e.g., above Buffer 2) is added.

When the color of the solution changes, it is determined to be CBP-positive, and when the color of the solution does not change, it is determined to be CBP-negative.

In any of the detecting methods described above, detection is possible when bacterial concentration is 1 CFU or more.

Moreover, a culture of e.g., *S. sobrinus, S. sanguinis, S. oralis, S. gordonii*, and *S. salivarius* may be used as a control to confirm in Analysis 1 that any bacterium other than *S. mutans* and *S. sobrinus* does not grow; in Analysis 3 that any bacterium other than PA-carrying *S. mutans* does not show a positive reaction; and in Analysis 4 that any bacterium other than CBP-carrying *S. mutans* does not show a positive reaction, respectively.

A skilled person in the art may appropriately modify the method of the present invention according to its object. For example, for detecting PA-deleted *S. mutans*, a substrate to which a specific antibody against PA or CBP is attached may be contacted with a bacterial solution, washed to remove the bacteria that do not attach to the substrate, then only the bacteria that attached to the substrate can be detected by the Gram-positive bacteria staining reagent. Alternatively, primers or probes for a PA or CBP-coding nucleic acid may be used to detect whether the cultured bacterium has the gene of PA or CBP.

In preferred embodiments of the present invention, *S. mutans* MT8148 strain may be used as a positive control for detection of a PA-deleted oral bacterium, and/or as a negative control for detection of a CBP-carrying oral bacterium. As a positive control for detection of a PA-deleted oral bacterium, depending on the detection method, an isolated PA protein, a nucleic acid or a vector comprising a DNA encoding PA or its fragment, a cell transformed with said vector may also be used. As a negative control for detection of a CBP-carrying oral bacterium, CND strain, which is a TW295 strain in which CBP-encoding gene has been knocked out, and a Gram-positive bacterium that does not express CBP may also be used.

The term "subject" in the present invention means any living organism, preferably an animal, more preferably a mammal, still more preferably a human individual.

Hereinafter, the present invention is explained in detail using working examples; however, the present invention should not be limited to these examples.

EXAMPLES

Example 1

Examination of Virulence of Streptococcus mutans in Mouse Model of Dextran Sulfate Sodium (DSS)-Induced Enteritis Effects of each strain of *S. mutans* on inflammatory bowel disease and their causative factors were examined using a mouse model of dextran sulfate sodium (DSS)-induced enteritis.

Materials and Methods
1. *S. mutans* Bacterial Strain
ATW295 strain (serotype k) isolated from the blood of a patient with bacteremia after tooth extraction was used (provided from Tokyo Women's Medical University). As a standard strain, a MT8148 strain (serotype c) isolated from the oral cavity of a Japanese infant was used as a tested bacterium.

2. Mouse Model of Dextran Sulfate Sodium (DSS)-Induced Enteritis
In order to induce a mild inflammation in a BALB/c mouse (8-week old male, body weight from 20 to 30 g), the concentration of DDS used was set to be 2.5% (DDS was dissolved in tap water before administration). Under this condition, usually inflammatory symptoms develop from day 4 after DSS administration, and approximately 40% of the mice are dead on day 15. Disease activity index (DAI) which includes this mortality rate on day 15 time-course change in body weight, and bleeding in the digestive tract (bloody stool) was employed as a major index of the analysis.

To mimic transient bacteremia by oral bacteria, $1\times10^7$ colony forming unit (CFU) of the tested bacteria were bolus-administered via the cervical vein.

For detection of the bacteria, PCR method using the following *S. mutans*-specific primer (Hoshino et al. (2004) Dian Microbiol Infect Dis 48: 195-199, 2004) was carried out.

*S. mutans*-Specific Primer
Forward: 5'-GGC ACC ACA ACA TTG GGA AGC TCA GTT-3' (SEQ ID NO: 11)
Reverse: 5'-GGA ATG GCC GCT AAG TCA ACA GGA T-3' (SEQ ID NO: 12)

3. Results
When oral bacteria were administered simultaneously with the start of DSS administration, no significant changes were observed in both the TW295 administration group and MT8148 administration group compared to the control group without administration of oral bacteria.

Figure 4:
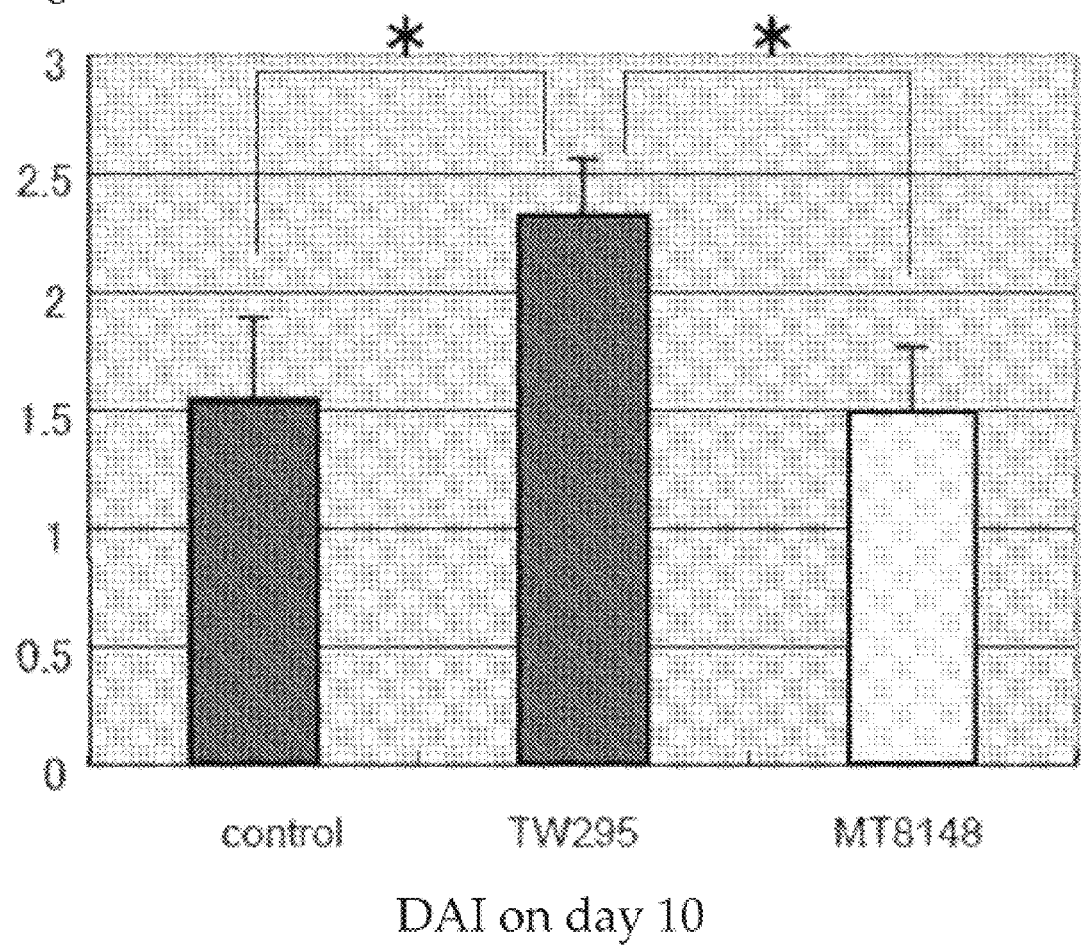
FIG. 4 is a graph showing DAI scores of the control group, TW295 administration group, and MT8148 administration group on day 10 following administration.

When oral bacteria were administered at 4 days after the start of DSS administration, at which inflammation begins to occur, the DAI score showed a high value (namely, aggravation of enteritis) in the TW295 administration group on day 7, and the value significantly increased on day 10. In contrast, no significant increase in the value was observed in the MT8148 group compared to the control (FIG. 4).

Regarding the change in body weight, a decreasing tendency was observed in the TW295 administration group, compared to other groups. A significant decrease in the body weight was observed in the TW295 group compared to the control on days 11-15 (top photos in FIG. 5), and observation of the large intestine by dissection revealed aggravation of enteritis (bottom photos in FIG. 5).

Figure 6:
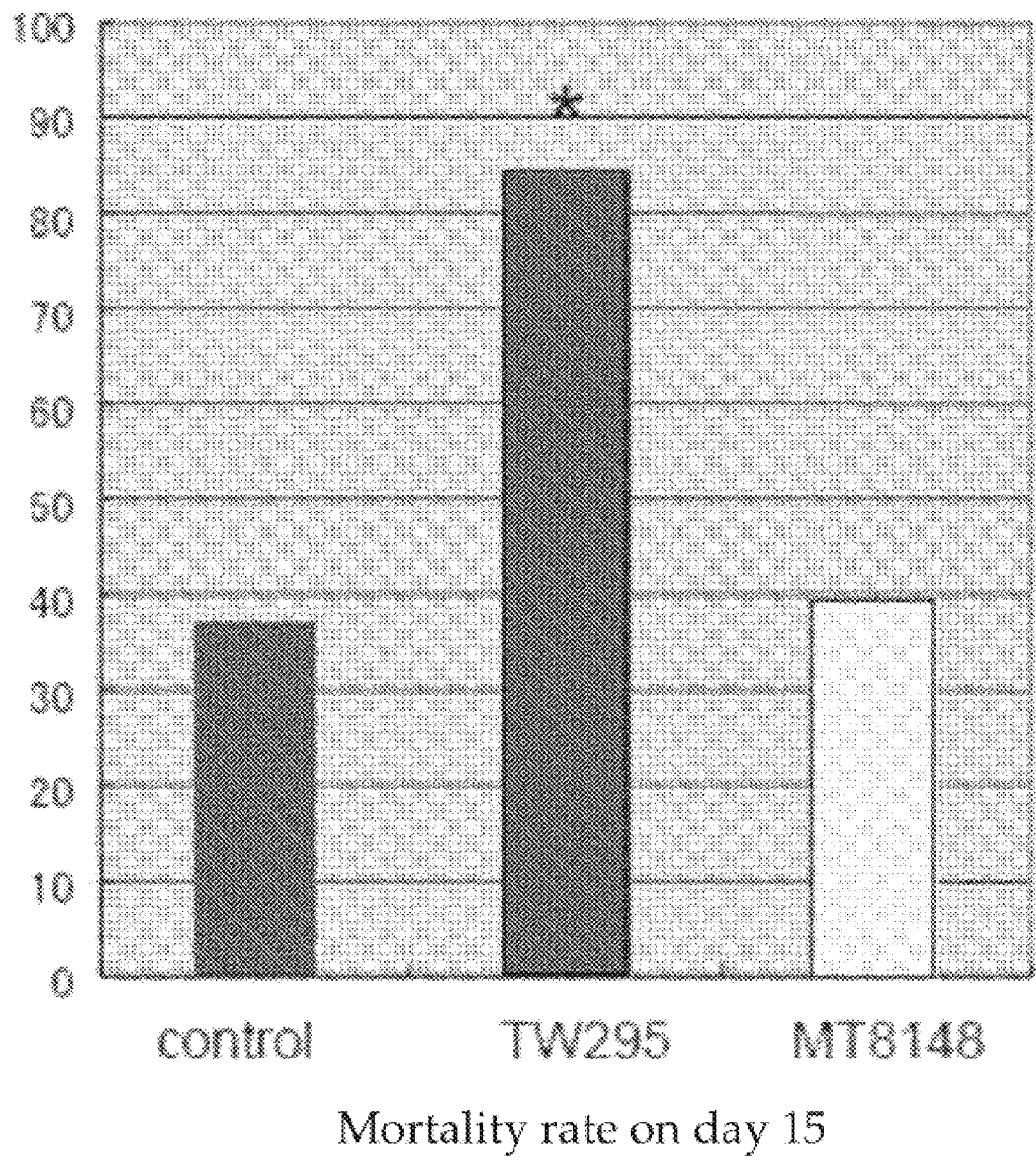
FIG. 6 is a graph showing mortality rate of the control group, TW295 administration group, and MT8148 administration group on day 15 following administration.

Mortality rate on day 15 also showed a remarkably high value in the TW295 group compared to the control; however, no difference was observed between the MT8148 strain as a standard strain and the control (FIG. 6).

By way of precaution, effects of oral administration of TW295 at $1\times10^8$ CFU on the disease state were also examined; as a result, no worsening of the disease state was observed in the oral administration group. These results suggested a possibility that highly virulent TW295 invades into the blood via the transient bacteremia and worsens enteritis not from the mucosal side of the intestinal tract, but from the inner side of the blood vessel, thereby increasing mortality rate.

Example 2

Examination of Amount of Administration of Streptococcus mutans and Mortality Rate For the DSS-induced enteritis mouse model used in Example 1, the amount of highly virulent TW295 strain was changed between $1\times10^3$ CFU and $1\times10^7$ CFU, and their effect on mortality rate was examined. Here, the tested bacteria and their administration method, etc. were in accordance with Example 1.

Figure 7:
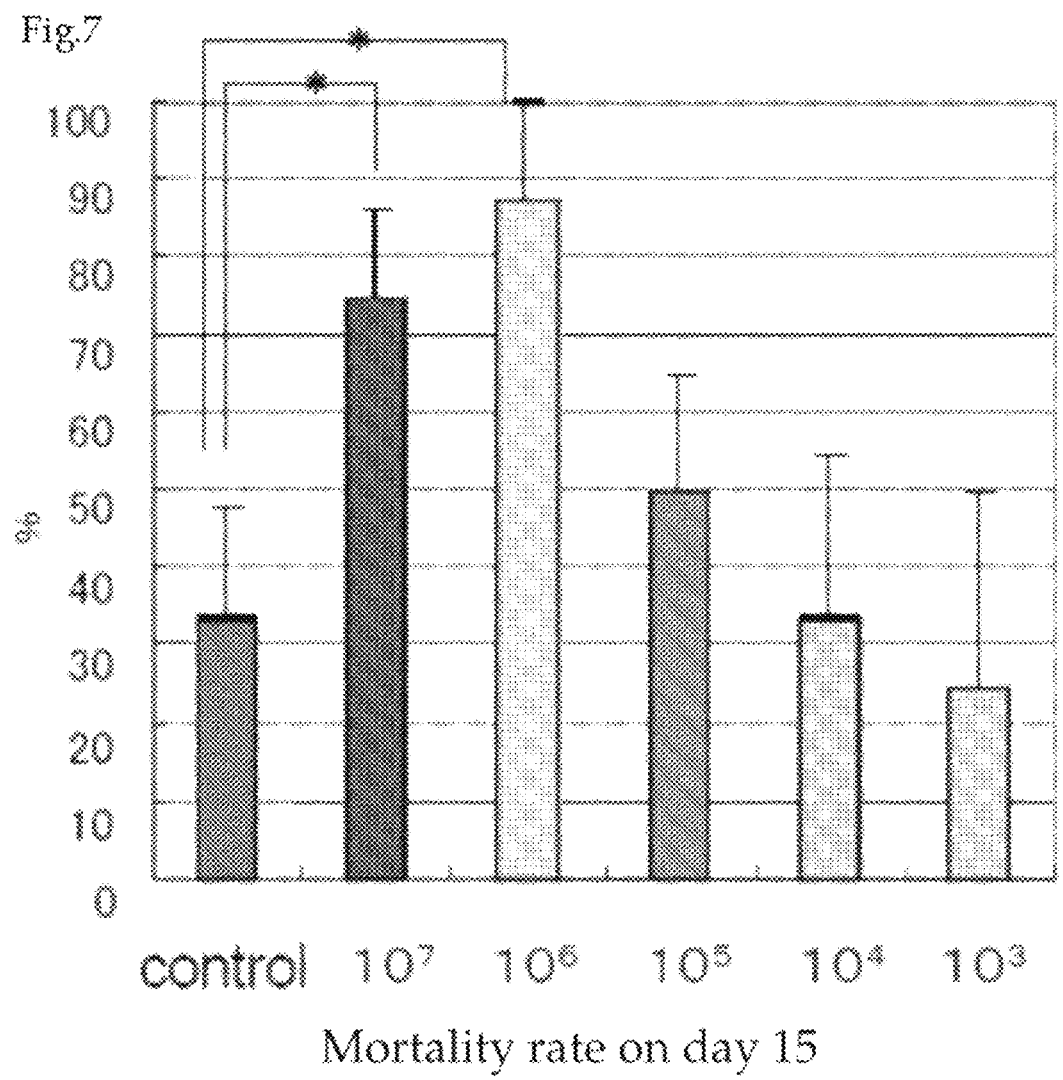
FIG. 7 is a graph showing mortality rate on day 15 following administration when the amount of TW295 administration was changed.

As a result, no difference in the mortality rate between the administration group and the control up to the amount of administration of $1\times10^4$ CFU, but an increase in the mortality rate was observed from $1\times10^5$ CFU, and a statistically significant increase in the mortality rate was observed from $1\times10^6$ CFU (FIG. 7). From this, it is suggested that the highly virulent TW295 strain aggravates enteritis when $1\times10^5$ CFU or more of the bacteria invade in the blood, and as a result the strain exhibits a risk of increasing the mortality rate.

Example 3

Examination of Mechanism of Aggravation of Enteritis by Streptococcus mutans TW 295

The reason why the standard strain MY8148 does not aggravate enteritis while TW295 aggravates enteritis and increases mortality was examined with focusing on collagen binding protein possessed by TW295.

Production of CBP Gene Deletion Strain (CND Strain):
A CND strain, which is a TW295 strain from which a collagen binding protein (CBP)-coding gene is knocked out, was produced. Namely, using the following primer that was designed based on the cnm gene total sequence (SEQ ID NO: 4; DDBJ accession No. AB469913) that encodes CBP of TW295 strain, cnm gene fragments of the TW295 strain were amplified.

Cnm Amplification Primer:

```
                                           (SEQ ID NO: 13)
   cnm1F 5'-GAC AAA GAA ATG AAA GAT GT-3'

(SEQ ID NO: 14)
   cnm1R 5'-GCA AAG ACT CTT GTC CCT GC-3'
```

The amplified fragment was integrated into pGEM-T Easy vector (Promega, Madison, Wis., USA) to produce a plasmid pTN11. pTN11 was treated by a restriction enzyme Bsml, and around the center of the open reading frame of cnm was digested to produce a plasmid pTN12 in which erythromycin-resistant gene fragment taken out from the plasmid pKN100 was integrated. After pTN12 was made into a single strand using restriction enzyme Pstl, a homologous recombination of the TW295 strain was performed by a chemical method using equine serum. Screening of the strain having erythromycin-resistant gene at the center of the cnm gene (CND strain) was carried out using a *S. mutans* selection medium comprising erythromycin. The produced strain was confirmed by Southern hybridization and measurement of collagen binding ability.

Aggravation of enteritis was examined using the produced *S. mutans* CND strain. Here, other tested bacteria and their administration method, etc. were in accordance with Example 1.

Figure 8:
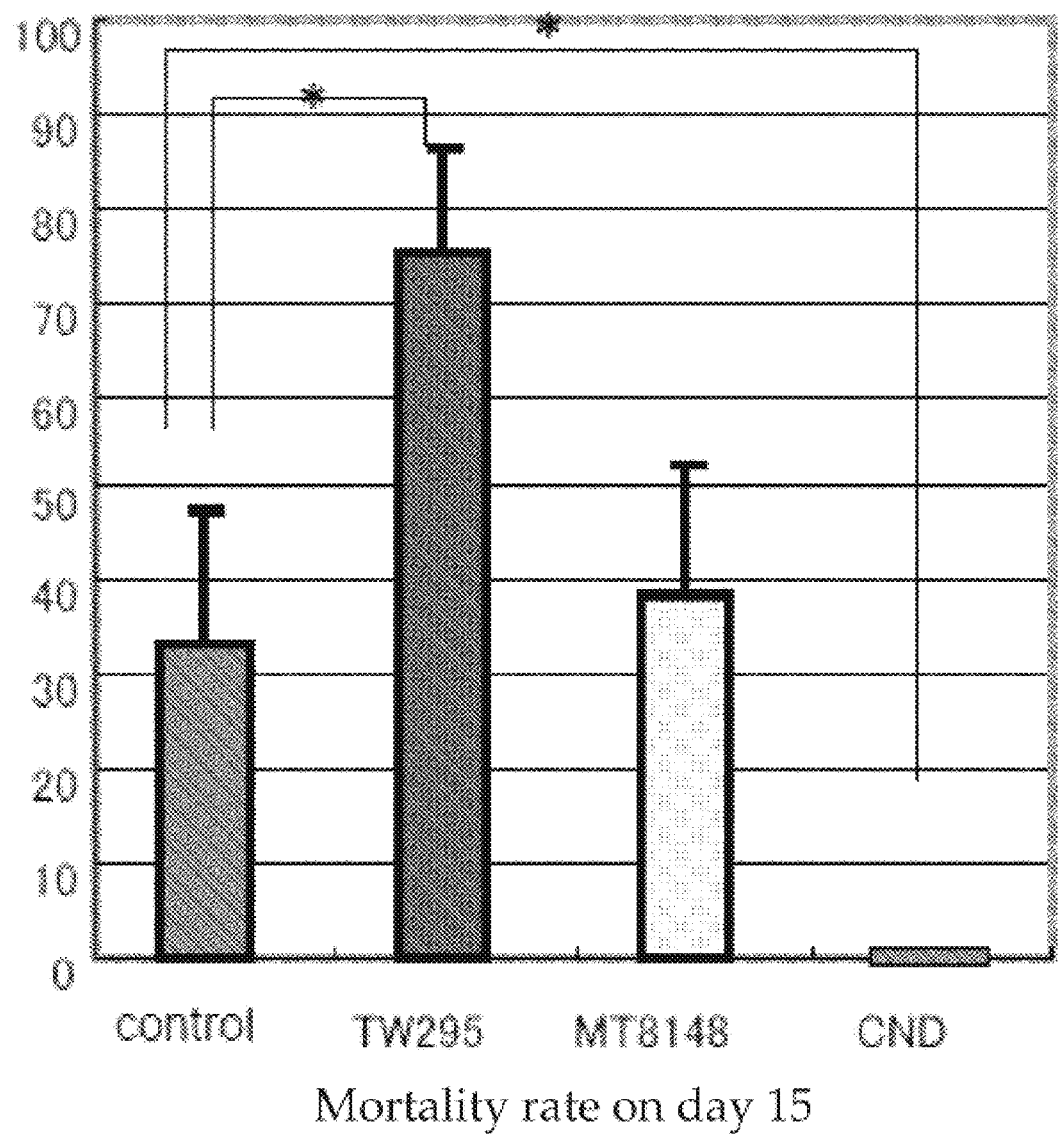
FIG. 8 is a graph showing mortality rate of the control group, TW295 administration group, MT8148 administration group and CND administration group on day 15 following administration.

As a result, DAI score of the CND strain on day 10 was significantly lower than that of TW295, and was almost equal to that of the control. Furthermore, the mortality rate of the CND strain on day 15 was remarkably low, which was significantly lower than not only the parent TW295 strain, but also the MT8148 and the control (FIG. 8). These results indicate that the collagen binding protein (CBP) plays an important role in the mechanisms of aggravation of enteritis and of increase in mortality rate of the highly virulent TW295.

Example 4

Examination of Presence/Absence of Localization of *Streptococcus mutans* in Various Organs In order to investigate bacteremia caused by a highly virulent TW295 strain, namely, to investigate the mechanism through which a TW295 strain that invades into the blood aggravates enteritis and, in the first place, whether the administered strain actually reaches the intestinal tract, each organ was extracted immediately after intravenous administration of the bacteria, and presence of the bacteria was confirmed by PCR method. Here, tested bacteria and their administration method, etc. were in accordance with Example 1.

Figure 9:
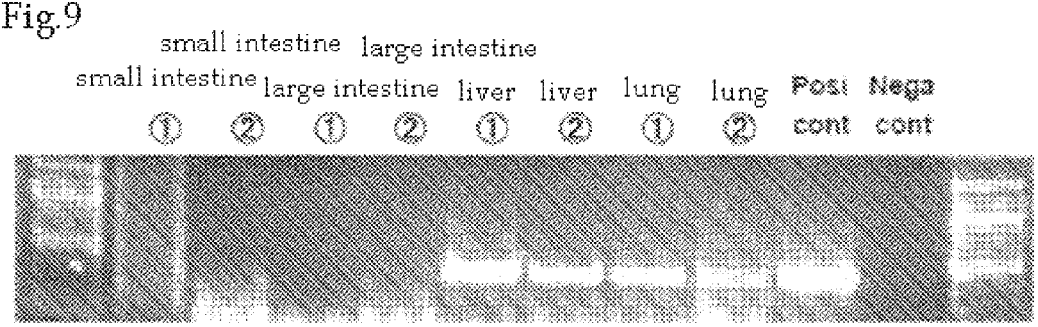
FIG. 9 is an electrophoretogram of PCR products showing presence/absence of highly virulent *Streptococcus mutans* in the small intestine, large intestine, liver and lung.

As a result, no band was observed in the intestinal tract such as the large intestine and small intestine, and presence of the bacteria was not confirmed (FIG. 9). On the other hand, a band presumed to be derived from the bacteria was observed in the liver and lung (FIG. 9). These results suggest a possibility that the administered bacteria accumulate in these organs.

Figure 10:
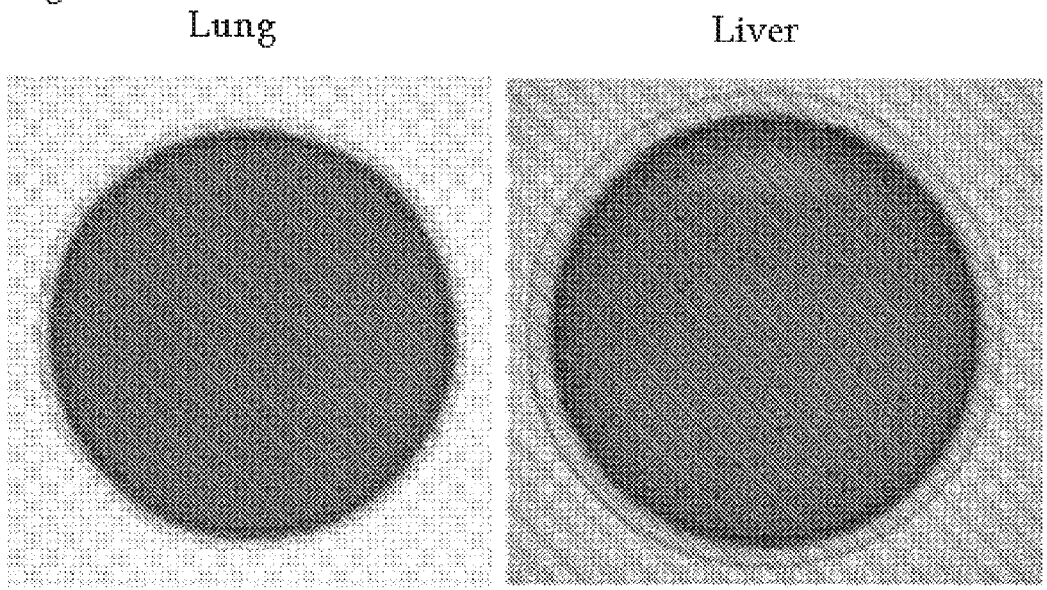
FIG. 10 shows photographs of typical examples of the results of seeding homogenize of lung and liver onto MSB plate.

For the purpose of further confirmation, a homogenize of each organ 3 hours after administration of the bacteria was plated on a MSB plate, a selection medium of *S. mutans*, and proliferation of the bacteria was determined. As a result, almost no bacterial colony was observed in the lung, and many bacterial colonies were observed only in the liver (FIG. 10). These results suggest a possibility that the TW295 after administration accumulates in the liver, thereby aggravating enteritis. Each colony was confirmed to be the administered TW295 by means of PCR using a specific primer. Interestingly, in the liver of a mouse in which enteritis was induced by administration of DSS, with an estimated number of 1.80-2.00 million of TW295 accumulated at the time point 3 hours after the administration. This number is actually 20% of the total number of bacteria administered. In contrast, in a mouse without administration of DSS, namely, without induction of enteritis, only an estimated number of 0.02 million of TW295 accumulated. These results suggest a possibility that highly virulent TW295 specifically accumulate in the liver with induced enteritis.

Example 5

Observation of Localization in Tissue of *Streptococcus mutans* TW295-GFP Strain (TW295 with Integration of GFP Genes)

A TW295 strain genetically modified to express a green fluorescent protein (GFP), a fluorescent label, was produced in accordance with a routine method (TW295-GFP strain).

The produced TW295-GFP strain was administered to a mouse treated with DSS, and localization of the bacteria in the tissue was observed. As a result, it was clarified that the bacteria after administration were not taken up by the cells of the immune system such as vascular endothelium and Kupffer cells, instead they were taken up by the hepatocytes (FIG. 11). This is a new finding because to date, there has been no report describing that a large amount of bacteria was taken up by hepatocytes.

Example 6

Analysis Using DNA Microarray

Since accumulation of highly virulent TW295 in hepatocytes of the liver is considered to be a mechanism for aggravating enteritis, an exhaustive analysis of changed genes was carried out using the liver tissue after bacterial administration. The analysis was performed using DNA microarray.

Figure 12:
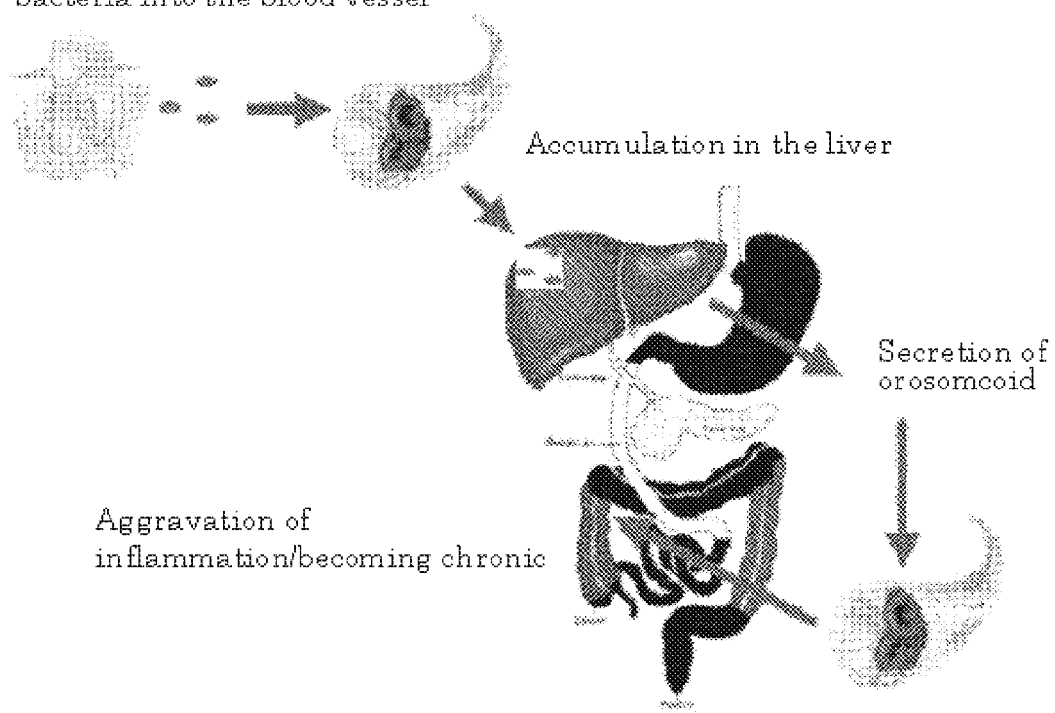
FIG. 12 is a conceptual diagram showing mechanism of aggravating inflammatory digestive tract disorders by highly virulent *Streptococcus mutans*.

As a result, it was recognized that expression of a number of interesting genes increased. Some of such genes are those coding for inflammation-related proteins that are generated by the hepatocytes, and that are known to be secreted in the blood. As a typical example of such inflammation-related proteins includes orosomucoid; and the following mechanism of aggravation of enteritis is suggested: (1) invasion of highly virulent bacteria into the blood vessel, (2) accumulation of said highly virulent bacteria in the liver, (3) production of orosomucoid by the hepatocytes due to stimulation by the highly virulent bacteria, and (4) aggravation of inflammation and the inflammation becoming chronic by the orosomucoid (FIG. 12).

Reference Example

Production of PA Gene-Deleted Strain (PD Strain)

In accordance with a method by Nakno et al., Microbes, Infect. 2006 8 (1): 114-21, a primer on the basis of pac gene total sequence (SEQ ID NO: 2, DDBJ accession number X14490) that encodes PA of MT8148 strain was used to produce a PD strain, by means of a method similar to that for the above CND strain.

Primer for pac Amplification
pac-F 5'-GCG CGC ATG CTT TAT TCA GAT TTG GAG GAT-3' (SEQ ID NO: 15)

pac-R 5'-GCG AAA GCG CAT GCT GTG ATT TAT CGC TTC-3' (SEQ ID NO: 16)

Detection Example 1

Detection of *Streptococcus mutans* that Aggravates Inflammatory Digestive Tract Disorders Materials and Methods Tested bacteria: Following bacteria were used in the establishment of the detection system.

| | |
|---|---|
| *S. mutans* | MT8148 strain (PA+/CBP−)/TW295 strain (PA−/CBP+) |
| *S. sobrinus* | B13 strain/6715 strain |
| *S. sanguinisA* | TCC10556 strain |
| *S. oralis* | ATCC10557 strain |
| *S. gordonii* | ATCC10558 strain |
| *S. salivarius* | HHT strain |

Analysis 1. Method for Culturing *S. MUTANS* (Mutans Streptococci) (Operation Time: about 5 Minutes, Waiting Time (Such as During Culturing of a Bacterium): 2 Days)

Culturing of *S. mutans* employs the following things:
spitz for collecting saliva (not particularly limited as long as it is sterilized and suitable for collecting and seeding)
a special dropper capable of collecting saliva of 10 µl
Special Medium A (agar medium) (24-well plate (it is not particularly limited as long as it is a plate of about 24-well, e.g., 24 well with Lid MICROPLATE (IWAKI)) coated with MSB agar medium e.g., Mitis-salivarius agar medium (Difco Laboratories) supplemented with bacitracin (100 unit/ml; SIGMA-ALDRICH) and 15% sucrose (Wako Pure Chemical Industries, Ltd.). It is preferred to be provided with Anaero Pack®.)
a sterilized toothpick and the like for picking up bacterial colonies
Special Medium B (liquid medium) (sterilized Brain Heart Infusion (BHI) liquid medium (Difco Laboratories) contained in a disposal test tube).

Culturing of *S. mutans* is carried out as follows.

The saliva of the subject is collected in a small amount using a spitz for collecting saliva. 10 µl of the saliva is taken from the spitz using a special dropper, plated onto Special Medium A, then cultured at 37° C. for 48 hours, preferably in an anaerobic condition. After culturing, presence of bacterial colonies is confirmed with the naked eye, and the colonies (rough colonies are desirable) are picked up and added into Special Medium B, cultured at 37° C. for 18 hours, and used in the following Analyses 2, 3 and 4. Cultures of *S. sobrinus, S. sanguinis, S. oralis, S. gordonii*, and *S. salivarius* are used as controls to confirm that no bacterium other than *S. mutans* and *S. sobrinus* grows in Analysis 1.

Analysis 2. Method for Detecting *S. mutans* (Mutans Streptococci) (Operation Time: about 15 Minutes, Waiting Time (Such as During Culturing of Bacteria): about 3 Hours)

Although the method of culturing mutans streptococci of the above Analysis 1 is provided with conditions in which the mutans streptococci group (*S. mutans/S. sobrinus*) can preferably grow, a bacterium having bacitracin-resistance other than mutans streptococci may grow. Therefore, confirmation is done in this step.

Detection employs the following things:
a special dropper capable of collecting bacterial solution of 10 µl
Special Medium C (96-well plate (e.g., MULTI WELL PLATE for ELISA (SUMIRON)) containing 100 µl of BHI solution containing 1% sucrose (Wako Pure Chemical Industries, Ltd.))
Wash Buffer A (PBS solution)
Buffer 1 (a solution in which 0.5% crystal violet (Wako Pure Chemical Industries, Ltd.) is added to sterile distilled water)
Buffer 2 (7% acetate (Wako Pure Chemical Industries, Ltd.) solution)

Detection is carried out as follows:

10 µl of the bacterial solution cultured according to the method of Analysis 1 is added to Special Medium C, incubated at 37° C. for 3 hours. The Special Medium C is washed three times with Wash Buffer A, then left still for approximately 15 minutes after the last Wash Buffer A is added. This Wash Buffer A is removed, and the Special Medium C is washed once again with Wash Buffer A, then 100 µl of Buffer 1 is added to the Special Medium C and left still for 1 minute. This is washed three times with Wash Buffer A, and 200 µl of Buffer 2 is added thereto.

It is determined to be *S. mutans*-positive when the color of the medium changes, and *S. mutans*-negative when the color of the medium does not change.

Analysis 3. Method for Detecting PA-Deleted *S. mutans* (Operation Time: about 30 Minutes, Waiting Time (Such as During Culturing of Bacteria): about 11 Hours and 30 Minutes)

Detection of PA-deleted *S. mutans* employs the following things:
Special Plate (96-well plate; MICROTEST U-Bottom (BECTON DICKINSON))
Wash Buffer B (a PBST solution in which 0.05% of Triton X-100 (Wako Pure Chemical Industries, Ltd.) is added to Wash Buffer A used in Analysis 2)
Buffer 3 (a mixture of Tris buffered saline, pH6.8, 100 mM dithiothreitol (Wako Pure Chemical Industries, Ltd.) and 20% glycerin (Wako Pure Chemical Industries, Ltd.))
Buffer 4 (a PBST solution supplemented with 5% skimmed milk (BECTON DICKINSON))
Buffer 5 (a PBST solution supplemented with 0.1% rabbit anti-PA antiserum (stored in our laboratory))
Buffer 6 (a PBST solution supplemented with 0.1% porcine anti-rabbit immunoglobulin antibody (Dakopatts))
Buffer 7 (a solution in which AP buffer (100 mM 2-amino-2-hydroxymethyl-1,3-propanediol, 5 mM magnesium chloride, 100 mM sodium chloride) is supplemented with NBT solution (Wako Pure Chemical Industries, Ltd.) at 0.6% final concentration and BCIP solution (Wako Pure Chemical Industries, Ltd.) at 0.33% final concentration.)

Detection of PA-deleted *S. mutans* is carried out as follows:

(1) Sample Preparation

To 100 it of the bacterial solution cultured according to the method of Analysis 1 above, Buffer 3 is added, and immersed in boiling water for 10 minutes, and frozen if it is to be stored.

(2) Detection of PA-Deleted *S. mutans*

1) 100 it of the sample prepared as above (1) is added to the Special Plate, left still overnight at 4° C.

2) The Special Plate was washed three times in Wash Buffer B, then 100 µl of Buffer 4 is added thereto, left still at room temperature for 1 hour.

3) The Special Plate was washed three times in Wash Buffer B, then 100 µl of Buffer 5 is added thereto, reacted at room temperature for 1 hour.

4) The Special Plate was washed three times in Wash Buffer B, then 100 µl of Buffer 6 is added thereto, reacted at room temperature for 1 hour.
5) The Special Plate was washed three times in Wash Buffer B, then 100 µl of Buffer 7 is added thereto, and after 15 minutes changes in the color of the solution are observed. It is determined to be PA-positive when the color of the solution changes, PA-negative when the color of the solution does not change. Cultures of S. sobrinus, S. sanguinis, S. oralis, S. gordonii, and S. salivarius are used as controls to confirm that no bacterium other than PA-carrying S. mutans shows a positive reaction in Analysis 3.

Analysis 4. Detection Method of CBP-Carrying S. mutans (Operation Time: about 30 Minutes, Waiting Time (Such as During Culturing of a Bacterium): about 3 Hours and 30 Minutes)

Detection of CBP-carrying S. mutans employs the followings:

Special Medium D (the Special Plate used in Analysis 3, to which a mixed solution of sterile distilled water supplemented with 0.6% acetate and Type I collagen (Sigma) in 9:1 ration was added.)
Wash Buffer A (the same buffer as that used in above Analysis 2 (detection method of S. mutans))
Buffer 8 (Wash Buffer A supplemented with 5% bovine albumin (Sigma))
Wash Buffer C (Wash Buffer A which is a PBST solution supplemented with 0.01% Tween 20 (Wako Pure Chemical Industries, Ltd.))
Buffer 9 (sterile distilled water supplemented with 25% formaldehyde (Wako Pure Chemical Industries, Ltd.))
Buffer 1 (the same buffer as that used in above Analysis 2)
Buffer 2 (the same buffer as that used in above Analysis 2)

Detection of CBP-carrying S. mutans is carried out as follows:
(1) Special Medium D is washed three times with Wash Buffer A, then 200 µl of Buffer 8 is added thereto, and left still at 37° C. for 1 hour.
(2) Washed three times with Wash Buffer C, then 200 µl of the bacterial solution cultured according to the method of 1 described above is added thereto, and incubated at 37° C. for 2 hours.
(3) Washed three times with Wash Buffer A, then 200 µl of Buffer 9 is added thereto, and left still at room temperature for 30 minutes.
(4) Washed three times with Wash Buffer A, then 200 µl of Buffer 1 is added to the 96-well plate, and left still for 1 minute.
(5) Washed three times with Wash Buffer A, then 200 µl of Buffer 2 is added thereto.

It is determined to be CBP-positive when the color of the solution changes, CBP-negative when the color of the solution does not change. Cultures of S. sobrinus, S. sanguinis, S. oralis, S. gordonii, and S. salivarius are used as controls to confirm that no bacterium other than CBP-carrying S. mutans shows a positive reaction in Analysis 4.

Analysis Example 1

Figure 13:
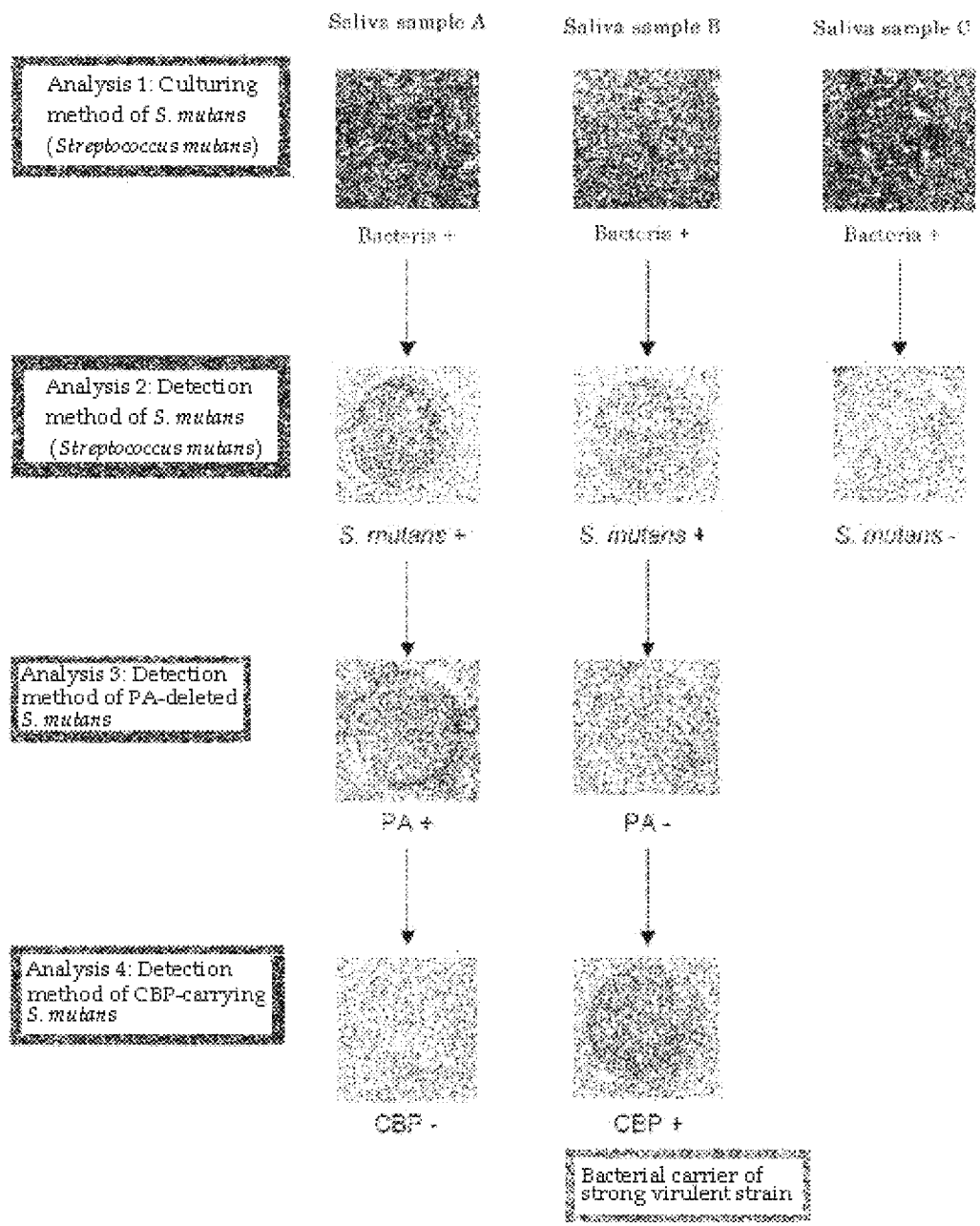
FIG. 13 shows an example of analytical results determining presence of PA-deleted *S. mutans* and CBP-carrying *S. mutans*.

FIG. 13 is an example of the result of an analysis on whether the S. mutans in saliva samples (A, B and C) collected from 3 subjects are PA and/or CBP-carrying strains. As results of culturing saliva samples in Special Medium A (bacitracin-selection agar medium) in steps in Analysis 1, colony formation was confirmed in all of A, B and C. Formed colonies are picked up and cultured in Special Medium B at 37° C. for 18 hours. In addition, cultures of S. sobrinus, S. sanguinis, S. oralis, S. gordonii, and S. salivarius were cultured similarly as controls, and it was confirmed that no bacterium other than S. mutans and S. sobrinus grew in Analysis 1.

Subsequently, in steps in Analysis 2, the bacterial solution cultured in Analysis 1 was added to Special Medium C, incubated at 37° C. for 3 hours, washed with Wash Buffer A, then stained with Buffer 1 containing crystal violet. Since the color of the buffer changed to blue-violet in the medium in which samples A and B has been cultured, the presence of S. mutans was determined. As the buffer remained transparent in the medium in which sample C has been cultured, absence of S. mutans was determined.

In steps in Analysis 3, Buffer 3 was added to each of the bacterial solutions of the samples A and B cultured in Analysis 1 and boiled for 10 minutes, and stored frozen. This was added to Special Plate (96-well plate: MICROTEST U-Bottom (BECTON DICKINSON)), left still overnight at 4° C. After washing with Wash Buffer B, Buffer 4 was added and blocked at room temperature for 1 hour, then Buffer 5 containing rabbit anti-PA antiserum was added and reacted at room temperature for 1 hour. After washing with Wash Buffer B, Buffer 6 containing porcine anti-rabbit immunoglobulin antibody was added and reacted at room temperature for 1 hour. After washing with Wash Buffer B, Buffer 7 which contained an alkaline phosphatase reaction-detecting reagent was added, and after 15 minutes changes in the color of the solution were observed. Since the color of the solution changed to pink in the plate of the sample A, presence of PA-carrying S. mutans was determined. As the color of the solution remained transparent for the sample B, absence of PA-carrying S. mutans was determined. Similar analysis was performed using cultures of S. sobrinus, S. sanguinis, S. oralis, S. gordonii, and S. salivarius as controls, confirming that no bacterium other than the PA-carrying S. mutans showed a positive reaction.

In steps in Analysis 4, Buffer 8 containing 5% bovine albumin was added to the Special Medium D coated with Type I collagen (Sigma), and left still at 37° C. for 1 hour. After washing with Wash Buffer C, bacterial solution cultured in Analysis 1 was added and incubated at 37° C. for 2 hours. After washing with Wash Buffer A, Buffer 9 containing 25% formaldehyde was added, left still at room temperature for 30 minutes. After washing with Wash Buffer A, Buffer 1 was added and left still for 1 minute. After washing with Wash Buffer A, Buffer B was added and changes in the color of the solution were observed. Since the color of the solution remained transparent in the plate containing the sample A, absence of CBP-carrying S. mutans was determined. As the color of the solution changed to blue-violet in the plate containing the sample B, presence of CBP-carrying S. mutans was determined. Similar analysis was performed using cultures of S. sobrinus, S. sanguinis, S. oralis, S. gordonii, and S. salivarius as controls, confirming that no bacterium other than the CBP-carrying S. mutans showed a positive reaction.

Example 7

Optimal Conditions for Culturing S. mutans

In order to obtain a determination with higher accuracy in Analyses 2 to 4 above, it is considered to be important to culture the largest possible number of S. mutans in Analysis 1 and to minimize the contamination of bacteria other than S. mutans. As conditions for culturing, (1) culturing in an aerobic condition/anaerobic condition, (2) antibiotics (bacitracin) concentration, and (3) nutrient (sucrose) concentration were investigated. FIG. 14 is a graph showing the percentage of S.

*mutans* to total bacteria isolated when bacitracin was added to the MSB medium at (a) 1 eq. or (b) 5 eq. (assuming the amount of bacitracin in a conventional MSB medium is 1 eq.) and sucrose was added to the MSB medium at 1 to 4 eq. (assuming the amount of sucrose in a conventional MSB medium is 1 eq.). It was shown that *S. mutans* could be isolated at the highest concentration in an anaerobic condition, when 1 eq. of bacitracin and 1 eq. of sucrose were used. Accordingly, it was shown that in order to obtain a determination with higher accuracy, it is necessary to culture in a sealable container in an anaerobic condition (e.g., in a sealed pack to which Anaero Pack® is attached) in a medium supplemented with bacitracin and sucrose at the same concentration (approx. 100 unit/ml and 15%, respectively) contained in a conventional MSB medium.

Example 8

Storage Period of Samples

In the case when analysis is performed using a saliva sample collected some time ago, in order to detect virulent *S. mutans* under the optimal condition obtained in Example 4, we investigated allowable storage period of saliva samples.

Figure 15:
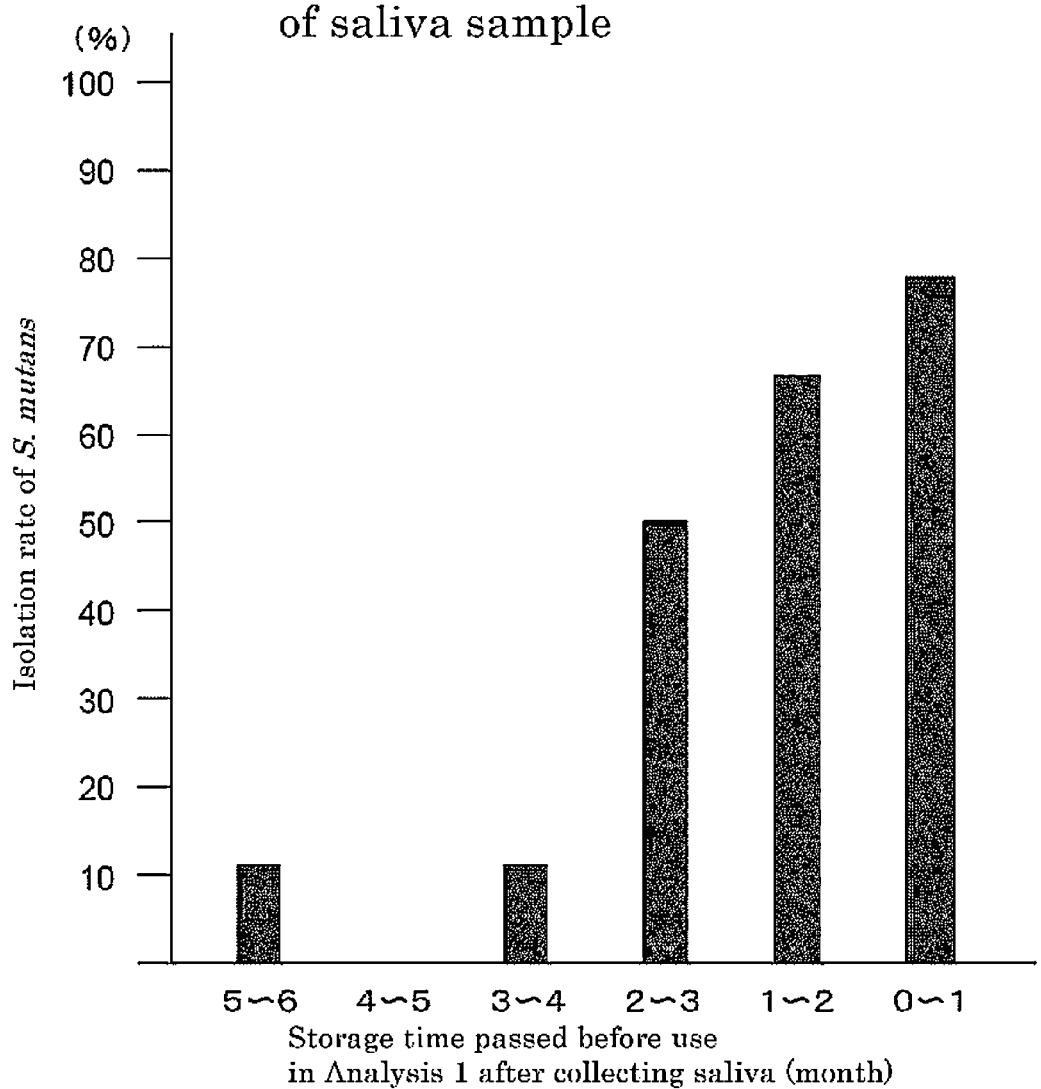
FIG. 15 is a graph showing results of investigation of storage period of usable saliva for detecting virulent *S. mutans*.

FIG. 15 is a graph showing isolation rate of *S. mutans* from saliva samples collected 0-6 months before by Analysis 1, relative to the isolation rate of *S. mutans* from a saliva sample collected and diluted with sterile saline by serial dilution on the same date and plated on a MSB agar medium as 100%. The saliva samples were frozen-stored at −20° C. after collection. The number of samples: N=8; however, the number of samples stored for 1-2 months was N=6. As a result, it is considered to be desirable that saliva samples are used preferably within 3 months, preferably within 2 months, and most preferably within 1 month after collection.

Example 9

Distribution of Genotype and Serotype of *Streptococcus mutans* in Saliva Sample With respect to *Streptococcus mutans* in saliva samples obtained from 528 healthy subjects and 24 patients with IBD, the genotype of collagen binding protein (CBP) was identified in accordance with a method by Nomura et al., 2009, Journal of Medical Microbiology, 58: 469-475, and the serotype was identified in accordance with a method by Shibata et al., 2003. Journal of Clinical Microbiology, 41, 4107-4112 and Nakano et al., 2004. Journal of Clinical Microbiology, 42, 4925-4930. Results are shown in FIG. 16 (genotype) and FIG. 17 (serotype).

Figure 16:
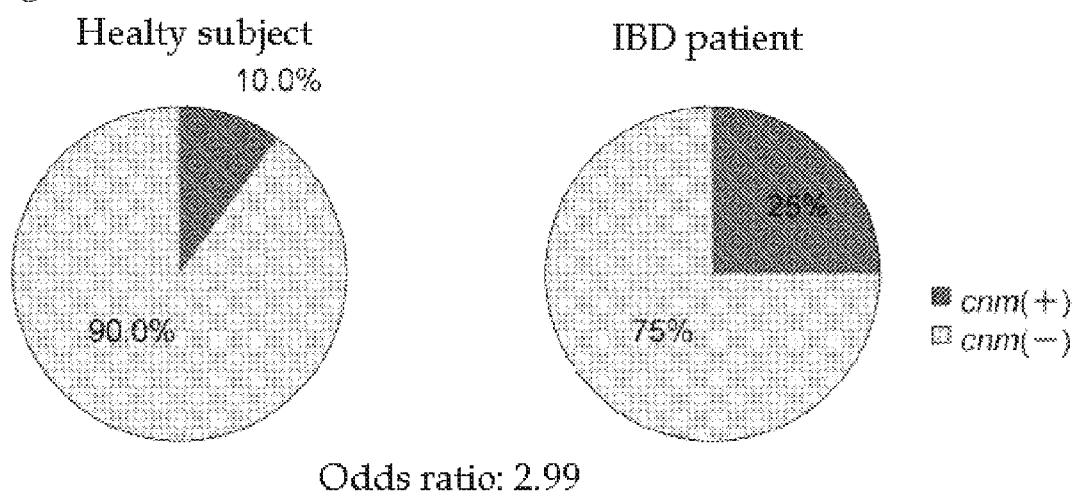
FIG. 16 is a graph showing results of distribution of genotype of *Streptococcus mutans* (cnm (+) and cnm (−)) in saliva samples.

As shown in FIG. 16, the percentage of cnm(+) in the *Streptococcus mutans* obtained from the saliva samples of healthy subjects was 10%, that in the *Streptococcus mutans* obtained from the saliva samples of IBD patients was 25%, which was significantly high (odds ratio 2.99).

Figure 17:
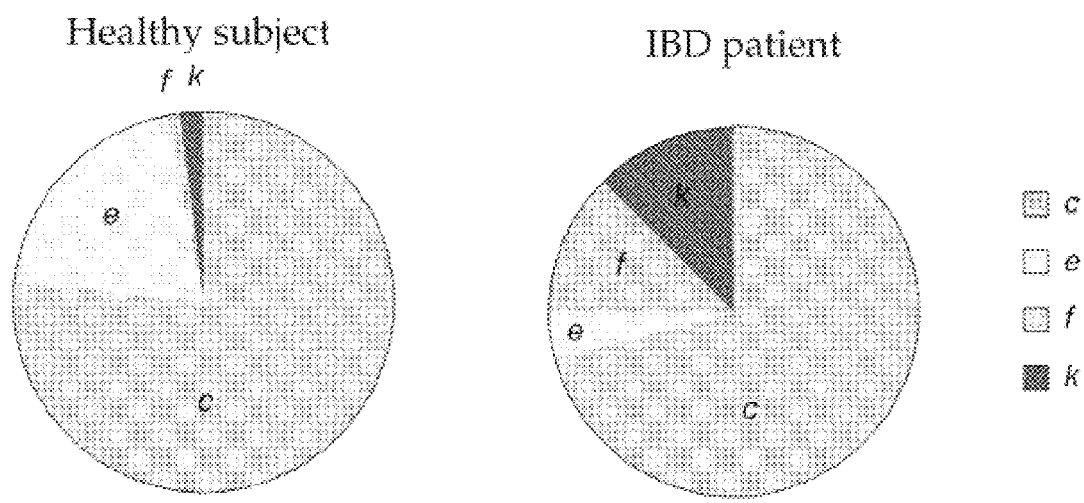
FIG. 17 is a graph showing results of distribution of serotype of *Streptococcus mutans* (c-type, e-type, f-type and k-type) in saliva samples.

In addition, as shown in FIG. 17, regarding the serotype of *Streptococcus mutans* obtained from the saliva samples of healthy subjects, the percentages of c-type (74.6%) and e-type (19.7%) are large, and those of f-type (3.4%) and k-type (2.3%) are extremely small. In contrast, regarding the serotype of *Streptococcus mutans* obtained from the saliva samples of IBD patients, the percentages of c-type (70.8%) and e-type (4.2%) are smaller than those in the healthy subjects, and those of f-type (12.5%) and k-type (12.5%) are larger than those in the healthy subjects.

In other words, in the case of healthy subjects, the percentage of (c-type+e-type) is 94.3%, and that of (f-type+k-type) is 5.7%; whereas in the case of IBD patients, the percentage of (c-type+e-type) is 75%, and that of (f-type+k-type) is 25%; thus, indicating a large ratio of specific types, i.e., (f-type+k-type) (odds ratio: 5.53).

Example 10

Serotype of *Streptococcus mutans* and Phagocytosis by Leucocytes

With respect to each of the *Streptococcus mutans* MT8148 strain (serotype c), MT8148GD strain (serotype k), and TW295 strain (serotype k), its phagocytosis rate by human leucocytes was investigated. Here, MT8148GD strain is a variant of MT8148 in which gluA gene, which encodes the enzyme that catalyzes the production of the immediate precursor of the glucose side chain donor, has been inactivated (WO 2005/063992).

Each bacterial strain was cultured in Brain Heart Infusion broth (Difco) at 37° C. for 18 hour, and the bacterial cells after culturing were washed, then the concentration of the cells was adjusted with PBS to be $1.0 \times 10^8$ CFU/ml. Human peripheral blood (500 µl) collected from a healthy volunteer was incubated with 500 µl of bacteria ($5.0 \times 10^7$ CFU/ml) at 37° C. for 10 minutes. The sample was giemsa-stained (Wako Pure Chemical Industries, Osaka, Japan), and the ratio of polymorphonuclear leucocytes (PMN) exhibiting phagocytosis was obtained using an optical microscope (magnification, ×100; Olympus Industries, Tokyo, Japan). The ratio was expressed by an average number of phagocytic PNM per 100 PMN (500 PMN were tested).

Figure 18:
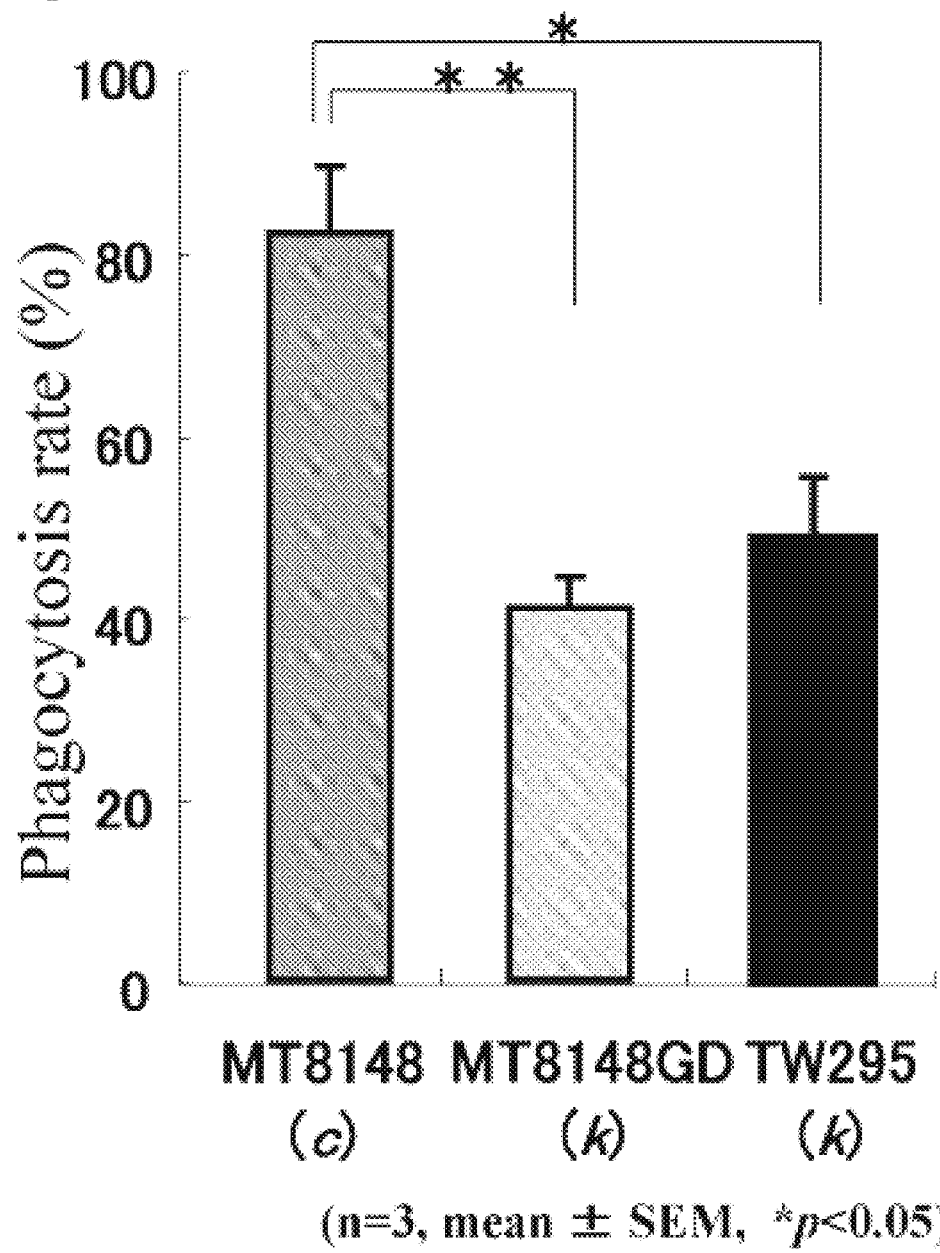
FIG. 18 is a graph showing changes in phagocytosis action by leucocytes depending on the serotype of *Streptococcus mutans*.

It was shown that the k-type MT8148GD strain and TW 295 strain, rather than the c-type MT8148 strain, are hardly phagocytized by leucocytes (FIG. 18). Consequently, k-type and f-type detected at high concentrations in saliva samples of IBD patients are hardly phagocytized by leucocytes, resulting in their long life in the blood, and leading to a tendency to induce bacteremia, etc.

Figure 19:
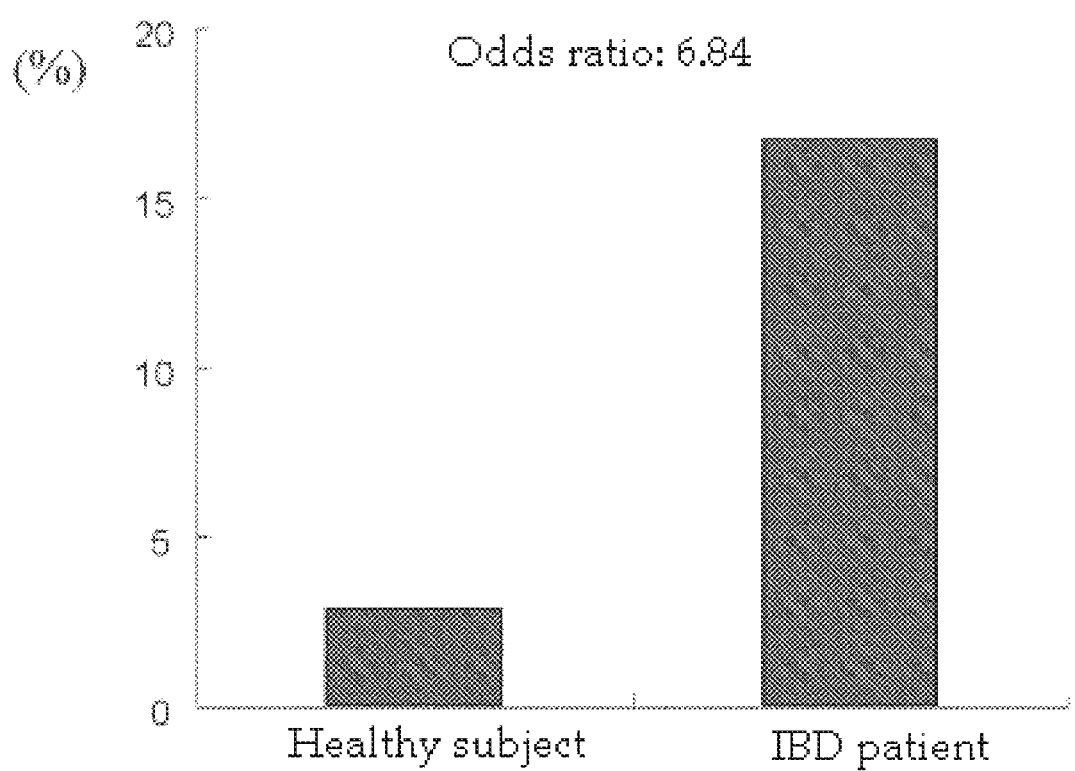
FIG. 19 is a graph showing the ratio of strains of *Streptococcus mutans* in which the genotype is cnm (+) and the serotype is f-type or k-type.

Furthermore, of the *Streptococcus mutans* in the saliva samples of IBD patients, the ratio of those with f- or k-serotype and genotype cnm(+) is remarkably higher than that in the samples of healthy subjects (FIG. 19). From this, we consider as follows: it is important to have f- or k-serotype in order to persist in the blood for a long period, and it is necessary to have CBP (cnm(+)) in order to invade into the liver as a target cell. Ultimately, it is considered that bacterial strains having both of these characteristics have higher possibility of aggravating disease conditions.

Sequences of protein, polypeptides and nucleic acids used in the present specification are described in the attached sequence list below.

[Table 1]

TABLE 1

Table of sequences

| SEQ ID No. | Species or strain | content of the sequence |
|---|---|---|
| 1 | *S. mutans* MT8148 | PA-amino acid |
| 2 | *S. mutans* MT8148 | PA-DNA |
| 3 | TW295 | CBP-amino acid |
| 4 | TW295 | CBP-DNA-ORF |
| 5 | *S. mutans* TW295 | CBD-amino acid |
| 6 | *S. mutans* TW295 | CBD-DNA |
| 7 | *S. mutans* TW871 | CBP-amino acid |

TABLE 1-continued

Table of sequences

| SEQ ID No. | Species or strain | content of the sequence |
|---|---|---|
| 8 | S. mutans TW871 | CBP-DNA-ORF |
| 9 | S. mutans TW871 | CBD-amino acid |
| 10 | S. mutans TW871 | CBD-DNA |
| 11 | Artificial | S. mutans-primer F |
| 12 | Artificial | S. mutans-primer R |
| 13 | Artificial | S. mutans-CBD-Primer F (cnm1F) |
| 14 | Artificial | S. mutans-CBP-primer R (cnm1R) |
| 15 | Artificial | S. mutans-PAC-primer F (pac-F) |
| 16 | Artificial | S. mutans-PAC-primer R (pac-R) |
| 17 | S. mutans LJ23 | PA-amino acid |
| 18 | S. mutans LJ23 | PA-DNA |
| 19 | S. mutans SA98 | PA-amino acid |
| 20 | S. mutans SA98 | PA-DNA |
| 21 | S. mutans | antigenI/II-amino acid |
| 22 | S. mutans | antigenI/II gene (spa)-DNA |
| 23 | Neisseria meningitidis | iron-binding protein-amino acid |
| 24 | Neisseria meningitidis | iron-binding protein gene (fbp) DNA |

The invention claimed is:

1. A method of detecting an oral bacterium for diagnosing whether inflammatory bowel disease is aggravated in a subject, comprising
    contacting saliva or plaque obtained from the subject with a collagen binding protein (CBP)-detecting reagent,
    performing an assay to detect CBP of oral bacteria in the saliva or plaque obtained from the subject,
    confirming the presence in the saliva or plaque obtained from the subject of an oral bacterium that aggravates inflammatory bowel disease when the CBP is detected, and
    diagnosing that inflammatory bowel disease is aggravated in the subject when the oral bacterium that aggravates inflammatory bowel disease is present in the saliva or plaque obtained from the subject.

2. The method according to claim 1, further comprising contacting the saliva or plaque obtained from the subject with a PA-detecting reagent, performing an assay to detect protein antigen (PA) of oral bacteria in the saliva or plaque obtained from the subject,
    confirming the presence in the saliva or plaque obtained from the subject of an oral bacterium that aggravates inflammatory bowel disease when PA is not detected and CBP is detected, and
    diagnosing that inflammatory bowel disease is aggravated in the subject when the oral bacterium that aggravates inflammatory bowel disease is present in the saliva or plaque obtained from the subject.

3. A method of detecting an oral bacterium for diagnosing whether a subject is at a high risk of aggravation of inflammatory bowel disease, comprising
    contacting saliva or plaque obtained from the subject with a collagen. binding protein. (CBP)-detecting reagent,
    performing an assay to detect CBP of oral bacteria in the saliva or plaque obtained from the subject,
    confirming the presence in the saliva or plaque obtained from the subject of an oral bacterium that aggravates inflammatory bowel disease when the CBI is detected, and
    diagnosing that the subject is at a high risk of aggravation of inflammatory bowel disease when the oral bacterium that aggravates inflammatory bowel disease is present in the saliva or plaque obtained from the subject.

4. The method according to claim 3, further comprising contacting the saliva or plaque obtained from the subject with a PA-detecting reagent, performing an assay to detect protein antigen (PA) of oral. bacteria in the saliva or plaque obtained from the subject,
    confirming the presence in the saliva or plaque obtained from the subject of an oral bacterium that aggravates inflammatory bowel disease when PA is not detected and CBP is detected, and
    diagnosing that the subject is at a high risk of aggravation of inflammatory bowel disease when the oral bacterium that aggravates inflammatory bowel disease is present in the saliva or plaque obtained from the subject.

5. A method of judging risk of aggravation of inflammatory bowel disease in a subject, comprising
    contacting saliva or plaque obtained from the subject with a collagen binding protein (CBP)-detecting reagent,
    performing an assay to detect CBP of oral bacteria in the saliva or plaque obtained from the subject,
    confirming the presence in the saliva or plaque obtained from the subject of an oral bacterium that aggravates inflammatory bowel disease when the CBP is detected, and
    judging that the subject is at a high risk of aggravation of inflammatory bowel disease when the oral bacterium that aggravates inflammatory bowel disease is present in the saliva or plaque obtained from the subject.

6. The method according to claim 5, further comprising contacting the saliva or plaque obtained from the subject with a PA-detecting reagent, performing an assay to detect protein antigen (PA) of oral bacteria in the saliva or plaque obtained from the subject,
    confirming the presence in the saliva or plaque obtained from the subject of an oral bacterium that aggravates inflammatory bowel disease when PA is not detected and CBP is detected, and
    judging that the subject is at a high risk of aggravation of inflammatory bowel disease when the oral bacterium that aggravates inflammatory bowel disease is present in the saliva or plaque obtained from the subject.

7. The method according to claim 1, wherein the oral bacterium is *Streptococcus mutans*.

8. The method according to claim 7. Wherein the genotype of *Streptococcus mutans* is cnm(+).

9. The method according to claim 7, wherein the serotype of *Streptococcus mutans* is f-type or k-type.

10. The method according to claim 2, wherein the PA is selected from the group consisting of:
    (1) a polypeptide comprising the amino acid sequence of SEQ ID NO: 1, 17, 19, 21 or 23;
    (2) a polypeptide comprising one or more mutations in the polypeptide of (1), but having an equal function to the polypeptide of (1);
    (3) a polypeptide comprising an amino acid sequence encoded by a nucleic acid sequence that hybridizes with the nucleic acid sequence of SEQ ID NO: 2, 18, 20, 22 or 24 or its complementary sequence or its fragment under stringent conditions, and having an equal function to the polypeptide of (1);
    (4) a polypeptide comprising an amino acid sequence having 70% or more homology with the amino acid sequence of SEQ ID NO: 1, 17, 19, 21 or 23, and having an equal function to the polypeptide of (1).

11. The method according to claim 10, wherein the PA comprises a polypeptide consisting of the amino acid sequence of SEQ ID NO: 1, 17, 19, 21 or 23.

12. The method according to claim 1, wherein the CBP is selected from the group consisting of:
    (1) a polypeptide comprising the amino acid sequence of SEQ ID NO: 5 or 9;
    (2) a polypeptide comprising one or more mutations in the polypeptide of 1), but having an equal function to the polypeptide of (1);
    (3) a polypeptide comprising an amino acid sequence encoded by a nucleic acid sequence that hybridizes with the nucleic acid sequence of SEQ ID NO: 6 or 10 or its complementary sequence or its fragment under stringent conditions, and having an equal function to the polypeptide of (1);
    (4) a polypeptide comprising an amino acid sequence having 70% or more homology with the amino acid sequence of SEQ ID NO: 5 or 9, and having an equal function to the polypeptide of (1).

13. The method according to claim 12, wherein the CBP comprises a polypeptide consisting of the amino acid sequence of SEQ ID NO: 5 or 9.

14. The method of claim 1, wherein the CBP-detecting reagent is a medium for detecting CBP-carrying, bacteria or an antibody that binds CBP.

15. The method of claim 3, wherein the CBP-detecting reagent is a medium for detecting CBP-carrying bacteria or an antibody that binds CBP.

16. The method of claim 5, wherein the CBP-detecting reagent is a medium for detecting CBP-carrying bacteria or an antibody that binds CBP.

17. The method of claim 2, wherein the PA-detecting reagent is an antibody that binds PA.

18. The method of claim 4, wherein the PA-detecting reagent is an antibody that binds PA.

19. The method of claim 6, wherein the PA-detecting reagent is an antibody that binds PA.

\* \* \* \* \*